(12) United States Patent
Mukumoto et al.

(10) Patent No.: US 9,872,493 B2
(45) Date of Patent: Jan. 23, 2018

(54) METHOD FOR PROMOTING PLANT GROWTH

(71) Applicant: SUMITOMO CHEMICAL COMPANY, LIMITED, Tokyo (JP)

(72) Inventors: Fujio Mukumoto, Takarazuka (JP); Hiroaki Tamaki, Takarazuka (JP); Shintaro Kusaka, Takarazuka (JP); Mitsuhiko Iwakoshi, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 65 days.

(21) Appl. No.: 14/441,626

(22) PCT Filed: Oct. 31, 2013

(86) PCT No.: PCT/JP2013/080172
§ 371 (c)(1),
(2) Date: May 8, 2015

(87) PCT Pub. No.: WO2014/073626
PCT Pub. Date: May 15, 2014

(65) Prior Publication Data
US 2015/0305332 A1 Oct. 29, 2015

(30) Foreign Application Priority Data
Nov. 9, 2012 (JP) .................. 2012-247264

(51) Int. Cl.
*A01N 43/12* (2006.01)
*A01G 7/06* (2006.01)

(52) U.S. Cl.
CPC ........... *A01N 43/12* (2013.01); *A01G 7/06* (2013.01)

(58) Field of Classification Search
None
See application file for complete search history.

(56) References Cited

U.S. PATENT DOCUMENTS

| | | | |
|---|---|---|---|
| 2,533,086 A | 12/1950 | Blicke | |
| 4,514,211 A | 4/1985 | Rorer | |
| 2004/0248872 A1* | 12/2004 | Abe ............... | A01N 43/00 514/183 |

FOREIGN PATENT DOCUMENTS

| | | |
|---|---|---|
| CN | 1531395 A | 9/2004 |
| CN | 1545507 A | 11/2004 |
| EP | 1 426 367 A1 | 6/2004 |
| JP | 4-342507 A | 11/1992 |
| WO | WO 01/74802 A1 | 10/2001 |
| WO | WO 02/051246 A1 | 7/2002 |
| WO | WO 03/029211 A1 | 4/2003 |
| WO | WO 2007/009661 A2 | 1/2007 |
| WO | WO 2012/153860 A1 | 11/2012 |
| WO | WO 2012/153861 A1 | 11/2012 |

OTHER PUBLICATIONS

Burström and Hansen, "Root Growth Effects of Indan, Indene, and Thionaphthene Derivatives", Physiologia Plantarum 9: 502 (1956).*
Badger et al., "Thionaphthencarboxylic acids" (1957).*
Badger et al., "Thionaphthencarboxylic Acids," Journal of the Chemical Society, 1957, pp. 2624-2630.
Burström et al., "Root Growth Effects of Indan, Indene, and Thionaphthene Derivatives," Physiologia Plantarum, vol. 9, No. 3, 1956, pp. 502-514.
International Preliminary Report on Patentability and Written Opinion of the International Searching Authority (Forms PCT/IB/373 and PCT/ISA/237) for International Application No. PCT/JP2013/080172, dated May 12, 2015.
International Search Report (Form PCT/ISA/210) for International Application No. PCT/JP2013/080172, dated Feb. 10, 2014.
Kasemura et al., "Synthesis and Physiological Activities of Furans and Thiophenes with Methylacetophenone Residues," Bokin Bobai, Journal of Antibacterial and Antifungal Agents, vol. 30, No. 12, 2002, pp. 777-784, with an English abstract.
Sasaki et al., "Biosynthesis, biotechnological production and applications of 5-aminolevulinic acid," Applied Microbiology and Biotechnology, vol. 58, 2002 (Published online Nov. 17, 2001), pp. 23-29.
Tachibana et al., "Synthesis and Physiological Activity of Thiophenes and Furans with 3- and 4-Methoxyacetophenone Derivatives," Journal of Oleo Science, vol. 57, No. 2, 2008, pp. 107-113.

(Continued)

*Primary Examiner* — Robert A Wax
*Assistant Examiner* — Thor Nielsen
(74) *Attorney, Agent, or Firm* — Birch, Stewart, Kolasch & Birch, LLP

(57) ABSTRACT

The present invention provides a method for promoting plant growth, which comprises treating a plant with a compound represented by the following Formula (1):

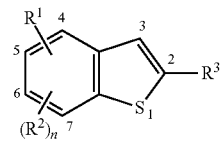

(1)

provided that a method for promoting plant growth which comprises treating plants with a compound corresponding to the following (1) or an agriculturally acceptable salt thereof are excluded,
(1) benzo[b]thiophene-3-carboxylic acid.
The method set forth in one of the above, the plant being soybeans. The method set forth in one of the above, the plant being cotton. A plant seed resulting from treatment with the compound of claim 1 containing an effective quantity of the compound indicated in formula (1). A composition for promoting plant growth and containing an inert component and the compound indicated in formula (1).

10 Claims, No Drawings

(56) References Cited

OTHER PUBLICATIONS

European Patent Office Communication and extended search report issued in the corresponding European Patent Application No. 13852464.0 dated May 3, 2016.

Chinese Office Action and Search Report, dated Mar. 24, 2016, for counterpart Chinese Application No. 201380069562.5 with an English translation.

Schuetz et al., "Benzo[$_b$] thiophene Derivatives I. 6-Methoxybenzo[$_b$] thiophene Analogs of Plant Growth Regulators(1)," Journal of Heterocyclic Chemistry, vol. 4, No. 4, pp. 465-458, Dec. 1967.

\* cited by examiner

METHOD FOR PROMOTING PLANT GROWTH

TECHNICAL FIELD

The present invention relates to a method for promoting plant growth.

BACKGROUND ART

Some chemical substances are known to exert an effect of promoting plant growth by being applied to plants. For example, when aminolevulinic acid is applied to plants, this substance exerts an effect of promoting growth of the plants.

PRIOR ART DOCUMENT

Non-Patent Document

<Biosynthesis, biotechnological production and applications of 5-aminolevulinic acid>K. Sasaki et al., (2002) Applied Microbiology and Biotechnology 58: pp 23-29

SUMMARY OF THE INVENTION

An object of the present invention is to provide a method or the like that excellently promotes plant growth.

Means for Solving the Problems

As a result of thorough examination, the present inventors found that the application of a certain compound to plants promotes growth of the plants and made the present invention.

That is, the present invention is as follows.

[1] A method for promoting plant growth, which comprises treating a plant with a compound represented by the following Formula (1):

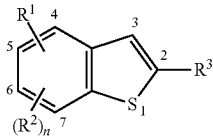

(1)

wherein $R^1$ represents —C(O)W substituted at one of the positions 3, 4, 5, 6, and 7, W represents —ON=$CR^4R^5$, —$OR^6$, —$SR^7$, or —$NR^4R^8$, $R^2$ represents a cyano group, a halogen atom, a nitro group, a C1-C6 alkyl group optionally having one or more groups selected from a group X, a C2-C6 alkenyl group optionally having one or more groups selected from the group X, a C2-C6 alkynyl group optionally having one or more groups selected from the group X, a phenyl group optionally having one or more groups selected from a group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocarbonyl group, —$NR^9R^{10}$, —$S(O)_2NR^4R^9$, —$OR^9$, —$S(O)_mR^9$, or —$SF_5$, substituted at one of the positions 3, 4, 5, 6, and 7 (provided that $R^2$ is substituted at a position different from that of $R^1$), $R^3$ represents a hydrogen atom, a halogen atom, a cyano group, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a C2-C6 alkylcarbonyl group optionally having one or more halogen atoms, a benzoyl group optionally having one or more groups selected from the group Y, —$NR^9R^{10}$, —$S(O)_2NR^4R^9$, —$OR^9$, or —$S(O)_mR^9$, $R^4$ and $R^5$ are the same or different other and each represents a C1-C6 alkyl group optionally having one or more halogen atoms, a phenyl group optionally having one or more groups selected from the group Y, or a hydrogen atom, $R^6$ represents a hydrogen atom, a C1-C6 alkyl group optionally having one or more groups selected from a group Z, a C3-C6 alkenyl group optionally having one or more groups selected from the group X, a C3-C6 alkynyl group optionally having one or more groups selected from the group X, a C4-C7 cycloalkylalkyl group optionally having one or more halogen atoms, a C3-C6 cycloalkyl group optionally having one or more halogen atoms, a phenyl group optionally having one or more groups selected from the group Y, or a C7-C9 phenylalkyl group in which a benzene ring portion may have optionally one or more groups selected from the group Y, $R^7$ represents a hydrogen atom, a C1-C6 alkyl group optionally having one or more groups selected from the group X, a C3-C6 alkenyl group optionally having one or more groups selected from the group X, a C3-C6 alkynyl group optionally having one or more groups selected from the group X, a phenyl group optionally having one or more groups selected from the group Y, or a C7-C9 phenylalkyl group in which a benzene ring portion may have optionally one or more groups selected from the group Y, $R^8$ represents a hydrogen atom, a cyano group, a C1-C6 alkyl group optionally having one or more groups selected from the group Z, a phenyl group optionally having one or more groups selected from the group Y, a benzyl group in which a benzene ring portion may have optionally one or more groups selected from the group Y, —$OR^4$, or —$NR^4R^5$, $R^9$ represents a C1-C6 alkyl group optionally having one or more groups selected from the group X, a C3-C6 alkenyl group optionally having one or more groups selected from the group X, a C3-C6 alkynyl group optionally having one or more groups selected from the group X, a C4-C7 cycloalkylalkyl group optionally having one or more halogen atoms, a C7-C9 phenylalkyl group in which a benzene ring portion may have optionally one or more groups selected from the group Y, a 6-membered aromatic heterocyclic C1-C3 alkyl group in which a 6-membered aromatic heterocycle portion may have optionally one or more groups selected from the group Y, a phenyl group optionally having one or more groups selected from the group Y, a C3-C6 cycloalkyl group optionally having one or more halogen atoms, or a hydrogen atom (provided that, when m in —$S(O)_mR^9$ is 1 or 2, $R^9$ is not a hydrogen atom), $R^{10}$ represents a hydrogen atom, a C1-C4 alkyl group optionally having one or more halogen atoms, a C1-C4 alkylsulfonyl group optionally having one or more halogen atoms, a phenylsulfonyl group optionally having one or more groups selected from the group Y, a C7-C9 phenylalkylsulfonyl group in which a benzene ring portion may have optionally one or more groups selected from the group Y, a C2-C6 alkoxycarbonyl group, —C(O)R$^{11}$, or —C(O)NR$^4$R$^5$, R$^{11}$ represents a hydrogen atom, a C1-C6 alkyl group optionally having one or more halogen atoms, a phenyl group optionally having one or more groups selected from the group Y, a 5-membered aromatic heterocyclic group optionally having one or more groups selected from the group Y, or a 6-membered aromatic heterocyclic group optionally having one or more groups selected from the group Y, m represents 0, 1, or 2, and n represents an integer of 0 to 4 (provided that when n is an integer of 2 or greater, R$^2$s may be the same or different and each is substituted at different positions), the group X represents a group consisting of a halogen atom, a cyano group, and a C1-C6 alkoxy group optionally having one or more halogen atoms, the group Y represents a group consisting of a halogen atom, a cyano group, a nitro group, a C1-C6 alkyl group optionally having one or more halogen atoms, and a C1-C6 alkoxy group optionally having one or more halogen atoms, and the group Z represents a halogen atom, a hydroxyl group, a C1-C6 alkoxy group optionally having one or more halogen atoms, and a C2-C6 alkoxycarbonyl group, (hereinafter, described as a "compound of the present invention")

provided that a method for promoting plant growth which comprises treating plants with a compound corresponding to the following (1) or an agriculturally acceptable salt thereof is excluded, (1) Benzo[b]thiophene-3-carboxylic acid.

[2] The method for promoting plant growth according to [1], wherein the plant is a plant that has been or will be exposed to abiotic stress.

[3] The method according to any one of [1] and [2], wherein the application to the plant includes a spraying treatment, a soil treatment, a seed treatment, or a hydroponic treatment.

[4] The method according to any one of [1] and [2], wherein the application to the plant is the seed treatment.

[5] The method according to any one of [1] to [4], wherein the plant is rice, corn, or wheat.

[6] The method according to any one of [1] to [5], [13] and [14], wherein the plant is a transgenic plant.

[7] The method according to any one of [2] to [6], [13] and [14], wherein the abiotic stress is high-temperature stress.

[8] The method according to any one of [2] to [6], [13] and [14], wherein the abiotic stress is low-temperature stress.

[9] The method according to any one of [2] to [6], [13] and [14], wherein the abiotic stress is drought stress.

[10] Use of the compound represented the Formula (1) described in above [1] for promoting plant growth

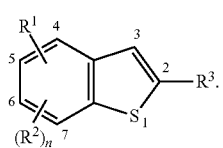

(1)

[11] A plant seed which is obtained by being treated with the compound represented by the Formula (1) described in above [1] in an effective dose,

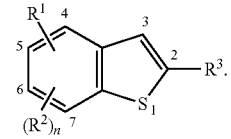

(1)

[12] A composition for promoting plant growth comprising the compound represented by the Formula (1) described in above [1] and inactive ingredients

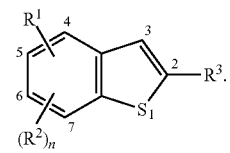

(1)

[13] The method according to any one of [1] to [4], wherein the plant is soybean.

[14] The method according to any one of [1] to [4], wherein the plant is cotton.

MODE FOR CARRYING OUT THE INVENTION

In the present invention, the "promotion of the growth of a plant (hereinafter, described as "growth promotion" in some cases)" means the increase in the rate of seedling establishment, increase in the number of healthy leaves, increase in the height of the plant, increase in the weight of the plant, increase in the leaf area, increase in the number or weight of seeds or fruits, increase in the number of occasion of flower setting or fruit setting, and promoted growth of a root.

The growth promotion can be quantified by the following parameters.

(1) Rate of Seedling Establishment

Seeds of a plant are seeded in, for example, soil, filter paper, an agar medium, or sand and cultivated for a certain period of time. Thereafter, the proportion of the surviving seedlings is investigated.

(2) Number of Healthy Leaves or Proportion of Healthy Leaves

For each plant, the number of healthy leaves is counted, and the total number of healthy leaves is investigated. Alternatively, a ratio of the number of healthy leaves to the total number of the leaves of the plant is investigated.

(3) Plant Height

For each plant, a length from the base to the terminal branch or leave of the overground stem is measured.

(4) Plant Weight

The overground portion of each plant is cut and collected, and the weight thereof is measured to determine a fresh weight of the plant. Alternatively, the cut and collected sample is dried, and then a weight thereof is measured to determine a dry weight of the plant.

(5) Leaf Area

A plant is imaged with a digital camera, and the area of the green portion in the picture is quantified by image analysis software, for example, Win ROOF (manufactured by MITANI CORPORATION), or visually evaluated to determine a leaf area of the plant.

(6) Leaf Color

A leaf of a plant is sampled, and an amount of chlorophyll is measured using a chlorophyll meter (for example, SPAD-502, manufactured by Konica Minolta Sensing Europe B.V.) to determine the leaf color. In addition, the plant is imaged with a digital camera, and the area of the green portion in the picture is quantified by performing color extraction by using image analysis software, for example, Win ROOF (manufactured by MITANI CORPORATION), whereby the area of the green portion of the leaf of the plant is determined.

(7) Number or Weight of Seeds or Fruits

A plant is cultured until it produces seeds or fruits or until the seeds or fruits ripen, and then the number of fruits per plant or the total weight of fruits per plant is measured. Moreover, the plant is cultivated until the seeds ripen, and then constituents of the yield, for example, the number of ears, ripening rate, and thousand kennel weight, are investigated.

(8) Flower Setting Rate, Fruit Setting Rate, Fruition Rate, or Grain Filling Rate A plant is cultivated until it fruits, and the number of set flowers and fruits are counted to determine a fruit setting rate (number of set fruit/number of set flower×100). After the seeds ripen, the number of produced fruits and number of filled grains are counted to determine a fruition rate (number of produced fruit/number of set flower×100) and a grain filling rate (number of filled grain/number of produced fruit×100).

(9) Promoted Growth of Root

A plant is cultivated in soil or cultivated hydroponically, and a length of the root is measured. Alternatively, the root is cut and collected, and a fresh weight thereof or the like is measured.

When a plant is treated with the compound of the present invention by the method of the present invention, the entire plant may be treated, or a portion thereof (foliage, a sprout, a flower, a fruit, a grain, a seed, a bulb, a tuber, a root, and the like) may be treated. Moreover, the plant may be treated at various growth stages thereof (a germination period including a pre-seeding stage, a seeding stage, a post-seeding stage, pre- and post-budding stages, and the like, a period of vegetative growth including a seedling stage, a seedling transplant stage, and a pre-cuttage stage or a seedling insertion stage, a growth stage after planting, a reproductive period including the a pre-flowering stage, a flowering stage, a post-flowering stage, a stage immediately before emergence of ear, an ear emergence stage, and the like, a harvesting period including a time stage prospect of harvest, a stage before prospect of ripening, the period during which fruits start to be colored, and the like). Herein, a bulb refers to a discoid stem, a corm, a rhizome, a tuberous root, a rhizophore, and the like. In addition, a seedling includes a nursery plant raised from a seed, a cuttage, and the like.

Examples of substituents used and described in the present specification will be described below.

Examples of the "halogen atom" in the compound of the present invention include a fluorine atom, a chlorine atom, a bromine atom, an iodine atom, and the like.

Examples of the "C1-C6 alkyl group" in the compound of the present invention include a methyl group, an ethyl group, a propyl group, an isopropyl group, a butyl group, an isobutyl group, a sec-butyl group, a tert-butyl group, a pentyl group, a 2,2-dimethylpropyl group, a 3-methylbutyl group, a 2,3-dimethylbutyl group, a 3,3-dimethylbutyl group, and a hexyl group.

Examples of the "C1-C6 alkyl group optionally having one or more groups selected from the group X" in the compound of the present invention include a methyl group, an ethyl group, a propyl group, an isopropyl group, a butyl group, an isobutyl group, a sec-butyl group, a tert-butyl group, a pentyl group, a 2,2-dimethylpropyl group, a 3-methylbutyl group, a 2,3-dimethylbutyl group, a 3,3-dimethylbutyl group, a hexyl group, a trichloromethyl group, a difluoromethyl group, a trifluoromethyl group, a 2,2,2-trifluoroethyl group, a pentafluoroethyl group, a heptafluoropropyl group, a heptafluoroisopropyl group, a cyanomethyl group, a 2-cyanoethyl group, a methoxymethyl group, a 2-methoxyethyl group, an ethoxymethyl group, a 2-ethoxyethyl group, a trifluoromethoxymethyl group, a 2,2,2-trifluoroethoxymethyl group, and the like.

Examples of the "C2-C6 alkenyl group" in the compound of the present invention include a vinyl group, a 1-propenyl group, an allyl group, an isopropenyl group, a 2-methyl-1-propenyl group, a 1-butenyl group, a 2-butenyl group, a 3-butenyl group, a 1-pentenyl group, a 1-hexenyl group, and the like.

Examples of the "C2-C6 alkenyl group optionally having one or more groups selected from the group X" in the compound of the present invention include a vinyl group, a 1-propenyl group, an allyl group, an isopropenyl group, a 2-methyl-1-propenyl group, a 1-butenyl group, a 2-butenyl group, a 3-butenyl group, a 1-pentenyl group, a 1-hexenyl group, a 2,2-difluoroethenyl group, a 2,2-dichloroethenyl group, a 2-cyano-1-ethenyl group, a 2-methoxy-1-ethenyl group, a 2-ethoxy-1-ethenyl group, a 3,3-difluoro-2-propenyl group, a 3,3-dichloro-2-propenyl group, a 4-methoxy-2-methyl-2-butenyl group, a 3-cyano-2-butenyl group, and the like.

Examples of the "C2-C6 alkynyl group" in the compound of the present invention include an ethynyl group, a propargyl group, a 1-propynyl group, a 1-butynyl group, a 2-butynyl group, a 3-butynyl group, a 3,3-dimethyl-1-butynyl group, a 1-pentynyl group, a 2-pentynyl group, a 1-hexynyl group, and the like.

Examples of the "C2-C6 alkynyl group optionally having one or more groups selected from the group X" in the compound of the present invention include an ethynyl group, a propargyl group, a 1-propynyl group, a 1-butynyl group, a 2-butynyl group, a 3-butynyl group, a 3,3-dimethyl-1-butynyl group, a 1-pentynyl group, a 1-hexynyl group, a 4-chloro-2-butynyl group, a 4-cyano-2-butynyl group, a 5-cyano-2-pentynyl group, a 4-methoxy-2-butynyl group, a 4-(2-chloroethoxy)-2-butynyl group, and the like.

Examples of the "phenyl group optionally having one or more groups selected from the group Y" in the compound of the present invention include a phenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2-cyanophenyl group, a 3-cyanophenyl group, a 4-cyanophenyl group, a 2-nitrophenyl group, a 3-nitrophenyl group, a 4-nitrophenyl group, a 2-methylphenyl group, a 3-methylphenyl group, a 4-methylphenyl group, a 2-isopropylphenyl group, a 3-isopropylphenyl group, a 4-isopropylphenyl group, a 2-butylphenyl group, a 3-butylphenyl group, a 4-butylphenyl group, a 2-isobutylphenyl group, a 3-isobutylphenyl group, a 4-isobutylphenyl group, a 3-tert-butylphenyl group, a 4-tert-butylphenyl group, a 2-difluoromethylphenyl group, a 3-difluoromethylphenyl group, a 4-difluoromethylphenyl group, a 2-trifluoromethylphenyl group, a 3-trifluoromethylphenyl group, a 4-trifluoromethylphenyl group, a 2-(2,2,2-trifluoroethyl)phenyl group, a 3-(2,2,2-trifluoroethyl)phenyl group, a 4-(2,2,2-trifluoroethyl)phenyl group, a 2-pentafluoroethylphenyl group, a 3-pentafluoroethylphenyl group, a 4-pentafluoroethylphenyl group, a 2-heptafluoropropylphenyl group, a 3-heptafluoropropylphenyl group, a 4-heptafluoropropylphenyl group, a 2-heptafluoroisopropylphenyl group, a 3-heptafluoroisopropylphenyl group, a 4-heptafluoroisopropylphenyl group, a 2-methoxyphenyl group, a 3-methoxyphenyl group, a 4-methoxyphenyl group, a 2-tert-butoxyphenyl group, a 3-tert-butoxyphenyl group, a 4-tert-butoxyphenyl group, a 2-pentyloxyphenyl group, a 3-pentyloxyphenyl group, a 4-pentyloxyphenyl group, a 2-(2,2-dimethoxypropoxyl)phenyl group, a 3-(2,2-dimethoxypropoxyl)phenyl group, a 4-(2,2-dimethoxypropoxyl)phenyl group, a 2-(3-methylbutoxyl)phenyl group, a 3-(3-methylbutoxyl)phenyl group, a 4-(3-methylbutoxyl)phenyl group, a 2-difluoromethoxyphenyl group, a 3-difluoromethoxyphenyl group, a 4-difluoromethoxyphenyl group, a 2-trifluoromethoxyphenyl group, a 3-trifluoromethoxyphenyl group, a 4-trifluoromethoxyphenyl group, a 4-(2,2,2-trifluoroethoxyl)phenyl group, and the like.

Examples of the "6-membered aromatic heterocyclic group" in the compound of the present invention include a 2-pyridyl group, a 3-pyridyl group, a 4-pyridyl group, a 3-pyridazinyl group, a 4-pyridazinyl group, a 2-pyrimidinyl group, a 4-pyrimidinyl group, a 5-pyrimidinyl group, a 2-pyrazinyl group, a 4-(1,2,3-triazinyl) group, a 5-(1,2,3-triazinyl) group, a 3-(1,2,4-triazinyl) group, a 5-(1,2,4-triazinyl) group, a 6-(1,2,4-triazinyl) group, and a 2-(1,3,5-triazinyl) group, and the like.

Examples of the "6-membered aromatic heterocyclic group optionally having one or more groups selected from the group Y" in the compound of the present invention include a 2-pyridyl group, a 3-fluoro-2-pyridyl group, a 4-fluoro-2-pyridyl group, a 5-fluoro-2-pyridyl group, a 6-fluoro-2-pyridyl group, a 3-chloro-2-pyridyl group, a 4-chloro-2-pyridyl group, a 5-chloro-2-pyridyl group, a 6-chloro-2-pyridyl group, a 3-bromo-2-pyridyl group, a 4-bromo-2-pyridyl group, a 5-bromo-2-pyridyl group, a 6-bromo-2-pyridyl group, a 3-iodo-2-pyridyl group, a 4-iodo-2-pyridyl group, a 5-iodo-2-pyridyl group, a 6-iodo-2-pyridyl group, a 3-cyano-2-pyridyl group, a 4-cyano-2-pyridyl group, a 5-cyano-2-pyridyl group, a 6-cyano-2-pyridyl group, a 3-nitro-2-pyridyl group, a 4-nitro-2-pyridyl group, a 5-nitro-2-pyridyl group, a 6-nitro-2-pyridyl group, a 3-methyl-2-pyridyl group, a 4-methyl-2-pyridyl group, a 5-methyl-2-pyridyl group, a 6-methyl-2-pyridyl group, a 3-ethyl-2-pyridyl group, a 4-ethyl-2-pyridyl group, a 5-ethyl-2-pyridyl group, a 6-ethyl-2-pyridyl group, a 3-propyl-2-pyridyl group, a 4-propyl-2-pyridyl group, a 5-propyl-2-pyridyl group, a 6-propyl-2-pyridyl group, a 3-isopropyl-2-pyridyl group, a 4-isopropyl-2-pyridyl group, a 5-isopropyl-2-pyridyl group, a 6-isopropyl-2-pyridyl group, a 3-butyl-2-pyridyl group, a 4-butyl-2-pyridyl group, a 5-butyl-2-pyridyl group, a 6-butyl-2-pyridyl group, a 3-isobutyl-2-pyridyl group, a 4-isobutyl-2-pyridyl group, a 5-isobutyl-2-pyridyl group, a 6-isobutyl-2-pyridyl group, a 3-sec-butyl-2-pyridyl group, a 4-sec-butyl-2-pyridyl group, a 5-sec-butyl-2-pyridyl group, a 6-sec-butyl-2-pyridyl group, a 3-tert-butyl-2-pyridyl group, a 4-tert-butyl-2-pyridyl group, a 5-tert-butyl-2-pyridyl group, a 6-tert-butyl-2-pyridyl group, a 3-difluoromethyl-2-pyridyl group, a 4-difluoromethyl-2-pyridyl group, a 5-difluoromethyl-2-pyridyl group, a 6-difluoromethyl-2-pyridyl group, a 3-trifluoromethyl-2-pyridyl group, a 4-trifluoromethyl-2-pyridyl group, a 5-trifluoromethyl-2-pyridyl group, a 6-trifluoromethyl-2-pyridyl group, a 3-(2,2,2-trifluoroethyl)-2-pyridyl group, a 4-(2,2,2-trifluoroethyl)-2-pyridyl group, a 5-(2,2,2-trifluoroethyl)-2-pyridyl group, a 6-(2,2,2-trifluoroethyl)-2-pyridyl group, a 3-pentafluoroethyl-2-pyridyl group, a 4-pentafluoroethyl-2-pyridyl group, a 5-pentafluoroethyl-2-pyridyl group, a 6-pentafluoroethyl-2-pyridyl group, a 3-heptafluoropropyl-2-pyridyl group, a 4-heptafluoropropyl-2-pyridyl group, a 5-heptafluoropropyl-2-pyridyl group, a 6-heptafluoropropyl-2-pyridyl group, a 3-heptafluoroisopropyl-2-pyridyl group, a 4-heptafluoroisopropyl-2-pyridyl group, a 5-heptafluoroisopropyl-2-pyridyl group, a 6-heptafluoroisopropyl-2-pyridyl group, a 3-pyridyl group, a 2-methyl-3-pyridyl group, a 4-methyl-3-pyridyl group, a 5-methyl-3-pyridyl group, a 6-methyl-3-pyridyl group, a 2-ethyl-3-pyridyl group, a 4-ethyl-3-pyridyl group, a 5-ethyl-3-pyridyl group, a 6-ethyl-3-pyridyl group, a 2-propyl-3-pyridyl group, a 4-propyl-3-pyridyl group, a 5-propyl-3-pyridyl group, a 6-propyl-3-pyridyl group, a 2-isopropyl-3-pyridyl group, a 4-isopropyl-3-pyridyl group, a 5-isopropyl-3-pyridyl group, a 6-isopropyl-3-pyridyl group, a 2-butyl-3-pyridyl group, a 4-butyl-3-pyridyl group, a 5-butyl-3-pyridyl group, a 6-butyl-3-pyridyl group, a 2-isobutyl-3-pyridyl group, a 4-isobutyl-3-pyridyl group, a 5-isobutyl-3-pyridyl group, a 6-isobutyl-3-pyridyl group, a 2-sec-butyl-3-pyridyl group, a 4-sec-butyl-3-pyridyl group, a 5-sec-butyl-3-pyridyl group, a 6-sec-butyl-3-pyridyl group, a 2-tert-butyl-3-pyridyl group, a 4-tert-butyl-3-pyridyl group, a 5-tert-butyl-3-pyridyl group, a 6-tert-butyl-3-pyridyl group, a 2-difluoromethyl-3-pyridyl group, a 4-difluoromethyl-3-pyridyl group, a 5-difluoromethyl-3-pyridyl group, a 6-difluoromethyl-3-pyridyl group, a 2-trifluoromethyl-3-pyridyl group, a 4-trifluoromethyl-3-pyridyl group, a 5-trifluoromethyl-3-pyridyl group, a 6-trifluoromethyl-3-pyridyl group, a 2-(2,2,2-trifluoroethyl)-3-pyridyl group, a 4-(2,2,2-trifluoroethyl)-3-pyridyl group, a 5-(2,2,2-trifluoroethyl)-3-pyridyl group, a 6-(2,2,2-trifluoroethyl)-3-pyridyl group, a 2-pentafluoroethyl-3-pyridyl group, a 4-pentafluoroethyl-3-pyridyl group, a 5-pentafluoroethyl-3-pyridyl group, a 6-pentafluoroethyl-3-pyridyl group, a 2-heptafluoropropyl-3-pyridyl group, a 4-heptafluoropropyl-3-pyridyl group, a 5-heptafluoropropyl-3-pyridyl group, a 6-heptafluoropropyl-3-pyridyl group, a 2-heptafluoroisopropyl-3-pyridyl group, a 4-heptafluoroisopropyl-3-pyridyl group, a 5-heptafluoroisopropyl-3-pyridyl group, a 6-heptafluoroisopropyl-3-pyridyl group, a 4-pyridyl group, a 2-methyl-4-pyridyl group, a 3-methyl-4-pyridyl group, a 2-ethyl-4-pyridyl group, a 3-ethyl-4-pyridyl group, a 2-propyl-4-pyridyl group, a 3-propyl-4-pyridyl group, a 2-isopropyl-4-pyridyl group, a 3-isopropyl-4-pyridyl group, a 2-butyl-4-pyridyl group, a 3-butyl-4-pyridyl group, a 2-isobutyl-4-pyridyl group, a 3-isobutyl-4-pyridyl group, a 2-sec-butyl-4-pyridyl group, a 3-sec-butyl-4-pyridyl group, a 2-tert-butyl-4-pyridyl group, a 3-tert-butyl-4-pyridyl group, a 2-difluoromethyl-4-pyridyl group, a 3-difluoromethyl-4-pyridyl group, a 2-trifluoromethyl-4-pyridyl group, a 3-trifluoromethyl-4-pyridyl group, a 2-(2,2,2-trifluoroethyl)-4-pyridyl group, a 3-(2,2,2-trifluoroethyl)-4-pyridyl group, a 2-pentafluoroethyl-4-pyridyl group, a 3-pentafluoroethyl-4-pyridyl group, a 2-heptafluoropropyl-4-pyridyl group, a 3-heptafluoropropyl-4-pyridyl group, a 2-heptafluoroisopropyl-4-pyridyl group, a 3-heptafluoroisopropyl-4-pyridyl group, a 3-pyridazinyl group, a 4-methyl-3-pyridazinyl group, a 5-methyl-3-pyridazinyl group, a 6-methyl-3-pyridazinyl group, a 4-ethyl-3-pyridazinyl group, a 5-ethyl-3-pyridazinyl group, a 6-ethyl-3-pyridazinyl group, a 4-propyl-3-pyridazinyl group, a 5-propyl-3-pyridazinyl group, a 6-propyl-3-pyridazinyl group, a 4-isopropyl-3-pyridazinyl group, a 5-isopropyl-3-pyridazinyl group, a 6-isopropyl-3-pyridazinyl group, a 4-butyl-3-pyridazinyl group, a 5-butyl-3-pyridazinyl group, a 6-butyl-3-pyridazinyl group, a 4-isobutyl-3-pyridazinyl group, a 5-isobutyl-3-pyridazinyl group, a 6-isobutyl-3-pyridazinyl group, a 4-sec-butyl-3-pyridazinyl group, a 5-sec-butyl-3-pyridazinyl group, a 6-sec-butyl-3-pyridazinyl group, a 4-tert-butyl-3-pyridazinyl group, a 5-tert-butyl-3-pyridazinyl group, a 6-tert-butyl-3-pyridazinyl group, a 4-difluoromethyl-3-pyridazinyl group, a 5-difluoromethyl-3-pyridazinyl group, a 6-difluoromethyl-3-pyridazinyl group, a 4-trifluoromethyl-3-pyridazinyl group, a 5-trifluoromethyl-3-pyridazinyl group, a 6-trifluoromethyl-3-pyridazinyl group, a 4-(2,2,2-trifluoroethyl)-3-pyridazinyl group, a 5-(2,2,2-trifluoroethyl)-3-pyridazinyl group, a 6-(2,2,2-trifluoroethyl)-3-pyridazinyl group, a 4-pentafluoroethyl-3-pyridazinyl group, a 5-pentafluoroethyl-3-pyridazinyl group, a 6-pentafluoroethyl-3-pyridazinyl group, a 4-heptafluoropropyl-3-pyridazinyl group, a 5-heptafluoropropyl-3-pyridazinyl group, a 6-heptafluoropropyl-3-pyridazinyl group, a 4-heptafluoroisopropyl-3-pyridazinyl group, a 5-heptafluoroisopropyl-3-pyridazinyl group, a 6-heptafluoroisopropyl-3-pyridazinyl group, a 6-chloro-3-pyridazinyl group, a 6-methoxy-3-pyridazinyl group, a 6-cyano-3-pyridazinyl group, a 4-pyridazinyl group, a 3-methyl-4-pyridazinyl group, a 5-methyl-4-pyridazinyl group, a 6-methyl-4-pyridazinyl group, a 3-ethyl-4-pyridazinyl group, a 5-ethyl-4-pyridazinyl group, a 6-ethyl-4-pyridazinyl group, a 3-propyl-4-pyridazinyl group, a 5-propyl-4-pyridazinyl group, a 6-propyl-4-pyridazinyl group, a 3-isopropyl-4-pyridazinyl group, a 5-isopropyl-4-pyridazinyl group, a 6-isopropyl-4-pyridazinyl group, a 3-butyl-4-pyridazinyl group, a 5-butyl-4-pyridazinyl group, a 6-butyl-4-pyridazinyl group, a 3-isobutyl-4-pyridazinyl group, a 5-isobutyl-4-pyridazinyl group, a 6-isobutyl-4-pyridazinyl group, a 3-sec-butyl-4-pyridazinyl group, a 5-sec-butyl-4-pyridazinyl group, a 6-sec-butyl-4-pyridazinyl group, a 3-tert-butyl-4-pyridazinyl group, a 5-tert-butyl-4-pyridazinyl group, a 6-tert-butyl-4-pyridazinyl group, a 3-difluoromethyl-4-pyridazinyl group, a 5-difluoromethyl-4-pyridazinyl group, a 6-difluoromethyl-4-pyridazinyl group, a 3-trifluoromethyl-4-pyridazinyl group, a 5-trifluoromethyl-4-pyridazinyl group, a 6-trifluoromethyl-4-pyridazinyl group, a 3-(2,2,2-trifluoroethyl)-4-pyridazinyl group, a 5-(2,2,2-trifluoroethyl)-4-pyridazinyl group, a 6-(2,2,2-trifluoroethyl)-4-pyridazinyl group, a 3-pentafluoroethyl-4-pyridazinyl group, a 5-pentafluoroethyl-4-pyridazinyl group, a 6-pentafluoroethyl-4-pyridazinyl group, a 3-heptafluoropropyl-4-pyridazinyl group, a 5-heptafluoropropyl-4-pyridazinyl group, a 6-heptafluoropropyl-4-pyridazinyl group, a 3-heptafluoroisopropyl-4-pyridazinyl group, a 5-heptafluoroisopropyl-4-pyridazinyl group, a 6-heptafluoroisopropyl-4-pyridazinyl group, a 2-pyrimidinyl group, a 4-methyl-2-pyrimidinyl group, a 5-methyl-2-pyrimidinyl group, a 4-ethyl-2-pyrimidinyl group, a 5-ethyl-2-pyrimidinyl group, a 4-propyl-2-pyrimidinyl group, a 5-propyl-2-pyrimidinyl group, a 4-isopropyl-2-pyrimidinyl group, a 5-isopropyl-2-pyrimidinyl group, a 4-butyl-2-pyrimidinyl group, a 5-butyl-2-pyrimidinyl group, a 4-isobutyl-2-pyrimidinyl group, a 5-isobutyl-2-pyrimidinyl group, a 4-sec-butyl-2-pyrimidinyl group, a 5-sec-butyl-2-pyrimidinyl group, a 4-tert-butyl-2-pyrimidinyl group, a 5-tert-butyl-2-pyrimidinyl group, 4-difluoromethyl-2-pyrimidinyl group, a 5-difluoromethyl-2-pyrimidinyl group, a 4-trifluoromethyl-2-pyrimidinyl group, a 5-trifluoromethyl-2-pyrimidinyl group, a 4-(2,2,2-trifluoroethyl)-2-pyrimidinyl group, a 5-(2,2,2-trifluoroethyl)-2-pyrimidinyl group, a 4-pentafluoroethyl-2-pyrimidinyl group, a 5-pentafluoroethyl-2-pyrimidinyl group, a 4-heptafluoropropyl-2-pyrimidinyl group, a 5-heptafluoropropyl-2-pyrimidinyl group, a 4-heptafluoroisopropyl-2-pyrimidinyl group, a 5-heptafluoroisopropyl-2-pyrimidinyl group, a 4-chloro-2-pyrimidinyl group, a 5-chloro-2-pyrimidinyl group, a 4-cyano-2-pyrimidinyl group, a 5-cyano-2-pyrimidinyl group, a 5-nitro-2-pyrimidinyl group, a 4-pyrimidinyl group, a 2-methyl-4-pyrimidinyl group, a 5-methyl-4-pyrimidinyl group, a 6-methyl-4-pyrimidinyl group, a 2-ethyl-4-pyrimidinyl group, a 5-ethyl-4-pyrimidinyl group, a 6-ethyl-4-pyrimidinyl group, a 2-propyl-4-pyrimidinyl group, a 5-propyl-4-pyrimidinyl group, a 6-propyl-4-pyrimidinyl group, a 2-isopropyl-4-pyrimidinyl group, a 5-isopropyl-4-pyrimidinyl group, a 6-isopropyl-4-pyrimidinyl group, a 2-butyl-4-pyrimidinyl group, a 5-butyl-4-pyrimidinyl group, a 6-butyl-4-pyrimidinyl group, a 2-isobutyl-4-pyrimidinyl group, a 5-isobutyl-4-pyrimidinyl group, a 6-isobutyl-4-pyrimidinyl group, a 2-sec-butyl-4-pyrimidinyl group, a 5-sec-butyl-4-pyrimidinyl group, a 6-sec-butyl-4-pyrimidinyl group, a 2-tert-butyl-4-pyrimidinyl group, a 5-tert-butyl-4-pyrimidinyl group, a 6-tert-butyl-4-pyrimidinyl group, a 2-difluoromethyl-4-pyrimidinyl group, a 5-difluoromethyl-4-pyrimidinyl group, a 6-difluoromethyl-4-pyrimidinyl group, a 2-trifluoromethyl-4-pyrimidinyl group, a 5-trifluoromethyl-4-pyrimidinyl group, a 6-trifluoromethyl-4-pyrimidinyl group, a 2-(2,2,2-trifluoroethyl)-4-pyrimidinyl group, a 5-(2,2,2-trifluoroethyl)-4-pyrimidinyl group, a 6-(2,2,2-trifluoroethyl)-4-pyrimidinyl group, a 2-pentafluoroethyl-4-pyrimidinyl group, a 5-pentafluoroethyl-4-pyrimidinyl group, a 6-pentafluoroethyl-4-pyrimidinyl group, a 2-heptafluoropropyl-4-pyrimidinyl group, a 5-heptafluoropropyl-4-pyrimidinyl group, a 6-heptafluoropropyl-4-pyrimidinyl group, a 2-heptafluoroisopropyl-4-pyrimidinyl group, a 5-heptafluoroisopropyl-4-pyrimidinyl group, a 6-heptafluoroisopropyl-4-pyrimidinyl group, a 2-chloro-4-pyrimidinyl group, a 2-cyano-4-pyrimidinyl group, a 5-chloro-4-pyrimidinyl group, a 5-cyano-4-pyrimidinyl group, a 5-nitro-4-pyrimidinyl group, a 5-pyrimidinyl group, a 2-methyl-5-pyrimidinyl group, a 4-methyl-5-pyrimidinyl group, a 2-ethyl-5-pyrimidinyl group, a 4-ethyl-5-pyrimidinyl group, a 2-propyl-5-pyrimidinyl group, a 4-propyl-5-pyrimidinyl group, a 2-isopropyl-5-pyrimidinyl group, a 4-isopropyl-5-pyrimidinyl group, a 2-butyl-5-pyrimidinyl group, a 4-butyl-5-pyrimidinyl group, a 2-isobutyl-5-pyrimidinyl group, a 4-isobutyl-5-pyrimidinyl group, a 2-sec-butyl-5-pyrimidinyl group, a 4-sec-butyl-5-pyrimidinyl group, a 2-tert-butyl-5-pyrimidinyl group, a 4-tert-butyl-5-pyrimidinyl group, a 2-difluromethyl-5-pyrimidinyl group, a 4-difluromethyl-5-pyrimidinyl group, a 2-trifluromethyl-5-pyrimidinyl group, a 4-trifluromethyl-5-pyrimidinyl group, a 2-(2,2,2-trifluoroethyl)-5-pyrimidinyl group, a 4-(2,2,2-trifluoroethyl)-5-pyrimidinyl group, a 2-pentafluoroethyl-5-pyrimidinyl group, a 4-pentafluoroethyl-5-pyrimidinyl group, a 2-heptafluoropropyl-5-pyrimidinyl group, a 4-heptafluorpropyl-5-pyrimidinyl group, a 2-heptafluoroisopropyl-5-pyrimidinyl group, a 4-heptafluoroisopropyl-5-pyrimidinyl group, a 2-pyrazinyl group, a 3-methyl-2-pyrazinyl group, a 5-methyl-2-pyrazinyl group, a 6-methyl-2-pyrazinyl group, a 3-ethyl-2-pyrazinyl group, a 5-ethyl-2-pyrazinyl group, a 6-ethyl-2-pyrazinyl group, a 3-propyl-2-pyrazinyl group, a 5-propyl-2-pyrazinyl group, a 6-propyl-2-pyrazinyl group, a 3-isopropyl-2-pyrazinyl group, a 5-isopropyl-2-pyrazinyl group, a 6-isopropyl-2-pyrazinyl group, a 3-butyl-2-pyrazinyl group, a 5-butyl-2-pyrazinyl group, a 6-butyl-2-pyrazinyl group, a 3-isobutyl-2-pyrazinyl group, a 5-isobutyl-2-pyrazinyl group, a 6-isobutyl-2-pyrazinyl group, a 3-sec-butyl-2-pyrazinyl group, a 5-sec-butyl-2-pyrazinyl group, a 6-sec-butyl-2-pyrazinyl group, a 3-tert-butyl-2-pyrazinyl group, a 5-tert-butyl-2-pyrazinyl group, a 6-tert-butyl-2-pyrazinyl group, a 3-difluoromethyl-2-pyrazinyl group, a 5-difluoromethyl-2-pyrazinyl group, a 6-difluoromethyl-2-pyrazinyl group, a 3-trifluoromethyl-2-pyrazinyl group, a 5-trifluoromethyl-2-pyrazinyl group, a 6-trifluoromethyl-2-pyrazinyl group, a 3-(2,2,2-trifluoroethyl)-2-pyrazinyl group, a 5-(2,2,2-trifluoroethyl)-2-pyrazinyl group, a 6-(2,2,2-trifluoroethyl)-2-pyrazinyl group, a 3-pentafluoroethyl-2-pyrazinyl group, a 5-pentafluoroethyl-2-pyrazinyl group, a 6-pentafluoroethyl-2-pyrazinyl group, a 3-heptafluoropropyl-2-pyrazinyl group, a 5-heptafluoropropyl-2-pyrazinyl group, a 6-heptafluoropropyl-2-pyrazinyl group, a 3-heptafluoroisopropyl-2-pyrazinyl group, a 5-heptafluoroisopropyl-2-pyrazinyl group, a 6-heptafluoroisopropyl-2-pyrazinyl group, a 3-chloro-2-pyrazinyl group, a 3-cyano-2-pyrazinyl group, a 3-nitro-2-pyrazinyl group, a 5-chloro-2-pyrazinyl group, a 5-cyano-2-pyrazinyl group, a 5-nitro-2-pyrazinyl group, a 6-chloro-2-pyrazinyl group, a 4-(1,2,3-triazinyl) group, a 5-methyl-4-(1,2,3-triazinyl) group, a 6-methyl-4-(1,2,3-triazinyl) group, a 5-ethyl-4-(1,2,3-triazinyl) group, a 6-ethyl-4-(1,2,3-triazinyl) group, a 5-propyl-4-(1,2,3-triazinyl) group, a 6-propyl-4-(1,2,3-triazinyl) group, a 5-isopropyl-4-(1,2,3-triazinyl) group, a 6-isopropyl-4-(1,2,3-triazinyl) group, a 5-butyl-4-(1,2,3-triazinyl) group, a 6-butyl-4-(1,2,3-triazinyl) group, a 5-isobutyl-4-(1,2,3-triazinyl) group, a 6-isobutyl-4-(1,2,3-triazinyl) group, a 5-sec-butyl-4-(1,2,3-triazinyl) group, a 6-sec-butyl-4-(1,2,3-triazinyl) group, a 5-tert-butyl-4-(1,2,3-triazinyl) group, a 6-tert-butyl-4-(1,2,3-triazinyl) group, a 5-difluoromethyl-4-(1,2,3-triazinyl) group, a 6-difluoromethyl-4-(1,2,3-triazinyl) group, a 5-trifluoromethyl-4-(1,2,3-triazinyl) group, a 6-trifluoromethyl-4-(1,2,3-triazinyl) group, a 5-(2,2,2-trifluoroethyl)-4-(1,2,3-triazinyl) group, a 6-(2,2,2-trifluoroethyl)-4-(1,2,3-triazinyl) group, a 5-pentafluoroethyl-4-(1,2,3-triazinyl) group, a 6-pentafluoroethyl-4-(1,2,3-triazinyl) group, a 5-heptafluoropropyl-4-(1,2,3-triazinyl) group, a 6-heptafluoropropyl-4-(1,2,3-triazinyl) group, a 5-heptafluoroisopropyl-4-(1,2,3-triazinyl) group, a 6-heptafluoroisopropyl-4-(1,2,3-triazinyl) group, a 5-(1,2,3-triazinyl) group, a 4-methyl-5-(1,2,3-triazinyl) group, a 4-ethyl-5-(1,2,3-triazinyl) group, a 4-propyl-5-(1,2,3-triazinyl) group, a 4-isopropyl-5-(1,2,3-triazinyl) group, a 4-butyl-5-(1,2,3-triazinyl) group, a 4-isobutyl-5-(1,2,3-triazinyl) group, a 4-sec-butyl-5-(1,2,3-triazinyl) group, a 4-tert-butyl-5-(1,2,3-triazinyl) group, a 4-difluoromethyl-5-(1,2,3-triazinyl) group, a 4-trifluoromethyl-5-(1,2,3-triazinyl) group, a 4-(2,2,2-trifluoroethyl)-5-(1,2,3-triazinyl) group, a 4-pentafluoroethyl-5-(1,2,3-triazinyl) group, a 4-heptafluoropropyl-5-(1,2,3-triazinyl) group, a 4-heptafluoisopropyl-5-(1,2,3-triazinyl) group, a 3-(1,2,4-triazinyl) group, a 5-methyl-3-(1,2,4-triazinyl) group, a 6-methyl-3-(1,2,4-triazinyl) group, a 5-ethyl-3-(1,2,4-triazinyl) group, a 6-ethyl-3-(1,2,4-triazinyl) group, a 5-propyl-3-(1,2,4-triazinyl) group, a 6-propyl-3-(1,2,4-triazinyl) group, a 5-isopropyl-3-(1,2,4-triazinyl) group, a 6-isopropyl-3-(1,2,4-triazinyl) group, a 5-butyl-3-(1,2,4-triazinyl) group, a 6-butyl-3-(1,2,4-triazinyl) group, a 5-isobutyl-3-(1,2,4-triazinyl) group, a 6-isobutyl-3-(1,2,4-triazinyl) group, a 5-sec-butyl-3-(1,2,4-triazinyl) group, a 6-sec-butyl-3-(1,2,4-triazinyl) group, a 5-tert-butyl-3-(1,2,4-triazinyl) group, a 6-tert-butyl-3-(1,2,4-triazinyl) group, a 5-difluoromethyl-3-(1,2,4-triazinyl) group, a 6-difluoromethyl-3-(1,2,4-triazinyl) group, a 5-trifluoromethyl-3-(1,2,4-triazinyl) group, a 6-trifluoromethyl-3-(1,2,4-triazinyl) group, a 5-(2,2,2-trifluoroethyl)-3-(1,2,4-triazinyl) group, a 6-(2,2,2-trifluoroethyl)-3-(1,2,4-triazinyl) group, a 5-pentafluoroethyl-3-(1,2,4-triazinyl) group, a 6-pentafluoroethyl-3-(1,2,4-triazinyl) group, a 5-heptafluoropropyl-3-(1,2,4-triazinyl) group, a 6-heptafluoropropyl-3-(1,2,4-triazinyl) group, a 5-heptafluoroisopropyl-3-(1,2,4-triazinyl) group, a 6-heptafluoroisopropyl-3-(1,2,4-triazinyl) group, a 5-(1,2,4-triazinyl) group, a 3-methyl-5-(1,2,4-triazinyl) group, a 6-methyl-5-(1,2,4-triazinyl) group, a 3-ethyl-5-(1,2,4-triazinyl) group, a 6-ethyl-5-(1,2,4-triazinyl) group, a 3-propyl-5-(1,2,4-triazinyl) group, a 6-propyl-5-(1,2,4-triazinyl) group, a 3-isopropyl-5-(1,2,4-triazinyl) group, a 6-isopropyl-5-(1,2,4-triazinyl) group, a 3-butyl-5-(1,2,4-triazinyl) group, a 6-butyl-5-(1,2,4-triazinyl) group, a 3-isobutyl-5-(1,2,4-triazinyl) group, a 6-isobutyl-5-(1,2,4-triazinyl) group, a 3-sec-butyl-5-(1,2,4-triazinyl) group, a 6-sec-butyl-5-(1,2,4-triazinyl) group, a 3-tert-butyl-5-(1,2,4-triazinyl) group, a 6-tert-butyl-5-(1,2,4-triazinyl) group, a 3-difluoromethyl-5-(1,2,4-triazinyl) group, a 6-difluoromethyl-5-(1,2,4-triazinyl) group, a 3-trifluoromethyl-5-(1,2,4-triazinyl) group, a 6-trifluoromethyl-5-(1,2,4-triazinyl) group, a 3-(2,2,2-trifluoroethyl)-5-(1,2,4-triazinyl) group, a 6-(2,2,2-trifluoroethyl)-5-(1,2,4-triazinyl) group, a 3-pentafluoroethyl-5-(1,2,4-triazinyl) group, a 6-pentafluoroethyl-5-(1,2,4-triazinyl) group, a 3-heptafluoropropyl-5-(1,2,4-triazinyl) group, a 6-heptafluoropropyl-5-(1,2,4-triazinyl) group, a 3-heptafluoroisopropyl-5-(1,2,4-triazinyl) group, a 6-heptafluoroisopropyl-5-(1,2,4-triazinyl) group, a 6-(1,2,4-triazinyl) group, a 3-methyl-6-(1,2,4-triazinyl) group, a 5-methyl-6-(1,2,4-triazinyl) group, a 3-ethyl-6-(1,2,4-triazinyl) group, a 5-ethyl-6-(1,2,4-triazinyl) group, a 3-propyl-6-(1,2,4-triazinyl) group, a 5-propyl-6-(1,2,4-triazinyl) group, a 3-isopropyl-6-(1,2,4-triazinyl) group, a 5-isopropyl-6-(1,2,4-triazinyl) group, a 3-butyl-6-(1,2,4-triazinyl) group, a 5-butyl-6-(1,2,4-triazinyl) group, a 3-isobutyl-6-(1,2,4-triazinyl) group, a 5-isobutyl-6-(1,2,4-triazinyl) group, a 3-sec-butyl-6-(1,2,4-triazinyl) group, a 5-sec-butyl-6-(1,2,4-triazinyl) group, a 3-tert-butyl-6-(1,2,4-triazinyl) group, a 5-tert-butyl-6-(1,2,4-triazinyl) group, a 3-difluoromethyl-6-(1,2,4-triazinyl) group, a 5-difluoromethyl-6-(1,2,4-triazinyl) group, a 3-trifluoromethyl-6-(1,2,4-triazinyl) group, a 5-trifluoromethyl-6-(1,2,4-triazinyl) group, a 3-(2,2,2-trifluoroethyl)-6-(1,2,4-triazinyl) group, a 5-(2,2,2-trifluoroethyl)-6-(1,2,4-triazinyl) group, a 3-pentafluoroethyl-6-(1,2,4-triazinyl) group, a 5-pentafluoroethyl-6-(1,2,4-triazinyl) group, a 3-heptafluoropropyl-6-(1,2,4-triazinyl) group, a 5-heptafluoropropyl-6-(1,2,4-triazinyl) group, a 3-heptafluoroisopropyl-6-(1,2,4-triazinyl) group, a 5-heptafluoroisopropyl-6-(1,2,4-triazinyl) group, a 2-(1,3,5-triazinyl) group, a 4-chloro-2-(1,3,5-triazinyl) group, a 4,6-dichloro-2-(1,3,5-triazinyl) group, a 4-methyl-2-(1,3,5-triazinyl) group, a 4-ethyl-2-(1,3,5-triazinyl) group, a 4-propyl-2-(1,3,5-triazinyl) group, a 4-isopropyl-2-(1,3,5-triazinyl) group, a 4-butyl-2-(1,3,5-triazinyl) group, a 4-isobutyl-2-(1,3,5-triazinyl) group, a 4-sec-butyl-2-(1,3,5-triazinyl) group, a 4-tert-butyl-2-(1,3,5-triazinyl) group, a 4-difluoromethyl-2-(1,3,5-triazinyl) group, a 4-trifluoromethyl-2-(1,3,5-triazinyl) group, a 4-(2,2,2-trifluoroethyl)-2-(1,3,5-triazinyl) group, a 4-pentafluoroethyl-2-(1,3,5-triazinyl) group, a 4-heptafluoropropyl-2-(1,3,5-triazinyl) group, a 4-heptafluoroisopropyl-2-(1,3,5-triazinyl) group, and the like.

Examples of the "5-membered aromatic heterocyclic group" in the compound of the present invention include a 1-pyrazolyl group, a 1-imidazolyl group, a 1-pyrrolyl group, a 2-pyrrolyl group, a 3-pyrrolyl group, a 1-(1,2,4-triazolyl)

group, a 1-(1,2,3,4-tetrazolyl) group, a 1-(1,2,3,5-tetrazolyl) group, a 2-furyl group, a 3-furyl group, a 2-thienyl group, a 3-thienyl group, and the like.

Examples of the "5-membered aromatic heterocyclic group optionally having one or more groups selected from the group Y" in the compound of the present invention include a 1-pyrazolyl group, a 3-chloro-1-pyrazolyl group, a 3-bromo-1-pyrazolyl group, a 3-nitro-1-pyrazolyl group, a 3-methyl-1-pyrazolyl group, a 3-trifluoromethyl-1-pyrazolyl group, a 4-methyl-1-pyrazolyl group, a 4-chloro-1-pyrazolyl group, a 4-bromo-1-pyrazolyl group, a 4-cyano-1-pyrazolyl group, a 3,5-dimethyl-1-pyrazolyl group, an 1-imidazolyl group, a 4-trifluoromethyl-1-imidazolyl group, a 1-pyrrolyl group, a 2-fluoro-1-pyrrolyl group, a 3-cyano-1-pyrrolyl group, a 2-methyl-1-pyrrolyl group, a 3-trifluoromethyl-1-pyrrolyl group, a 3-nitro-1-pyrrolyl group, a 2-pyrrolyl group, a 3-fluoro-2-pyrrolyl group, a 4-fluoro-2-pyrrolyl group, a 5-fluoro-2-pyrrolyl group, a 3-chloro-2-pyrrolyl group, a 4-chloro-2-pyrrolyl group, a 5-chloro-2-pyrrolyl group, a 3-bromo-2-pyrrolyl group, a 4-bromo-2-pyrrolyl group, a 5-bromo-2-pyrrolyl group, a 3-iodo-2-pyrrolyl group, a 4-iodo-2-pyrrolyl group, a 5-iodo-2-pyrrolyl group, a 3-cyano-2-pyrrolyl group, a 4-cyano-2-pyrrolyl group, a 5-cyano-2-pyrrolyl group, a 3-nitro-2-pyrrolyl group, a 4-nitro-2-pyrrolyl group, a 5-nitro-2-pyrrolyl group, a 3-methyl-2-pyrrolyl group, a 4-methyl-2-pyrrolyl group, a 5-methyl-2-pyrrolyl group, a 3-ethyl-2-pyrrolyl group, a 4-ethyl-2-pyrrolyl group, a 5-ethyl-2-pyrrolyl group, a 3-propyl-2-pyrrolyl group, a 4-propyl-2-pyrrolyl group, a 5-propyl-2-pyrrolyl group, a 3-isopropyl-2-pyrrolyl group, a 4-isopropyl-2-pyrrolyl group, a 5-isopropyl-2-pyrrolyl group, a 3-tert-butyl-2-pyrrolyl group, a 4-tert-butyl-2-pyrrolyl group, a 5-tert-butyl-2-pyrrolyl group, a 3-difluoromethyl-2-pyrrolyl group, a 4-difluoromethyl-2-pyrrolyl group, a 5-difluoromethyl-2-pyrrolyl group, a 3-trifluoromethyl-2-pyrrolyl group, a 4-trifluoromethyl-2-pyrrolyl group, a 5-trifluoromethyl-2-pyrrolyl group, a 3-pyrrolyl group, a 2-fluoro-3-pyrrolyl group, a 4-fluoro-3-pyrrolyl group, a 5-fluoro-3-pyrrolyl group, a 2-chloro-3-pyrrolyl group, a 4-chloro-3-pyrrolyl group, a 5-chloro-3-pyrrolyl group, a 2-bromo-3-pyrrolyl group, a 4-bromo-3-pyrrolyl group, a 5-bromo-3-pyrrolyl group, a 2-iodo-3-pyrrolyl group, a 4-iodo-3-pyrrolyl group, a 5-iodo-3-pyrrolyl group, a 2-cyano-3-pyrrolyl group, a 4-cyano-3-pyrrolyl group, a 5-cyano-3-pyrrolyl group, a 2-nitro-3-pyrrolyl group, a 4-nitro-3-pyrrolyl group, a 5-nitro-3-pyrrolyl group, a 2-methyl-3-pyrrolyl group, a 4-methyl-3-pyrrolyl group, a 5-methyl-3-pyrrolyl group, a 2-ethyl-3-pyrrolyl group, a 4-ethyl-3-pyrrolyl group, a 5-ethyl-3-pyrrolyl group, a 2-propyl-3-pyrrolyl group, a 4-propyl-3-pyrrolyl group, a 5-propyl-3-pyrrolyl group, a 2-isopropyl-3-pyrrolyl group, a 4-isopropyl-3-pyrrolyl group, a 5-isopropyl-3-pyrrolyl group, a 2-tert-butyl-3-pyrrolyl group, a 4-tert-butyl-3-pyrrolyl group, a 5-tert-butyl-3-pyrrolyl group, a 2-difluoromethyl-3-pyrrolyl group, a 4-difluoromethyl-3-pyrrolyl group, a 5-difluoromethyl-3-pyrrolyl group, a 2-trifluoromethyl-3-pyrrolyl group, a 4-trifluoromethyl-3-pyrrolyl group, a 5-trifluoromethyl-3-pyrrolyl group, a 1-(1,2,4-triazolyl) group, a 3-chloro-1-(1,2,4-triazolyl) group, a 1-(1,2,3,4-tetrazolyl) group, a 1-(1,2,3,5-tetrazolyl) group, a 2-furyl group, a 3-chloro-2-furyl group, a 5-bromo-2-furyl group, a 3-iodo-2-furyl group, a 4-cyano-2-furyl group, a 5-nitro-2-furyl group, a 3-methyl-2-furyl group, a 4-tert-butyl-2-furyl group, a 5-methyl-2-furyl group, a 5-trifluoromethyl-2-furyl group, a 3-furyl group, a 2-fluoro-3-furyl group, a 4-chloro-3-furyl group, a 2-bromo-3-furyl group, a 5-bromo-3-furyl group, a 2-iodo-3-furyl group, a 4-cyano-3-furyl group, a 4-nitro-3-furyl group, a 2-methyl-3-furyl group, a 2-tert-butyl-3-furyl group, a 4-difluoromethyl-3-furyl group, a 5-difluoromethyl-3-furyl group, a 2-trifluoromethyl-3-furyl group, a 4-trifluoromethyl-3-furyl group, a 5-trifluoromethyl-3-furyl group, a 2-thienyl group, a 3-fluoro-2-thienyl group, a 4-fluoro-2-thienyl group, a 5-fluoro-2-thienyl group, a 3-chloro-2-thienyl group, a 4-chloro-2-thienyl group, a 5-chloro-2-thienyl group, a 3-bromo-2-thienyl group, a 4-bromo-2-thienyl group, a 5-bromo-2-thienyl group, a 3-iodo-2-thienyl group, a 4-iodo-2-thienyl group, a 5-iodo-2-thienyl group, a 3-cyano-2-thienyl group, a 4-cyano-2-thienyl group, a 5-cyano-2-thienyl group, a 3-nitro-2-thienyl group, a 4-nitro-2-thienyl group, a 5-nitro-2-thienyl group, a 3-methyl-2-thienyl group, a 4-methyl-2-thienyl group, a 5-methyl-2-thienyl group, a 3-ethyl-2-thienyl group, a 4-ethyl-2-thienyl group, a 5-ethyl-2-thienyl group, a 3-propyl-2-thienyl group, a 4-propyl-2-thienyl group, a 5-propyl-2-thienyl group, a 3-isopropyl-2-thienyl group, a 4-isopropyl-2-thienyl group, a 5-isopropyl-2-thienyl group, a 3-tert-butyl-2-thienyl group, a 4-tert-butyl-2-thienyl group, a 5-tert-butyl-2-thienyl group, a 3-difluoromethyl-2-thienyl group, a 4-difluoromethyl-2-thienyl group, a 5-difluoromethyl-2-thienyl group, a 3-trifluoromethyl-2-thienyl group, a 4-trifluoromethyl-2-thienyl group, a 5-trifluoromethyl-2-thienyl group, a 3-thienyl group, a 2-fluoro-3-thienyl group, a 4-fluoro-3-thienyl group, a 5-fluoro-3-thienyl group, a 2-chloro-3-thienyl group, a 4-chloro-3-thienyl group, a 5-chloro-3-thienyl group, a 2-bromo-3-thienyl group, a 4-bromo-3-thienyl group, a 5-bromo-3-thienyl group, a 2-iodo-3-thienyl group, a 4-iodo-3-thienyl group, a 5-iodo-3-thienyl group, a 2-cyano-3-thienyl group, a 4-cyano-3-thienyl group, a 5-cyano-3-thienyl group, a 2-nitro-3-thienyl group, a 4-nitro-3-thienyl group, a 5-nitro-3-thienyl group, a 2-methyl-3-thienyl group, a 4-methyl-3-thienyl group, a 5-methyl-3-thienyl group, a 2-ethyl-3-thienyl group, a 4-ethyl-3-thienyl group, a 5-ethyl-3-thienyl group, a 2-propyl-3-thienyl group, a 4-propyl-3-thienyl group, a 5-propyl-3-thienyl group, a 2-isopropyl-3-thienyl group, a 4-isopropyl-3-thienyl group, a 5-isopropyl-3-thienyl group, a 2-tert-butyl-3-thienyl group, a 4-tert-butyl-3-thienyl group, a 5-tert-butyl-3-thienyl group, a 2-difluoromethyl-3-thienyl group, a 4-difluoromethyl-3-thienyl group, a 5-difluoromethyl-3-thienyl group, a 2-trifluoromethyl-3-thienyl group, a 4-trifluoromethyl-3-thienyl group, a 5-trifluoromethyl-3-thienyl group, and the like.

Examples of the "C2-C6 alkylcarbonyl group" in the compound of the present invention include an acetyl group, an ethylcarbonyl group, a propylcarbonyl group, an isopropylcarbonyl group, a butylcarbonyl group, an isobutylcarbonyl group, a sec-butylcarbonyl group, a tert-butylcarbonyl group, a pentylcarbonyl group, a 2,2-dimethylpropylcarbonyl group, a 3-methylbutylcarbonyl group, a pentylcarbonyl group, and the like.

Examples of the "C2-C6 alkylcarbonyl group optionally having one or more halogen atoms" in the compound of the present invention include an acetyl group, an ethylcarbonyl group, a propylcarbonyl group, an isopropylcarbonyl group, a butylcarbonyl group, an isobutylcarbonyl group, a sec-butylcarbonyl group, a tert-butylcarbonyl group, a pentylcarbonyl group, a 2,2-dimethylpropylcarbonyl group, a 3-methylbutylcarbonyl group, a trichloroacetyl group, a difluoroacetyl group, a trifluoroacetyl group, a (2,2,2-trifluoroethyl)carbonyl group, a pentafluoroethylcarbonyl group, a heptafluoropropylcarbonyl group, a heptafluoroisopropylcarbonyl group, and the like.

Examples of the "benzoyl group optionally having one or more groups selected from the group Y" in the compound of the present invention include a benzoyl group, a 2-fluorobenzoyl group, a 3-fluorobenzoyl group, a 4-fluorobenzoyl group, a 2-chlorobenzoyl group, a 3-chlorobenzoyl group, a 4-chlorobenzoyl group, a 2-bromobenzoyl group, a 3-bromobenzoyl group, a 4-bromobenzoyl group, a 2-iodobenzoyl group, a 3-iodobenzoyl group, a 4-iodobenzoyl group, a 2-cyanobenzoyl group, a 3-cyanobenzoyl group, a 4-cyanobenzoyl group, a 2-nitrobenzoyl group, a 3-nitrobenzoyl group, a 4-nitrobenzoyl group, a 2-methylbenzoyl group, a 3-methylbenzoyl group, a 4-methylbenzoyl group, a 2-ethylbenzoyl group, a 3-ethylbenzoyl group, a 4-ethylbenzoyl group, a 2-propylbenzoyl group, a 3-propylbenzoyl group, a 4-propylbenzoyl group, a 2-isopropylbenzoyl group, a 3-isopropylbenzoyl group, a 4-isopropylbenzoyl group, a 2-butylbenzoyl group, a 3-butylbenzoyl group, a 4-butylbenzoyl group, a 2-isobutylbenzoyl group, a 3-isobutylbenzoyl group, a 4-isobutylbenzoyl group, a 2-sec-butylbenzoyl group, a 3-sec-butylbenzoyl group, a 4-sec-butylbenzoyl group, a 2-tert-butylbenzoyl group, a 3-tert-butylbenzoyl group, a 4-tert-butylbenzoyl group, a 2-pentylbenzoyl group, a 3-pentylbenzoyl group, a 4-pentylbenzoyl group, a 2-(2,2-dimethylpropyl)benzoyl group, a 3-(2,2-dimethylpropyl)benzoyl group, a 4-(2,2-dimethylpropyl)benzoyl group, a 2-(3-methylbutyl)benzoyl group, a 3-(3-methylbutyl)benzoyl group, a 4-(3-methylbutyl)benzoyl group, a 2-(2,3-dimethylbutyl)benzoyl group, a 3-(2,3-dimethylbutyl)benzoyl group, a 4-(2,3-dimethylbutyl)benzoyl group, a 2-(3,3-dimethylbutyl)benzoyl group, a 3-(3,3-dimethylbutyl)benzoyl group, a 4-(3,3-dimethylbutyl)benzoyl group, a 2-hexylbenzoyl group, a 3-hexylbenzoyl group, a 4-hexylbenzoyl group, a 2-trichloromethylbenzoyl group, a 3-trichloromethylbenzoyl group, a 4-trichloromethylbenzoyl group, a 2-difluoromethylbenzoyl group, a 3-difluoromethylbenzoyl group, a 4-difluoromethylbenzoyl group, a 2-trifluoromethylbenzoyl group, a 3-trifluoromethylbenzoyl group, a 4-trifluoromethylbenzoyl group, a 2-(2,2,2-trifluoroethyl)benzoyl group, a 3-(2,2,2-trifluoroethyl)benzoyl group, a 4-(2,2,2-trifluoroethyl)benzoyl group, a 2-pentafluoroethylbenzoyl group, a 3-pentafluoroethylbenzoyl group, a 4-pentafluoroethylbenzoyl group, a 2-heptafluoropropylbenzoyl group, a 3-heptafluoropropylbenzoyl group, a 4-heptafluoropropylbenzoyl group, a 2-heptafluoroisopropylbenzoyl group, a 3-heptafluoroisopropylbenzoyl group, a 4-heptafluoroisopropylbenzoyl group, a 2-methoxybenzoyl group, a 3-methoxybenzoyl group, a 4-methoxybenzoyl group, a 2-ethoxybenzoyl group, a 3-ethoxybenzoyl group, a 4-ethoxybenzoyl group, a 2-propoxybenzoyl group, a 3-propoxybenzoyl group, a 4-propoxybenzoyl group, a 2-isopropoxybenzoyl group, a 3-isopropoxybenzoyl group, a 4-isopropoxybenzoyl group, a 2-butoxybenzoyl group, a 3-butoxybenzoyl group, a 4-butoxybenzoyl group, a 2-isobutoxybenzoyl group, a 3-isobutoxybenzoyl group, a 4-isobutoxybenzoyl group, a 2-sec-butoxybenzoyl group, a 3-sec-butoxybenzoyl group, a 4-sec-butoxybenzoyl group, a 2-tert-butoxybenzoyl group, a 3-tert-butoxybenzoyl group, a 4-tert-butoxybenzoyl group, a 2-pentyloxybenzoyl group, a 3-pentyloxybenzoyl group, a 4-pentyloxybenzoyl group, a 2-(2,2-dimethylpropoxyl)benzoyl group, a 3-(2,2-dimethylpropoxyl)benzoyl group, a 4-(2,2-dimethylpropoxyl)benzoyl group, a 2-pentafluoroethoxybenzoyl group, a 3-pentafluoroethoxybenzoyl group, a 4-pentafluoroethoxybenzoyl group, a 2-heptafluoropropoxybenzoyl group, a 3-heptafluoropropoxybenzoyl group, a 4-heptafluoropropoxybenzoyl group, a 2-heptafluoroisopropoxybenzoyl group, a 3-heptafluoroisopropoxybenzoyl group, a 4-heptafluoroisopropoxybenzoyl group, a 2-(trifluoromethoxy)benzoyl group, a 3-(trifluoromethoxy)benzoyl group, a 4-(trifluoromethoxy)benzoyl group, and the like.

Examples of the "C2-C6 alkoxycarbonyl group" in the compound of the present invention include an methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, a 2,2-dimethylpropoxycarbonyl group, a 3-methylbutoxycarbonyl group, and the like.

Examples of the "C1-C6 alkyl group optionally having one or more halogen atoms" in the compound of the present invention include a methyl group, an ethyl group, a propyl group, an isopropyl group, a butyl group, an isobutyl group, a sec-butyl group, a tert-butyl group, a pentyl group, a 2,2-dimethylpropyl group, a 3-methylbutyl group, a 2,3-dimethylbutyl group, a 3,3-dimethylbutyl group, a hexyl group, a trichloromethyl group, a difluoromethyl group, a trifluoromethyl group, a 2,2,2-trifluoroethyl group, a pentafluoroethyl group, a heptafluoropropyl group, a heptafluoroisopropyl group, and the like.

Examples of the "C1-C6 alkyl group optionally having one or more groups selected from the group Z" in the compound of the present invention include a methyl group, an ethyl group, a propyl group, an isopropyl group, butyl group, an isobutyl group, a sec-butyl group, a tert-butyl group, a pentyl group, a 2,2-dimethylpropyl group, a 3-methylbutyl group, a 2,3-dimethylbutyl group, 3,3-dimethylbutyl group, a hexyl group, a trichloromethyl group, a difluoromethyl group, a trifluoromethyl group, a 2,2,2-trifluoroethyl group, a pentafluoroethyl group, a heptafluoropropyl group, a heptafluoroisopropyl group, a hydroxymethyl group, 2-hydroxyethyl group, a methoxymethyl group, a 2-methoxyethyl group, an ethoxymethyl group, a 2-ethoxyethyl group, a trifluoromethoxymethyl group, a 2,2,2-trifluoroethoxyethyl group, a methoxycarbonylmethyl group, and the like.

Examples of the "C3-C6 alkenyl group" in the compound of the present invention include an allyl group, a 1-methyl-2-propenyl group, a 2-methyl-2-propenyl group, a 2-butenyl group, a 3-butenyl group, a 2-pentenyl group, a 4-pentenyl group, a 2-hexenyl group, a 5-hexenyl group, and the like.

Examples of the "C3-C6 alkenyl group optionally having one or more groups selected from the group X" in the compound of the present invention include an allyl group, a 1-methyl-2-propenyl group, a 2-methyl-2-propenyl group, a 2-butenyl group, a 3-butenyl group, a 2-pentenyl group, a 4-pentenyl group, a 2-hexenyl group, a 5-hexenyl group, a 3,3-difluoro-2-propenyl group, a 3,3-dichloro-2-propenyl group, a 4-methoxy-2-methyl-2-butenyl group, a 3-cyano-2-butenyl group, and the like.

Examples of the "C3-C6 alkynyl group" in the compound of the present invention include a propargyl group, a 2-butynyl group, a 3-butynyl group, a 2-pentynyl group, a 4-pentynyl group, a 2-hexynyl group, a 5-hexynyl group, and the like.

Examples of the "C3-C6 alkynyl group optionally having one or more groups selected from the group X" in the compound of the present invention include a propargyl group, a 2-butynyl group, a 3-butynyl group, a 2-pentynyl group, a 2-hexynyl group, a 4-chloro-2-butynyl group, a 4-cyano-2-butynyl group, a 5-cyano-2-pentynyl group, a 4-methoxy-2-butynyl group, a 4-(2-chloroethoxy)-2-butynyl group, and the like.

Examples of the "C4-C7 cycloalkyl alkyl group" in the compound of the present invention include a cyclopropyl methyl group, a 1-cyclopropyl ethyl group, a 2-cyclopropyl ethyl group, a cyclobutyl methyl group, a 1-cyclobutyl ethyl group, a cyclopentyl methyl group, cyclohexyl methyl group, and the like.

Examples of the "C4-C7 cycloalkyl alkyl group optionally having one or more halogen atoms" in the compound of the present invention include a cyclopropyl methyl group, a 1-cyclopropyl ethyl group, a 2-cyclopropyl ethyl group, a cyclobutyl methyl group, a 1-cyclobutyl ethyl group, a cyclopentyl methyl group, a cyclohexyl methyl group, a (2,2-difluorocyclopropyl)methyl group, a 1-(2,2-dichlorocyclopropyl)ethyl group, a (2,2-dibromocyclobutyl)methyl group, a (2-chlorocyclopentyl)methyl group, and the like.

Examples of the "C3-C6 cycloalkyl group" in the compound of the present invention include a cyclopropyl group, a cyclobutyl group, a cyclopentyl group, a cyclohexyl group, and the like.

Examples of the "C3-C6 cycloalkyl group optionally having one or more halogen atoms" in the compound of the present invention include a cyclpropyl group, a cyclobutyl group, a cyclopentyl group, a cyclohexyl group, a 2,2-difluorocyclopropyl group, a 2,2-dichlorocyclopropyl group, a 2-chlorocyclopentyl group, a 4-iodocyclohexyl group, and the like.

Examples of the "C7-C9 phenylalkyl group" in the compound of the present invention include a benzyl group, a 1-phenylethyl group, a 2-phenylethyl group, a 1-phenylpropyl group, a 2-phenylpropyl group, a 3-phenylpropyl group, a 1-methyl-1-phenylethyl group, and the like.

Examples of the "C7-C9 phenylalkyl group in which a benzene ring portion may have optionally one or more groups selected from the group Y" in the compound of the present invention include a benzyl group, a 2-fluorobenzyl group, a 3-chlorobenzyl group, a 4-bromobenzyl group, a 2-cyanobenzyl group, a 3-nitrobenzyl group, a 3-methoxybenzyl group, a 4-trifluoromethylbenzyl group, a 4-trifluoromethoxybenzyl group, a 1-(3-chlorophenyl)ethyl group, a 2-(4-bromophenyl)ethyl group, a 1-(2-cyanophenyl)propyl group, a 2-(3-nitrophenyl)propyl group, a 3-(3-methoxyphenyl)propyl group, a 1-methyl-1-(4-trifluoromethoxyphenyl)ethyl group, and the like.

Examples of the "benzyl group in which a benzene ring portion may have optionally one or more groups selected from the group Y" in the compound of the present invention include a 2-fluorobenzyl group, a 3-chlorobenzyl group, a 4-bromobenzyl group, a 2-cyanobenzyl group, a 3-nitrobenzyl group, a 3-methoxybenzyl group, a 4-trifluoromethylbenzyl group, a 4-trifluoromethoxybenzyl group, and the like.

Examples of the "6-membered aromatic heterocyclic C1-C3 alkyl group" in the compound of the present invention include a 2-pyridylmethyl group, a 2-(2-pyridyl)ethyl group, a 1-(2-pyridyl)propyl group, a 3-pyridylmethyl group, a 4-pyridylmethyl group, a 3-pyridazinylmethyl group, a 2-pyrimidinylmethyl group, a 2-pyrazinylmethyl group, a 1-[4-(1,2,3-triazinyl)]ethyl group, and the like.

Examples of the "6-membered aromatic heterocyclic C1-C3 alkyl group in which a 6-membered aromatic heterocyclic portion may have optionally one or more groups selected from the group Y" in the compound of the present invention include a 2-pyridylmethyl group, a 3-fluoro-2-pyridylmethyl group, a 5-chloro-2-pyridylmethyl group, a 5-trifluoromethyl-2-pyridylmethyl group, a 2-(4-chloro-2-pyridyl)ethyl group, a 1-(5-bromo-2-pyridyl)propyl group, a 6-bromo-2-pyridylmethyl group, a 3-iodo-2-pyridylmethyl group, a 4-cyano-2-pyridylmethyl group, a 5-nitro-2-pyridylmethyl group, a 6-methyl-2-pyridylmethyl group, a 3-difluoromethyl-2-pyridylmethyl group, a 4-trifluoromethyl-2-pyridylmethyl group, a 3-pyridylmethyl group, a 6-chloro-3-pyridylmethyl group, a 4-pyridylmethyl group, a 2-chloro-4-pyridylmethyl group, a 4-methyl-3-pyridazinylmethyl group, a 6-difluoromethyl-3-pyridazinylmethyl group, a 4-trifluoromethyl-3-pyridazinylmethyl group, a 4-methyl-2-pyrimidinylmethyl group, a 5-difluoromethyl-2-pyrimidinylmethyl group, a 5-trifluoromethyl-2-pyrimidinylmethyl group, a 5-isopropyl-2-pyrazinylmethyl group, a 5-difluoromethyl-2-pyrazinylmethyl group, a 6-trifluoromethyl-2-pyrazinylmethyl group, a 3-(2,2,2-trifluoroethyl)-2-pyrazinylmethyl group, a 1-[5-tert-butyl-4-(1,2,3-triazinyl)]ethyl group, and the like.

The "C1-C4 alkyl group" in the compound of the present invention include a methyl group, an ethyl group, a propyl group, an isopropyl group, a butyl group, an isobutyl group, a sec-butyl group, and a tert-butyl group.

Examples of the "C1-C4 alkyl group optionally having one or more halogen atoms" in the compound of the present invention include a methyl group, an ethyl group, a propyl group, an isopropyl group, a butyl group, an isobutyl group, a sec-butyl group, a tert-butyl group, a trichloromethyl group, a difluoromethyl group, a trifluoromethyl group, a 2,2,2-trifluoroethyl group, a pentafluoroethyl group, a heptafluoropropyl group, a heptafluoroisopropyl group, and the like.

Examples of the "C1-C4 alkylsulfonyl group" in the compound of the present invention include a methylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group, and the like.

Examples of the "C1-C4 alkylsulfonyl group optionally having one or more halogen atoms" in the compound of the present invention include a methylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group, a trichloromethylsulfonyl group, a difluoromethylsulfonyl group, a trifluoromethylsulfonyl group, a 2,2,2-trifluoroethylsulfonyl group, and the like.

Examples of the "phenylsulfonyl group optionally having one or more groups selected from the group Y" in the compound of the present invention include a 2-fluorophenylsulfonyl group, a 3-chlorophenylsulfonyl group, a 4-chlorophenylsulfonyl group, a 2-iodophenylsulfonyl group, a 3-cyanophenylsulfonyl group, a 4-nitrophenylsulfonyl group, a 2-methylphenylsulfonyl group, a 4-methylphenylsulfonyl group, a 4-tert-butylphenylsulfonyl group, a 4-difluoromethylphenylsulfonyl group, a 2-trifluoromethylphenylsulfonyl group, a 2-(2,2,2-trifluoroethyl)phenylsulfonyl group, a 4-pentafluoroethylphenylsulfonyl group, a 4-heptafluoroisopropylphenylsulfonyl group, a 2-methoxyphenylsulfonyl group, a 3-difluoromethoxyphenylsulfonyl group, a 4-difluoromethoxyphenylsulfonyl group, a 2-trifluoromethoxyphenylsulfonyl group, a 4-(2,2,2-trifluoroethoxyl)phenylsulfonyl group, and the like.

Examples of the "C7-C9 phenylalkylsulfonyl group" in the compound of the present invention include a benzylsulfonyl group, a 1-phenylethylsulfonyl group, a 2-phenylethylsulfonyl group, a 1-phenylpropylsulfonyl group, a 2-phenylpropylsulfonyl group, a 3-phenylpropylsulfonyl group, a 1-methyl-1-phenylethylsulfonyl group, and the like.

Examples of the "C7-C9 phenylalkylsulfonyl group in which a benzene ring portion may have optionally one or more groups selected from the group Y" in the compound of the present invention include a 2-fluorobenzylsulfonyl group, a 3-chlorobenzylsulfonyl group, a 4-bromobenzylsulfonyl group, a 2-cyanobenzylsulfonyl group, a 3-nitrobenzylsulfonyl group, a 3-methoxybenzylsulfonyl group, a 4-trifluoromethoxybenzylsulfonyl group, a 1-(3-chlorophenyl)ethylsulfonyl group, a 2-(4-bromophenyl)ethylsulfonyl group, a 1-(2-cyanophenyl)propylsulfonyl group, a 2-(3-nitrophenyl)propylsulfonyl group, a 3-(3-methoxyphenyl)propylsulfonyl group, a 1-methyl-1-(4-trifluoromethoxyphenyl)ethylsulfonyl group, and the like.

Examples of the "C1-C6 alkoxy group" in the compound of the present invention include a methoxy group, an ethoxy group, a propoxy group, an isopropoxy group, a butoxy group, an isobutoxy group, a sec-butoxy group, a tert-butoxy group, a pentyloxy group, a 2,2-dimethylpropoxy group, a 3-methylbutoxy group, a 2,3-dimethylbutoxy group, a 3,3-dimethylbutoxy group, a hexyloxy group, and the like.

Examples of the "C1-C6 alkoxy group optionally having one or more halogen atoms" in the compound of the present invention include a methoxy group, an ethoxy group, a propoxy group, an isopropoxy group, a butoxy group, an isobutoxy group, a sec-butoxy group, a tert-butoxy group, a pentyloxy group, a 2,2-dimethylpropoxy group, a 3-methylbutoxy group, a 2,3-dimethylbutoxy group, a 3,3-dimethylbutoxy group, a hexyloxy group, a trichloromethoxy group, a difluoromethoxy group, a trifluoromethoxy group, a 2,2,2-trifluoroethoxy group, a pentafluoroethoxy group, a heptafluoropropoxy group, a heptafluoroisopropoxy group, and the like.

Examples of the compound of the present invention include the following.

A compound represented by Formula (1) in which $R^1$ represents —C(O)W substituted at position 3;

a compound represented by Formula (1) in which $R^1$ represents —C(O)W substituted at position 4;

a compound represented by Formula (1) in which $R^1$ represents —C(O)W substituted at position 5;

a compound represented by Formula (1) in which $R^1$ represents —C(O)W substituted at position 6;

a compound represented by Formula (1) in which $R^1$ represents —C(O)W substituted at position 7;

a compound represented by Formula (1) in which W represents —ON=$CR^4R^5$;

a compound represented by Formula (1) in which W represents —$OR^6$;

a compound represented by Formula (1) in which W represents —$SR^7$;

a compound represented by Formula (1) in which W represents —$NR^4R^8$;

a compound represented by Formula (1) in which W represents —ON=$CR^4R^5$ or —$OR^6$;

a compound represented by Formula (1) in which W represents —$OR^6$ or —$SR^7$;

a compound represented by Formula (1) in which W represents —$OR^6$ or —$NR^4R^8$;

a compound represents Formula (1) in which $R^2$ represents a cyano group, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocabonyl group, —$NR^9R^{10}$, —$S(O)_2NR^4R^9$, —$OR^9$, —$S(O)_mR^9$, or —$SF_5$, substituted at position 3;

a compound represents Formula (1) in which $R^2$ represents a halogen atom, a C1-C6 alkyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkoxycarbonyl group, an aminocabonyl group, —$NR^9R^{10}$, —$S(O)_2NR^4R^9$, or —$OR^9$, substituted at position 3;

a compound represented by Formula (1) in which $R^2$ represents a halogen atom, a C1-C6 alkyl group optionally having one or more groups selected from the group X, a phenyl group optionally having one or more groups selected from the group Y, or —$OR^9$, substituted at position 3;

a compound represented by Formula (1) in which $R^2$ represents a halogen atom, a methyl group, an ethyl group, a trifluoromethyl group, a difluoromethyl group, a phenyl group optionally having one or more groups selected from the group Y, a methoxy group, a trifluoromethoxy group, or a difluoromethoxy group, substituted at position 3;

a compound represented by Formula (1) in which $R^2$ represents a halogen atom, a methyl group, trifluoromethyl group, a difluoromethyl group, or a phenyl group optionally having one or more groups selected from the group Y, substituted at position 3;

a compound represented by Formula (1) in which $R^2$ represents a carboxy group, an aminocabonyl group, or a methoxycarbonyl group, substituted at position 3;

a compound represented by Formula (1) in which $R^2$ represents a cyano group, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocabonyl group, —$NR^9R^{10}$, —$S(O)_2NR^4R^9$, —$OR^9$, —$S(O)_mR^9$, or —$SF_5$, substituted at position 4;

a compound represented by Formula (1) in which $R^2$ represents a cyano group, a halogen atom, a nitro group, a C1-C6 alkyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkoxycarbonyl group, an aminocabonyl group, —$NR^9R^{10}$, —$S(O)_2NR^4R^9$, $OR^9$, —$S(O)_mR^9$, or —$SF_5$, substituted at position 4;

a compound represented by Formula (1) in which $R^2$ represents a cyano group, a halogen atom, a nitro group, a C1-C6 alkyl group optionally having one or more groups selected from the group X, a C2-C6 alkoxycarbonyl group, a phenyl group optionally having one or more groups selected from the group Y, a carboxy group, an aminocabonyl group, —OR$^9$, or —S(O)$_m$R$^9$, substituted at position 4;

a compound represented by Formula (1) in which R$^2$ represents a cyano group, a halogen atom, a nitro group, methyl group, an ethyl group, a trifluoromethyl group, a difluoromethyl group, a phenyl group optionally having one or more groups selected from the group Y, a carboxy group, a methoxycarbonyl group, an aminocabonyl group, a methoxy group, a trifluoromethoxy group, a difluoromethoxy group, a methylthio group, a methylsulfinyl group, a methylsulfonyl group, a trifluoromethylthio group, a trifluoromethylsulfinyl group, or a trifluoromethylsulfonyl group, substituted at position 4;

a compound represented by Formula (1) in which R$^2$ represents a cyano group, a halogen atom, a nitro group, a methyl group, a trifluoromethyl group, a difluoromethyl group, a phenyl group optionally having one or more groups selected from the group Y, carboxy group, a methoxycarbonyl group, an aminocabonyl group, a methoxy group, a trifluoromethoxy group, or a difluoromethoxy group, substituted at position 4;

a compound represented by Formula (1) in which R$^2$ represents a cyano group, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocabonyl group, —NR$^9$R$^{10}$, —S(O)$_2$NR$^4$R$^9$, —OR$^9$, —S(O)$_m$R$^9$, or —SF$_5$, substituted at position 5;

a compound represented by Formula (1) in which R$^2$ represents a cyano group, a halogen atom, a nitro group, a C1-C6 alkyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkoxycarbonyl group, an aminocabonyl group, —NR$^9$R$^{10}$, —S(O)$_2$NR$^4$R$^9$, —OR$^9$, —S(O)$_m$R$^9$, or —SF$_5$, substituted at position 5;

a compound represented by Formula (1) in which R$^2$ represents a cyano group, a halogen atom, a nitro group, a C1-C6 alkyl group optionally having one or more groups selected from the group X, a phenyl group optionally having one or more groups selected from the group Y, a carboxy group, an aminocabonyl group, —OR$^9$, or —S(O)$_m$R$^9$, substituted at position 5;

a compound represented by Formula (1) in which R$^2$ represents a cyano group, a halogen atom, a nitro group, a methyl group, an ethyl group, a trifluoromethyl group, a difluoromethyl group, a phenyl group optionally having one or more groups selected from the group Y, an aminocabonyl group, a methoxy group, a trifluoromethoxy group, a difluoromethoxy group, a methylthio group, a methylsulfinyl group, a methylsulfonyl group, a trifluoromethylthio group, a trifluoromethylsulfinyl group, or a trifluoromethylsulfonyl group, substituted at position 5;

a compound represented by Formula (1) in which R$^2$ represents a cyano group, a halogen atom, a nitro group, a methyl group, a trifluoromethyl group, a difluoromethyl group, a phenyl group optionally having one or more groups selected from the group Y, a carboxy group, an aminocabonyl group, a methoxy group, a trifluoromethoxy group, or a difluoromethoxy group, substituted at position 5;

a compound represented by Formula (1) in which R$^2$ represents a cyano group, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocabonyl group, —NR$^9$R$^{10}$, —S(O)$_2$NR$^4$R$^9$, —OR$^9$, —S(O)$_m$R$^9$, or —SF$_5$, substituted at position 6;

a compound represented by Formula (1) in which R$^2$ represents a cyano group, a halogen atom, a nitro group, a C1-C6 alkyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkoxycarbonyl group, an aminocabonyl group, —NR$^9$R$^{10}$, —S(O)$_2$NR$^4$R$^9$, —OR$^9$, —S(O)$_m$R$^9$, or —SF$_5$, substituted at position 6;

a compound represented by Formula (1) in which R$^2$ represents a cyano group, a halogen atom, a nitro group, a C1-C6 alkyl group optionally having one or more groups selected from the group X, a phenyl group optionally having one or more groups selected from the group Y, an aminocabonyl group, —OR$^9$, or —S(O)$_m$R$^9$, substituted at position 6;

a compound represented by Formula (1) in which R$^2$ represents a cyano group, a halogen atom, a nitro group, a methyl group, an ethyl group, a trifluoromethyl group, a difluoromethyl group, a phenyl group optionally having one or more groups selected from the group Y, an aminocabonyl group, a methoxy group, a trifluoromethoxy group, a difluoromethoxy group, a methylthio group, a methylsulfinyl group, a methylsulfonyl group, a trifluoromethylthio group, a trifluoromethylsulfinyl group, or a trifluoromethylsulfonyl group, substituted at position 6;

a compound represented by Formula (1) in which R$^2$ represents a cyano group, a halogen atom, a nitro group, methyl group, a trifluoromethyl group, a difluoromethyl group, a phenyl group optionally having one or more groups selected from the group Y, an aminocabonyl group, a methoxy group, a trifluoromethoxy group, or a difluoromethoxy group, substituted at position 6;

a compound represented by Formula (1) in which R$^2$ represents a cyano group, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocabonyl group, —NR$^9$R$^{10}$, —S(O)$_2$NR$^4$R$^9$, —OR$^9$, —S(O)$_m$R$^9$, or —SF$_5$, substituted at position 7;

a compound represented by Formula (1) in which R$^2$ represents a cyano group, a halogen atom, a nitro group, a C1-C6 alkyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkoxycarbonyl group, an aminocabonyl group, —NR$^9$R$^{10}$, —S(O)$_2$NR$^4$R$^9$, —OR$^9$, —S(O)$_m$R$^9$, or —SF$_5$, substituted at position 7;

a compound represented by Formula (1) in which R$^2$ represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, an aminocabonyl group, —OR$^9$, or —S(O)$_m$R$^9$, substituted at position 7;

a compound represented by Formula (1) in which R$^2$ represents a cyano group, a halogen atom, a nitro group, a methyl group, an ethyl group, a trifluoromethyl group, a difluoromethyl group, a phenyl group optionally having one or more groups selected from the group Y, an aminocabonyl group, a methoxy group, a trifluoromethoxy group, a difluoromethoxy group, a methylthio group, a methylsulfinyl group, a methylsulfonyl group, a trifluoromethylthio group, a trifluoromethylsulfinyl group, or a trifluoromethylsulfonyl group, substituted at position 7;

a compound represented by Formula (1) in which R$^2$ represents a cyano group, a halogen atom, a nitro group, a methyl group, a trifluoromethyl group, a difluoromethyl group, a phenyl group optionally having one or more groups selected from the group Y, a carboxy group, a methoxycarbonyl group, an aminocabonyl group, a methoxy group, a trifluoromethoxy group, or a difluoromethoxy group, substituted at position 7;

a compound represented by Formula (1) in which R$^2$ represents a cyano group;

a compound represented by Formula (1) in which R$^2$ represents a halogen atom;

a compound represented by Formula (1) in which R$^2$ represents a nitro group;

a compound represented by Formula (1) in which R$^2$ represents a C1-C6 alkyl group;

a compound represented by Formula (1) in which R$^2$ represents a C1-C6 alkyl group optionally having one or more groups selected from the group X;

a compound represented by Formula (1) in which R$^2$ represents a C2-C6 alkenyl group;

a compound represented by Formula (1) in which R$^2$ represents a C2-C6 alkenyl group optionally having one or more groups selected from the group X;

a compound represented by Formula (1) in which R$^2$ represents a C2-C6 alkynyl group;

a compound represented by Formula (1) in which R$^2$ represents a C2-C6 alkynyl group optionally having one or more groups selected from the group X;

a compound represented by Formula (1) in which R$^2$ represents a phenyl group;

a compound represented by Formula (1) in which R$^2$ represents a phenyl group optionally having one or more groups selected from the group Y;

a compound represented by Formula (1) in which R$^2$ represents a 6-membered aromatic heterocyclic group;

a compound represented by Formula (1) in which R$^2$ represents a 6-membered aromatic heterocyclic group optionally having one or more groups selected from the group Y;

a compound represented by Formula (1) in which R$^2$ represents a 5-membered aromatic heterocyclic group;

a compound represented by Formula (1) in which R$^2$ represents a 5-membered aromatic heterocyclic group optionally having one or more groups selected from the group Y;

a compound represented by Formula (1) in which R$^2$ represents a carboxy group;

a compound represented by Formula (1) in which R$^2$ represents a C2-C6 alkylcarbonyl group;

a compound represented by Formula (1) in which R$^2$ represents a C2-C6 alkylcarbonyl group optionally having one or more halogen atoms;

a compound represented by Formula (1) in which R$^2$ represents a benzoyl group;

a compound represented by Formula (1) in which R$^2$ represents a benzoyl group optionally having one or more groups selected from the group Y;

a compound represented by Formula (1) in which R$^2$ represents a C2-C6 alkoxycarbonyl group;

a compound represented by Formula (1) in which R$^2$ represents an aminocabonyl group;

a compound represented by Formula (1) in which R$^2$ represents —NR$^9$R$^{10}$; a compound represented by Formula (1) in which R$^2$ represents —S(O)$_2$NR$^4$R$^9$;

a compound represented by Formula (1) in which R$^2$ represents —OR$^9$;

a compound represented by Formula (1) in which R$^2$ represents —S(O)$_m$R$^9$;

a compound represented by Formula (1) in which R$^2$ represents —SF$_5$;

a compound represented by Formula (1) in which R$^3$ represents a hydrogen atom;

a compound represented by Formula (1) in which R$^3$ represents a halogen atom;

a compound represented by Formula (1) in which R$^3$ represents a cyano group;

a compound represented by Formula (1) in which R$^3$ represents a nitro group;

a compound represented by Formula (1) in which R$^3$ represents C1-C6 alkyl group;

a compound represented by Formula (1) in which R$^3$ represents a C1-C6 alkyl group optionally having one or more groups selected from the group X;

a compound represented by Formula (1) in which R$^3$ represents a C2-C6 alkenyl group;

a compound represented by Formula (1) in which R$^3$ represents a C2-C6 alkenyl group optionally having one or more groups selected from the group X;

a compound represented by Formula (1) in which R$^3$ represents a C2-C6 alkynyl group;

a compound represented by Formula (1) in which $R^3$ represents a C2-C6 alkynyl group optionally having one or more groups selected from the group X;

a compound represented by Formula (1) in which $R^3$ represents a C2-C6 alkylcarbonyl group;

a compound represented by Formula (1) in which $R^3$ represents a C2-C6 alkylcarbonyl group optionally having one or more halogen atoms;

a compound represented by Formula (1) in which $R^3$ represents a benzoyl group;

a compound represented by Formula (1) in which $R^3$ represents a benzoyl group optionally having one or more groups selected from the group Y;

a compound represented by Formula (1) in which $R^3$ represents —$NR^9R^{10}$;

a compound represented by Formula (1) in which $R^3$ represents —$S(O)_2NR^4R^9$;

a compound represented by Formula (1) in which $R^3$ represents —$OR^9$;

a compound represented by Formula (1) in which $R^3$ represents —$S(O)_mR^9$;

a compound represented by Formula (1) in which W represents —$ON=CR^4R^5$, and $R^4$ represents a hydrogen atom;

a compound represented by Formula (1) in which W represents —$ON=CR^4R^5$, and $R^4$ represents a C1-C6 alkyl group;

a compound represented by Formula (1) in which W represents —$ON=CR^4R^5$, and $R^4$ represents a C1-C6 alkyl group optionally having one or more halogen atoms;

a compound represented by Formula (1) in which W represents —$ON=CR^4R^5$, and $R^4$ represents a phenyl group;

a compound represented by Formula (1) in which W represents —$ON=CR^4R^5$, and $R^4$ represents a phenyl group optionally having one or more groups selected from the group Y;

a compound represented by Formula (1) in which W represents —$ON=CR^4R^5$, $R^4$ represents a hydrogen atom, and $R^5$ represents a C1-C6 alkyl group;

a compound represented by Formula (1) in which W represents —$ON=CR^4R^5$, $R^4$ represents a hydrogen atom, and $R^5$ represents a C1-C6 alkyl group optionally having one or more halogen atoms;

a compound represented by Formula (1) in which W represents —$ON=CR^4R^5$, $R^4$ represents a hydrogen atom, and $R^5$ represents a phenyl group;

a compound represented by Formula (1) in which W represents —$ON=CR^4R^5$, $R^4$ represents a hydrogen atom, and $R^5$ represents a phenyl group optionally having one or more groups selected from the group Y;

a compound represented by Formula (1) in which W represents —$ON=CR^4R^5$, $R^4$ and $R^5$ represent a C1-C6 alkyl group optionally having one or more halogen atoms;

a compound represented by Formula (1) in which W represents —$ON=CR^4R^5$, $R^4$ represents a C1-C6 alkyl group optionally having one or more halogen atoms, and $R^5$ represents a phenyl group optionally having one or more groups selected from the group Y;

a compound represented by Formula (1) in which W represents —$ON=CR^4R^5$, $R^4$ and $R^5$ represent a C1-C6 alkyl group;

a compound represented by Formula (1) in which W represents —$ON=CR^4R^5$, $R^4$ represents a C1-C6 alkyl group, and $R^5$ represents a phenyl group optionally having one or more groups selected from the group Y;

a compound represented by Formula (1) in which W represents —$ON=CR^4R^5$, $R^4$ and $R^5$ represent a phenyl group optionally having one or more groups selected from the group Y;

a compound represented by Formula (1) in which W represents —$ON=CR^4R^5$, $R^4$ and $R^5$ represent a phenyl group;

a compound represented by Formula (1) in which W represents —$NR^4R^8$, and $R^4$ represents a hydrogen atom;

a compound represented by Formula (1) in which W represents —$NR^4R^8$, and $R^4$ represents a C1-C6 alkyl group;

a compound represented by Formula (1) in which W represents —$NR^4R^8$, and $R^4$ represents a C1-C6 alkyl group optionally having one or more halogen atoms;

a compound represented by Formula (1) in which W represents —$NR^4R^8$, and $R^4$ represents a phenyl group;

a compound represented by Formula (1) in which W represents —$NR^4R^8$, and $R^4$ represents a phenyl group optionally having one or more groups selected from the group Y;

a compound represented by Formula (1) in which W represents —$NR^4R^8$, and $R^8$ represents a hydrogen atom;

a compound represented by Formula (1) in which W represents —$NR^4R^8$, and $R^8$ represents a cyano group; a compound represented by Formula (1) in which W represents —$NR^4R^8$, and $R^8$ represents C1-C6 alkyl group optionally having one or more groups selected from the group Z;

a compound represented by Formula (1) in which W represents —$NR^4R^8$, and $R^8$ represents a C1-C6 alkyl group;

a compound represented by Formula (1) in which W represents —$NR^4R^8$, and $R^8$ represents a phenyl group optionally having one or more groups selected from the group Y;

a compound represented by Formula (1) in which W represents —$NR^4R^8$, and $R^8$ represents a benzyl group in which a benzene ring portion may have optionally one or more groups selected from the group Y;

a compound represented by Formula (1) in which W represents —$NR^4R^8$, and $R^8$ represents —$OR^4$;

a compound represented by Formula (1) in which W represents —$NR^4R^8$, and $R^8$ represents —$NR^4R^5$;

a compound represented by Formula (1) in which W represents —$NR^4R^8$, and $R^4$ and $R^8$ represent a hydrogen atom;

a compound represented by Formula (1) in which W represents —$NR^4R^8$, and $R^4$ represents a hydrogen atom, and $R^8$ represents a cyano group;

a compound represented by Formula (1) in which W represents —$NR^4R^8$, and $R^4$ represents a hydrogen atom, and $R^8$ represents a C1-C6 alkyl group optionally having one or more groups selected from the group Z;

a compound represented by Formula (1) in which W represents —$NR^4R^8$, and $R^4$ represents a hydrogen atom, and $R^8$ represents a C1-C6 alkyl group;

a compound represented by Formula (1) in which W represents —$NR^4R^8$, and $R^4$ represents a hydrogen atom, and $R^8$ represents a phenyl group optionally having one or more groups selected from the group Y;

a compound represented by Formula (1) in which W represents —$NR^4R^8$, and $R^4$ represents a hydrogen atom, and $R^8$ represents a benzyl group in which a benzene ring portion may have optionally one or more groups selected from the group Y;

a compound represented by Formula (1) in which W represents —$NR^4R^8$, and $R^4$ represents a hydrogen atom, and $R^8$ represents —$OR^4$;

a compound represented by Formula (1) in which W represents —NR$^4$R$^8$, and R$^4$ represents a hydrogen atom, and R$^8$ represents —NR$^4$R$^5$;

a compound represented by Formula (1) in which W represents —NR$^4$R$^8$, and R$^4$ represents a hydrogen atom, and R$^8$ represents —OH;

a compound represented by Formula (1) in which W represents —NR$^4$R$^8$, and R$^4$ represents a hydrogen atom, and R$^8$ represents —NH$_2$;

a compound represented by Formula (1) in which W represents —NR$^4$R$^8$, R$^4$ represents a C1-C6 alkyl group optionally having one or more halogen atoms, and R$^8$ represents a C1-C6 alkyl group optionally having one or more groups selected from the group Z;

a compound represented by Formula (1) in which W represents —OR$^6$, and R$^6$ represents a hydrogen atom, a C1-C6 alkyl group optionally having one or more groups selected from the group Z, a C3-C6 alkenyl group optionally having one or more groups selected from the group X, a C3-C6 alkynyl group optionally having one or more groups selected from the group X, a C4-C7 cycloalkylalkyl group optionally having one or more halogen atoms, a C3-C6 cycloalkyl group optionally having one or more halogen atoms, a phenyl group optionally having one or more groups selected from the group Y, or a C7-C9 phenylalkyl group in which a benzene ring portion may have optionally one or more groups selected from the group Y;

a compound represented by Formula (1) in which W represents —OR$^6$, and R$^6$ represents a hydrogen atom, a C1-C6 alkyl group optionally having one or more groups selected from the group Z, a C3-C6 alkenyl group optionally having one or more groups selected from the group X, or a phenyl group optionally having one or more groups selected from the group Y;

a compound represented by Formula (1) in which W represents —OR$^6$, and R$^6$ represents a hydrogen atom, a C1-C6 alkyl group optionally having one or more groups selected from the group Z, or a phenyl group optionally having one or more groups selected from the group Y;

a compound represented by Formula (1) in which W represents —OR$^6$, and R$^6$ represents a hydrogen atom or a C1-C6 alkyl group optionally having one or more groups selected from the group Z;

a compound represented by Formula (1) in which W represents —OR$^6$, and R$^6$ represents a hydrogen atom;

a compound represented by Formula (1) in which W represents —OR$^6$, and R$^6$ represents a C1-C6 alkyl group optionally having one or more groups selected from the group Z;

a compound represented by Formula (1) in which W represents —OR$^6$, and R$^6$ represents a C1-C6 alkyl group optionally having one or more halogen atoms;

a compound represented by Formula (1) in which W represents —OR$^6$, and R$^6$ represents a C1-C6 alkyl group;

a compound represented by Formula (1) in which W represents —OR$^6$, and R$^6$ represents a methyl group or an ethyl group;

a compound represented by Formula (1) in which W represents —OR$^6$, and R$^6$ represents a methyl group;

a compound represented by Formula (1) in which W represents —SR$^7$, and R$^7$ represents a hydrogen atom, a C1-C6 alkyl group optionally having one or more groups selected from the group X, a C3-C6 alkenyl group optionally having one or more groups selected from the group X, a C3-C6 alkynyl group optionally having one or more groups selected from the group X, and a phenyl group optionally having one or more groups selected from the group Y;

a compound represented by Formula (1) in which W represents —SR$^7$, and R$^7$ represents a hydrogen atom, a C1-C6 alkyl group optionally having one or more groups selected from the group X, or a phenyl group optionally having one or more groups selected from the group Y;

a compound represented by Formula (1) in which W represents —SR$^7$, and R$^7$ represents a hydrogen atom or a C1-C6 alkyl group optionally having one or more groups selected from the group X;

a compound represented by Formula (1) in which W represents —SR$^7$, and R$^7$ represents a hydrogen atom;

a compound represented by Formula (1) in which W represents —SR$^7$, and R$^7$ represents a C1-C6 alkyl group optionally having one or more groups selected from the group X;

a compound represented by Formula (1) in which W represents —SR$^7$, and R$^7$ represents a C1-C6 alkyl group optionally having one or more halogen atoms;

a compound represented by Formula (1) in which W represents —SR$^7$, and R$^7$ represents a C1-C6 alkyl group;

a compound represented by Formula (1) in which W represents —SR$^7$, and R$^7$ represents a methyl group or an ethyl group;

a compound represented by Formula (1) in which W represents —SR$^7$, and R$^7$ represents a methyl group;

a compound represented by Formula (1) in which n represents 0, 1, 2, or 3;

a compound represented by Formula (1) in which n represents 0, 1, or 2;

a compound represented by Formula (1) in which n represents 0 or 1;

a compound represented by Formula (1) in which n represents 2;

a compound represented by Formula (1) in which n represents 1;

a compound represented by Formula (1) in which n represents 0;

a compound represented by Formula (1) in which n represents 0, and R$^3$ represents a hydrogen atom;

a compound represented by Formula (1) in which n represents 0, and R$^3$ represents a C1-C6 alkyl group optionally having one or more groups selected from the group X;

a compound represented by Formula (1) in which n represents 0, and R$^3$ represents a trifluoromethyl group;

a compound represented by Formula (1) in which R$^2$ represents a fluorine atom;

a compound represented by Formula (1) in which R$^2$ represents a chlorine atom;

a compound represented by Formula (1) in which R$^2$ represents a bromine atom;

a compound represented by Formula (1) in which R$^2$ represents an iodine atom;

a compound represented by Formula (1) in which R$^2$ represents a methyl group;

a compound represented by Formula (1) in which R$^2$ represents an ethyl group;

a compound represented by Formula (1) in which R$^2$ represents an isopropyl group;

a compound represented by Formula (1) in which R$^2$ represents a tert-butyl group;

a compound represented by Formula (1) in which R$^2$ represents a difluoromethyl group;

a compound represented by Formula (1) in which R$^2$ represents a trifluoromethyl group;

a compound represented by Formula (1) in which R$^2$ represents a pentafluoroethyl group;

a compound represented by Formula (1) in which $R^2$ represents a heptafluoropropyl group;

a compound represented by Formula (1) in which $R^2$ represents a heptafluoroisopropyl group;

a compound represented by Formula (1) in which $R^2$ represents a methoxycarbonyl group;

a compound represented by Formula (1) in which $R^2$ represents an ethoxycarbonyl group;

a compound represented by Formula (1) in which $R^2$ represents a methoxy group;

a compound represented by Formula (1) in which $R^2$ represents an ethoxy group;

a compound represented by Formula (1) in which $R^2$ represents a difluoromethoxy group;

a compound represented by Formula (1) in which $R^2$ represents a trifluoromethoxy group;

a compound represented by Formula (1) in which $R^2$ represents a methylthio group;

a compound represented by Formula (1) in which $R^2$ represents a methylsulfinyl group;

a compound represented by Formula (1) in which $R^2$ represents a methylsulfonyl group;

a compound represented by Formula (1) in which $R^2$ represents a trifluoromethylthio group;

a compound represented by Formula (1) in which $R^2$ represents a trifluoromethylsulfinyl group;

a compound represented by Formula (1) in which $R^2$ represents a trifluoromethylsulfonyl group;

a compound represented by Formula (1) in which $R^2$ represents a pyridyl group;

a compound represented by Formula (1) in which $R^2$ represents a pyrimidinyl group;

a compound represented by Formula (1) in which $R^2$ represents a thienyl group;

a compound represented by Formula (1) in which $R^2$ represents a phenoxy group;

a compound represented by Formula (1) in which $R^2$ represents a phenylthio group;

a compound represented by Formula (1) in which $R^2$ represents an amino group;

a compound represented by Formula (1) in which $R^2$ represents an acetyl group;

a compound represented by Formula (1) in which $R^2$ represents a trifluoroacetyl group;

a compound represented by Formula (1) in which $R^3$ represents a chlorine atom;

a compound represented by Formula (1) in which $R^3$ represents a bromine atom;

a compound represented by Formula (1) in which $R^3$ represents a methyl group;

a compound represented by Formula (1) in which $R^3$ represents an ethyl group;

a compound represented by Formula (1) in which $R^3$ represents an isopropyl group;

a compound represented by Formula (1) in which $R^3$ represents a tert-butyl group;

a compound represented by Formula (1) in which $R^3$ represents a difluoromethyl group;

a compound represented by Formula (1) in which $R^3$ represents a trifluoromethyl group;

a compound represented by Formula (1) in which $R^3$ represents a pentafluoroethyl group;

a compound represented by Formula (1) in which $R^3$ represents a heptafluoropropyl group;

a compound represented by Formula (1) in which $R^3$ represents heptafluoroisopropyl group;

a compound represented by Formula (1) in which $R^3$ represents a cyano group;

a compound represented by Formula (1) in which $R^3$ represents an acetyl group;

a compound represented by Formula (1) in which $R^3$ represents an ethylcarbonyl group;

a compound represented by Formula (1) in which $R^3$ represents a trifluoroacetyl group;

a compound represented by Formula (1) in which $R^3$ represents a difluoroacetyl group;

a compound represented by Formula (1) in which $R^2$ represents a fluorine atom, and $R^3$ represents a hydrogen atom;

a compound represented by Formula (1) in which $R^2$ represents a chlorine atom, and $R^3$ represents a hydrogen atom;

a compound represented by Formula (1) in which $R^2$ represents a bromine atom, and $R^3$ represents a hydrogen atom;

a compound represented by Formula (1) in which $R^2$ represents an iodine atom, and $R^3$ represents a hydrogen atom;

a compound represented by Formula (1) in which $R^2$ represents a methyl group, and $R^3$ represents a hydrogen atom;

a compound represented by Formula (1) in which $R^2$ represents an ethyl group, and $R^3$ represents a hydrogen atom;

a compound represented by Formula (1) in which $R^2$ represents an isopropyl group, and $R^3$ represents a hydrogen atom;

a compound represented by Formula (1) in which $R^2$ represents a tert-butyl group, and $R^3$ represents a hydrogen atom;

a compound represented by Formula (1) in which $R^2$ represents a difluoromethyl group, and $R^3$ represents a hydrogen atom;

a compound represented by Formula (1) in which $R^2$ represents a trifluoromethyl group, and $R^3$ represents a hydrogen atom;

a compound represented by Formula (1) in which $R^2$ represents a pentafluoroethyl group, and $R^3$ represents a hydrogen atom;

a compound represented by Formula (1) in which $R^2$ represents a heptafluoropropyl group, and $R^3$ represents a hydrogen atom;

a compound represented by Formula (1) in which $R^2$ represents a heptafluoroisopropyl group, and $R^3$ represents a hydrogen atom;

a compound represented by Formula (1) in which $R^2$ represents a methoxycarbonyl group, and $R^3$ represents a hydrogen atom;

a compound represented by Formula (1) in which $R^2$ represents an ethoxycarbonyl group, and $R^3$ represents a hydrogen atom;

a compound represented by Formula (1) in which $R^2$ represents an aminocabonyl group, and $R^3$ represents a hydrogen atom;

a compound represented by Formula (1) in which $R^2$ represents a methoxy group, and $R^3$ represents a hydrogen atom;

a compound represented by Formula (1) in which $R^2$ represents an ethoxy group, and $R^3$ represents a hydrogen atom;

a compound represented by Formula (1) in which $R^2$ represents a difluoromethoxy group, and $R^3$ represents a hydrogen atom;

a compound represented by Formula (1) in which $R^2$ represents a trifluoromethoxy group, and $R^3$ represents a hydrogen atom;

a compound represented by Formula (1) in which $R^2$ represents a methylthio group, and $R^3$ represents a hydrogen atom;

a compound represented by Formula (1) in which $R^2$ represents a methylsulfinyl group, and $R^3$ represents a hydrogen atom;

a compound represented by Formula (1) in which $R^2$ represents a methylsulfonyl group, and $R^3$ represents hydrogen atom;

a compound represented by Formula (1) in which $R^2$ represents a trifluoromethylthio group, and $R^3$ represents a hydrogen atom;

a compound represented by Formula (1) in which $R^2$ represents a trifluoromethylsulfinyl group, and $R^3$ represents a hydrogen atom;

a compound represented by Formula (1) in which $R^2$ represents a trifluoromethylsulfonyl group, and $R^3$ represents a hydrogen atom;

a compound represented by Formula (1) in which $R^2$ represents a phenyl group, and $R^3$ represents a hydrogen atom;

a compound represented by Formula (1) in which $R^2$ represents a pyridyl group, and $R^3$ represents a hydrogen atom;

a compound represented by Formula (1) in which $R^2$ represents pyrimidinyl group, and $R^3$ represents a hydrogen atom;

a compound represented by Formula (1) in which $R^2$ represents a thienyl group, and $R^3$ represents a hydrogen atom;

a compound represented by Formula (1) in which $R^2$ represents a phenoxy group, and $R^3$ represents a hydrogen atom;

a compound represented by Formula (1) in which $R^2$ represents a phenylthio group, and $R^3$ represents a hydrogen atom;

a compound represented by Formula (1) in which $R^2$ represents an amino group, and $R^3$ represents a hydrogen atom;

a compound represented by Formula (1) in which $R^2$ represents an acetyl group, and $R^3$ represents a hydrogen atom;

a compound represented by Formula (1) in which $R^2$ represents a trifluoroacetyl group, and $R^3$ represents a hydrogen atom;

a compound represented by Formula (1) in which $R^2$ represents a cyano group, and $R^3$ represents a hydrogen atom;

a compound represented by Formula (1) in which $R^2$ represents a nitro group, and $R^3$ represents a hydrogen atom;

a compound represented by Formula (1) in which $R^2$ represents a carboxy group, and $R^3$ represents a hydrogen atom;

a compound represented by Formula (1) in which $R^2$ represents —$SF_5$, and $R^3$ represents a hydrogen atom;

a compound represented by Formula (1) in which $R^2$ represents a benzoyl group, and $R^3$ represents a hydrogen atom;

a compound represented by Formula (1) in which $R^2$ represents a fluorine atom, and $R^3$ represents a cyano group;

a compound represented by Formula (1) in which $R^2$ represents a chlorine atom, and $R^3$ represents a cyano group;

a compound represented by Formula (1) in which $R^2$ represents a bromine atom, and $R^3$ represents a cyano group;

a compound represented by Formula (1) in which $R^2$ represents an iodine atom, and $R^3$ represents a cyano group;

a compound represented by Formula (1) in which $R^2$ represents a methyl group, and $R^3$ represents a cyano group;

a compound represented by Formula (1) in which $R^2$ represents an ethyl group, and $R^3$ represents a cyano group;

a compound represented by Formula (1) in which $R^2$ represents an isopropyl group, and $R^3$ represents a cyano group;

a compound represented by Formula (1) in which $R^2$ represents a tert-butyl group, and $R^3$ represents a cyano group;

a compound represented by Formula (1) in which $R^2$ represents a difluoromethyl group, and $R^3$ represents a cyano group;

a compound represented by Formula (1) in which $R^2$ represents a trifluoromethyl group, and $R^3$ represents a cyano group;

a compound represented by Formula (1) in which $R^2$ represents a pentafluoroethyl group, and $R^3$ represents a cyano group;

a compound represented by Formula (1) in which $R^2$ represents a heptafluoropropyl group, and $R^3$ represents a cyano group;

a compound represented by Formula (1) in which $R^2$ represents a heptafluoroisopropyl group, and $R^3$ represents a cyano group;

a compound represented by Formula (1) in which $R^2$ represents a methoxycarbonyl group, and $R^3$ represents a cyano group;

a compound represented by Formula (1) in which $R^2$ represents an ethoxycarbonyl group, and $R^3$ represents a cyano group;

a compound represented by Formula (1) in which $R^2$ represents an aminocabonyl group, and $R^3$ represents a cyano group;

a compound represented by Formula (1) in which $R^2$ represents a methoxy group, and $R^3$ represents a cyano group;

a compound represented by Formula (1) in which $R^2$ represents an ethoxy group, and $R^3$ represents a cyano group;

a compound represented by Formula (1) in which $R^2$ represents a difluoromethoxy group, and $R^3$ represents a cyano group;

a compound represented by Formula (1) in which $R^2$ represents a trifluoromethoxy group, and $R^3$ represents a cyano group;

a compound represented by Formula (1) in which $R^2$ represents a methylthio group, and $R^3$ represents a cyano group;

a compound represented by Formula (1) in which $R^2$ represents a methylsulfinyl group, and $R^3$ represents a cyano group;

a compound represented by Formula (1) in which $R^2$ represents a methylsulfonyl group, and $R^3$ represents a cyano group;

a compound represented by Formula (1) in which $R^2$ represents a trifluoromethylthio group, and $R^3$ represents a cyano group;

a compound represented by Formula (1) in which $R^2$ represents a trifluoromethylsulfinyl group, and $R^3$ represents a cyano group;

a compound represented by Formula (1) in which $R^2$ represents a trifluoromethylsulfonyl group, and $R^3$ represents a cyano group;

a compound represented by Formula (1) in which $R^2$ represents a phenyl group, and $R^3$ represents a cyano group;

a compound represented by Formula (1) in which $R^2$ represents a pyridyl group, and $R^3$ represents a cyano group;

a compound represented by Formula (1) in which $R^2$ represents a pyrimidinyl group, and $R^3$ represents a cyano group;

a compound represented by Formula (1) in which $R^2$ represents a thienyl group, and $R^3$ represents a cyano group;

a compound represented by Formula (1) in which $R^2$ represents a phenoxy group, and $R^3$ represents a cyano group;

a compound represented by Formula (1) in which $R^2$ represents a phenylthio group, and $R^3$ represents a cyano group;

a compound represented by Formula (1) in which $R^2$ represents an amino group, and $R^3$ represents a cyano group;

a compound represented by Formula (1) in which $R^2$ represents an acetyl group, and $R^3$ represents a cyano group;

a compound represented by Formula (1) in which $R^2$ represents a trifluoroacetyl group, and $R^3$ represents a cyano group;

a compound represented by Formula (1) in which $R^2$ represents a cyano group, and $R^3$ represents a cyano group;

a compound represented by Formula (1) in which $R^2$ represents a nitro group, and $R^3$ represents a cyano group;

a compound represented by Formula (1) in which $R^2$ represents a carboxy group, and $R^3$ represents a cyano group;

a compound represented by Formula (1) in which $R^2$ represents —$SF_5$, and $R^3$ represents a cyano group;

a compound represented by Formula (1) in which $R^2$ represents a benzoyl group, and $R^3$ represents a cyano group;

a compound represented by Formula (1) in which $R^2$ represents a fluorine atom, and $R^3$ represents a C1-C6 alkyl group optionally having one or more groups selected from the group X;

a compound represented by Formula (1) in which $R^2$ represents a chlorine atom, and $R^3$ represents a C1-C6 alkyl group optionally having one or more groups selected from the group X;

a compound represented by Formula (1) in which $R^2$ represents a bromine atom, and $R^3$ represents a C1-C6 alkyl group optionally having one or more groups selected from the group X;

a compound represented by Formula (1) in which $R^2$ represents an iodine atom, and $R^3$ represents a C1-C6 alkyl group optionally having one or more groups selected from the group X;

a compound represented by Formula (1) in which $R^2$ represents a methyl group, and $R^3$ represents a C1-C6 alkyl group optionally having one or more groups selected from the group X;

a compound represented by Formula (1) in which $R^2$ represents an ethyl group, and $R^3$ represents a C1-C6 alkyl group optionally having one or more groups selected from the group X;

a compound represented by Formula (1) in which $R^2$ represents an isopropyl group, and $R^3$ represents a C1-C6 alkyl group optionally having one or more groups selected from the group X;

a compound represented by Formula (1) in which $R^2$ represents a tert-butyl group, and $R^3$ represents a C1-C6 alkyl group optionally having one or more groups selected from the group X;

a compound represented by Formula (1) in which $R^2$ represents a difluoromethyl group, and $R^3$ represents a C1-C6 alkyl group optionally having one or more groups selected from the group X;

a compound represented by Formula (1) in which $R^2$ represents a trifluoromethyl group, and $R^3$ represents a C1-C6 alkyl group optionally having one or more groups selected from the group X;

a compound represented by Formula (1) in which $R^2$ represents a pentafluoroethyl group, and $R^3$ represents a C1-C6 alkyl group optionally having one or more groups selected from the group X;

a compound represented by Formula (1) in which $R^2$ represents a heptafluoropropyl group, and $R^3$ represents a C1-C6 alkyl group optionally having one or more groups selected from the group X;

a compound represented by Formula (1) in which $R^2$ represents a heptafluoroisopropyl group, and $R^3$ represents a C1-C6 alkyl group optionally having one or more groups selected from the group X;

a compound represented by Formula (1) in which $R^2$ represents a methoxycarbonyl group, and $R^3$ represents a C1-C6 alkyl group optionally having one or more groups selected from the group X;

a compound represented by Formula (1) in which $R^2$ represents an ethoxycarbonyl group, and $R^3$ represents a C1-C6 alkyl group optionally having one or more groups selected from the group X;

a compound represented by Formula (1) in which $R^2$ represents an aminocarbonyl group, and $R^3$ represents a C1-C6 alkyl group optionally having one or more groups selected from the group X;

a compound represented by Formula (1) in which $R^2$ represents a methoxy group, and $R^3$ represents a C1-C6 alkyl group optionally having one or more groups selected from the group X;

a compound represented by Formula (1) in which $R^2$ represents an ethoxy group, and $R^3$ represents a C1-C6 alkyl group optionally having one or more groups selected from the group X;

a compound represented by Formula (1) in which $R^2$ represents a difluoromethoxy group, and $R^3$ represents a C1-C6 alkyl group optionally having one or more groups selected from the group X;

a compound represented by Formula (1) in which $R^2$ represents a trifluoromethoxy group, and $R^3$ represents a C1-C6 alkyl group optionally having one or more groups selected from the group X;

a compound represented by Formula (1) in which $R^2$ represents a methylthio group, and $R^3$ represents a C1-C6 alkyl group optionally having one or more groups selected from the group X;

a compound represented by Formula (1) in which $R^2$ represents a methylsulfinyl group, and $R^3$ represents a C1-C6 alkyl group optionally having one or more groups selected from the group X;

a compound represented by Formula (1) in which $R^2$ represents a methylsulfonyl group, and $R^3$ represents a C1-C6 alkyl group optionally having one or more groups selected from the group X;

a compound represented by Formula (1) in which $R^2$ represents a trifluoromethylthio group, and $R^3$ represents a C1-C6 alkyl group optionally having one or more groups selected from the group X;

a compound represented by Formula (1) in which $R^2$ represents a trifluoromethylsulfinyl group, and $R^3$ represents a C1-C6 alkyl group optionally having one or more groups selected from the group X;

a compound represented by Formula (1) in which $R^2$ represents a trifluoromethylsulfonyl group, and $R^3$ represents a C1-C6 alkyl group optionally having one or more groups selected from the group X;

a compound represented by Formula (1) in which $R^2$ represents a fluorine atom, and $R^3$ represents a methyl group;

a compound represented by Formula (1) in which $R^2$ represents a chlorine atom, and $R^3$ represents a methyl group;

a compound represented by Formula (1) in which $R^2$ represents a bromine atom, and $R^3$ represents a methyl group;

a compound represented by Formula (1) in which $R^2$ represents an iodine atom, and $R^3$ represents a methyl group;

a compound represented by Formula (1) in which $R^2$ represents a methyl group, and $R^3$ represents a methyl group;

a compound represented by Formula (1) in which $R^2$ represents an ethyl group, and $R^3$ represents a methyl group;

a compound represented by Formula (1) in which $R^2$ represents an isopropyl group, and $R^3$ represents a methyl group;

a compound represented by Formula (1) in which $R^2$ represents a tert-butyl group, and $R^3$ represents a methyl group;

a compound represented by Formula (1) in which $R^2$ represents a difluoromethyl group, and $R^3$ represents a methyl group;

a compound represented by Formula (1) in which $R^2$ represents a trifluoromethyl group, and $R^3$ represents a methyl group;

a compound represented by Formula (1) in which $R^2$ represents a pentafluoroethyl group, and $R^3$ represents a methyl group;

a compound represented by Formula (1) in which $R^2$ represents a heptafluoropropyl group, and $R^3$ represents a methyl group;

a compound represented by Formula (1) in which $R^2$ represents a heptafluoroisopropyl group, and $R^3$ represents a methyl group;

a compound represented by Formula (1) in which $R^2$ represents a methoxycarbonyl group, and $R^3$ represents a methyl group;

a compound represented by Formula (1) in which $R^2$ represents an ethoxycarbonyl group, and $R^3$ represents a methyl group;

a compound represented by Formula (1) in which $R^2$ represents an aminocarbonyl group, and $R^3$ represents a methyl group;

a compound represented by Formula (1) in which $R^2$ represents a methoxy group, and $R^3$ represents a methyl group;

a compound represented by Formula (1) in which $R^2$ represents an ethoxy group, and $R^3$ represents a methyl group;

a compound represented by Formula (1) in which $R^2$ represents a difluoromethoxy group, and $R^3$ represents a methyl group;

a compound represented by Formula (1) in which $R^2$ represents a trifluoromethoxy group, and $R^3$ represents a methyl group;

a compound represented by Formula (1) in which $R^2$ represents a methylthio group, and $R^3$ represents a methyl group;

a compound represented by Formula (1) in which $R^2$ represents a methylsulfinyl group, and $R^3$ represents a methyl group;

a compound represented by Formula (1) in which $R^2$ represents a methylsulfonyl group, and $R^3$ represents a methyl group;

a compound represented by Formula (1) in which $R^2$ represents a trifluoromethylthio group, and $R^3$ represents a methyl group;

a compound represented by Formula (1) in which $R^2$ represents a trifluoromethylsulfinyl group, and $R^3$ represents a methyl group;

a compound represented by Formula (1) in which $R^2$ represents a trifluoromethylsulfonyl group, and $R^3$ represents a methyl group;

a compound represented by Formula (1) in which $R^2$ represents a phenyl group, and $R^3$ represents a methyl group;

a compound represented by Formula (1) in which $R^2$ represents a pyridyl group, and $R^3$ represents a methyl group;

a compound represented by Formula (1) in which $R^2$ represents a pyrimidinyl group, and $R^3$ represents a methyl group;

a compound represented by Formula (1) in which $R^2$ represents a thienyl group, and $R^3$ represents a methyl group;

a compound represented by Formula (1) in which $R^2$ represents a phenoxy group, and $R^3$ represents a methyl group;

a compound represented by Formula (1) in which $R^2$ represents a phenylthio group, and $R^3$ represents a methyl group;

a compound represented by Formula (1) in which $R^2$ represents an amino group, and $R^3$ represents a methyl group;

a compound represented by Formula (1) in which $R^2$ represents an acetyl group, and $R^3$ represents a methyl group;

a compound represented by Formula (1) in which $R^2$ represents a trifluoroacetyl group, and $R^3$ represents a methyl group;

a compound represented by Formula (1) in which $R^2$ represents a cyano group, and $R^3$ represents a methyl group;

a compound represented by Formula (1) in which $R^2$ represents a nitro group, and $R^3$ represents a methyl group;

a compound represented by Formula (1) in which $R^2$ represents a carboxy group, and $R^3$ represents a methyl group;

a compound represented by Formula (1) in which $R^2$ represents —$SF_5$, and $R^3$ represents a methyl group;

a compound represented by Formula (1) in which $R^2$ represents a benzoyl group, and $R^3$ represents a methyl group;

a compound represented by Formula (1) in which $R^2$ represents a fluorine atom, and $R^3$ represents a trifluoromethyl group;

a compound represented by Formula (1) in which $R^2$ represents a chlorine atom, and $R^3$ represents a trifluoromethyl group;

a compound represented by Formula (1) in which $R^2$ represents bromine atom, and $R^3$ represents a trifluoromethyl group;

a compound represented by Formula (1) in which $R^2$ represents an iodine atom, and $R^3$ represents a trifluoromethyl group;

a compound represented by Formula (1) in which $R^2$ represents a trifluoromethyl group, and $R^3$ represents a trifluoromethyl group;

a compound represented by Formula (1) in which $R^2$ represents an ethyl group, and $R^3$ represents a trifluoromethyl group;

a compound represented by Formula (1) in which $R^2$ represents an isopropyl, and $R^3$ represents a trifluoromethyl group;

a compound represented by Formula (1) in which $R^2$ represents a tert-butyl group, and $R^3$ represents a trifluoromethyl group;

a compound represented by Formula (1) in which $R^2$ represents a difluoromethyl group, and $R^3$ represents trifluoromethyl group;

a compound represented by Formula (1) in which $R^2$ represents a trifluoromethyl group, and $R^3$ represents a trifluoromethyl group;

a compound represented by Formula (1) in which $R^2$ represents a pentafluoroethyl group, and $R^3$ represents a trifluoromethyl group;

a compound represented by Formula (1) in which $R^2$ represents a heptafluoropropyl group, and $R^3$ represents a trifluoromethyl group;

a compound represented by Formula (1) in which $R^2$ represents a heptafluoroisopropyl group, and $R^3$ represents a trifluoromethyl group;

a compound represented by Formula (1) in which $R^2$ represents a methoxycarbonyl group, and $R^3$ represents a trifluoromethyl group;

a compound represented by Formula (1) in which $R^2$ represents an ethoxycarbonyl group, and $R^3$ represents a trifluoromethyl group;

a compound represented by Formula (1) in which $R^2$ represents an aminocabonyl group, and $R^3$ represents a trifluoromethyl group;

a compound represented by Formula (1) in which $R^2$ represents a methoxy group, and $R^3$ represents a trifluoromethyl group;

a compound represented by Formula (1) in which $R^2$ represents an ethoxy group, and $R^3$ represents a trifluoromethyl group;

a compound represented by Formula (1) in which $R^2$ represents a difluoromethoxy group, and $R^3$ represents a trifluoromethyl group;

a compound represented by Formula (1) in which $R^2$ represents a trifluoromethoxy group, and $R^3$ represents a trifluoromethyl group;

a compound represented by Formula (1) in which $R^2$ represents a methylthio group, and $R^3$ represents a trifluoromethyl group;

a compound represented by Formula (1) in which $R^2$ represents a methylsulfinyl group, and $R^3$ represents a trifluoromethyl group;

a compound represented by Formula (1) in which $R^2$ represents a methylsulfonyl group, and $R^3$ represents a trifluoromethyl group;

a compound represented by Formula (1) in which $R^2$ represents a trifluoromethylthio group, and $R^3$ represents a trifluoromethyl group;

a compound represented by Formula (1) in which $R^2$ represents trifluoromethylsulfinyl group, and $R^3$ represents a trifluoromethyl group;

a compound represented by Formula (1) in which $R^2$ represents a trifluoromethylsulfonyl group, and represents a trifluoromethyl group;

a compound represented by Formula (1) in which $R^2$ represents a phenyl group, and $R^3$ represents a trifluoromethyl group;

a compound represented by Formula (1) in which $R^2$ represents a pyridyl group, and $R^3$ represents a trifluoromethyl group;

a compound represented by Formula (1) in which $R^2$ represents a pyrimidinyl group, and $R^3$ represents a trifluoromethyl group;

a compound represented by Formula (1) in which $R^2$ represents a thienyl group, and $R^3$ represents a trifluoromethyl group;

a compound represented by Formula (1) in which $R^2$ represents a phenoxy group, and $R^3$ represents a trifluoromethyl group;

a compound represented by Formula (1) in which $R^2$ represents a phenylthio group, and $R^3$ represents a trifluoromethyl group;

a compound represented by Formula (1) in which $R^2$ represents an amino group, and $R^3$ represents a trifluoromethyl group;

a compound represented by Formula (1) in which $R^2$ represents an acetyl group, and $R^3$ represents a trifluoromethyl group;

a compound represented by Formula (1) in which $R^2$ represents a trifluoroacetyl group, and $R^3$ represents a trifluoromethyl group;

a compound represented by Formula (1) in which $R^2$ represents a cyano group, and $R^3$ represents a trifluoromethyl group;

a compound represented by Formula (1) in which $R^2$ represents a nitro group, and $R^3$ represents a trifluoromethyl group;

a compound represented by Formula (1) in which $R^2$ represents a carboxy group, and $R^3$ represents a trifluoromethyl group;

a compound represented by Formula (1) in which $R^2$ represents —$SF_5$, and $R^3$ represents a trifluoromethyl group;

a compound represented by Formula (1) in which $R^2$ represents benzoyl group, and $R^3$ represents a trifluoromethyl group;

a compound represented by Formula (1) in which $R^2$ represents a fluorine atom, and $R^3$ represents a pentafluoroethyl group;

a compound represented by Formula (1) in which $R^2$ represents a chlorine atom, and $R^3$ represents a pentafluoroethyl group;

a compound represented by Formula (1) in which $R^2$ represents a bromine atom, and $R^3$ represents a pentafluoroethyl group;

a compound represented by Formula (1) in which $R^2$ represents an iodine atom, and $R^3$ represents a pentafluoroethyl group;

a compound represented by Formula (1) in which $R^2$ represents a methyl group, and $R^3$ represents a pentafluoroethyl group;

a compound represented by Formula (1) in which $R^2$ represents an ethyl group, and $R^3$ represents a pentafluoroethyl group;

a compound represented by Formula (1) in which $R^2$ represents an isopropyl group, and $R^3$ represents a pentafluoroethyl group;

a compound represented by Formula (1) in which $R^2$ represents a tert-butyl group, and $R^3$ represents a pentafluoroethyl group;

a compound represented by Formula (1) in which $R^2$ represents a difluoromethyl group, and $R^3$ represents a pentafluoroethyl group;

a compound represented by Formula (1) in which $R^2$ represents a trifluoromethyl group, and $R^3$ represents a pentafluoroethyl group;

a compound represented by Formula (1) in which $R^2$ represents a pentafluoroethyl group, and $R^3$ represents a pentafluoroethyl group;

a compound represented by Formula (1) in which $R^2$ represents a heptafluoropropyl group, and $R^3$ represents a pentafluoroethyl group;

a compound represented by Formula (1) in which $R^2$ represents a heptafluoroisopropyl group, and $R^3$ represents a pentafluoroethyl group;

a compound represented by Formula (1) in which $R^2$ represents a methoxycarbonyl group, and $R^3$ represents a pentafluoroethyl group;

a compound represented by Formula (1) in which $R^2$ represents an ethoxycarbonyl group, and $R^3$ represents a pentafluoroethyl group;

a compound represented by Formula (1) in which $R^2$ represents an aminocarbonyl group, and $R^3$ represents a pentafluoroethyl group;

a compound represented by Formula (1) in which $R^2$ represents a methoxy group, and $R^3$ represents a pentafluoroethyl group;

a compound represented by Formula (1) in which $R^2$ represents an ethoxy group, and $R^3$ represents a pentafluoroethyl group;

a compound represented by Formula (1) in which $R^2$ represents a difluoromethoxy group, and $R^3$ represents a pentafluoroethyl group;

a compound represented by Formula (1) in which $R^2$ represents a trifluoromethoxy group, and $R^3$ represents a pentafluoroethyl group;

a compound represented by Formula (1) in which $R^2$ represents a methylthio group, and $R^3$ represents a pentafluoroethyl group;

a compound represented by Formula (1) in which $R^2$ represents a methylsulfinyl group, and $R^3$ represents a pentafluoroethyl group;

a compound represented by Formula (1) in which $R^2$ represents a methylsulfonyl group, and $R^3$ represents a pentafluoroethyl group;

a compound represented by Formula (1) in which $R^2$ represents a trifluoromethylthio group, and $R^3$ represents a pentafluoroethyl group;

a compound represented by Formula (1) in which $R^2$ represents a trifluoromethylsulfinyl group, and $R^3$ represents a pentafluoroethyl group;

a compound represented by Formula (1) in which $R^2$ represents trifluoromethylsulfonyl group, and $R^3$ represents a pentafluoroethyl group;

a compound represented by Formula (1) in which $R^2$ represents a phenyl group, and $R^3$ represents a pentafluoroethyl group;

a compound represented by Formula (1) in which $R^2$ represents a pyridyl group, and $R^3$ represents a pentafluoroethyl group;

a compound represented by Formula (1) in which $R^2$ represents a pyrimidinyl group, and $R^3$ represents a pentafluoroethyl group;

a compound represented by Formula (1) in which $R^2$ represents a thienyl group, and $R^3$ represents a pentafluoroethyl group;

a compound represented by Formula (1) in which $R^2$ represents a phenoxy group, and $R^3$ represents a pentafluoroethyl group;

a compound represented by Formula (1) in which $R^2$ represents a phenylthio group, and $R^3$ represents a pentafluoroethyl group;

a compound represented by Formula (1) in which $R^2$ represents an amino group, and $R^3$ represents a pentafluoroethyl group;

a compound represented by Formula (1) in which $R^2$ represents an acetyl group, and $R^3$ represents a pentafluoroethyl group;

a compound represented by Formula (1) in which $R^2$ represents a trifluoroacetyl group, and $R^3$ represents a pentafluoroethyl group;

a compound represented by Formula (1) in which $R^2$ represents a cyano group, and $R^3$ represents a pentafluoroethyl group;

a compound represented by Formula (1) in which $R^2$ represents a nitro group, and $R^3$ represents a pentafluoroethyl group;

a compound represented by Formula (1) in which $R^2$ represents a carboxy group, and $R^3$ represents a pentafluoroethyl group;

a compound represented by Formula (1) in which $R^2$ represents —$SF_5$, and $R^3$ represents a pentafluoroethyl group;

a compound represented by Formula (1) in which $R^2$ represents a benzoyl group, and $R^3$ represents pentafluoroethyl group;

a compound represented by Formula (1) in which $R^2$ represents a C1-C6 alkyl group optionally having one or more groups selected from the group X, and $R^3$ represents a hydrogen atom;

a compound represented by Formula (1) in which $R^2$ represents a trifluoromethyl group, and $R^3$ represents a hydrogen atom;

a compound represented by Formula (1) in which $R^2$ represents a C2-C6 alkoxycarbonyl group, and $R^3$ represents a C1-C6 alkyl group optionally having one or more groups selected from the group X;

a compound represented by Formula (1) in which $R^2$ represents a methoxycarbonyl group, and $R^3$ represents a C1-C6 alkyl group optionally having one or more groups selected from the group X;

a compound represented by Formula (1) in which $R^2$ represents a C2-C6 alkoxycarbonyl group, and $R^3$ represents a trifluoromethyl group;

a compound represented by Formula (1) in which $R^2$ represents a cyano group, a halogen atom, a nitro group, a C1-C6 alkyl group optionally having one or more groups selected from the group X, a phenyl group optionally having one or more groups selected from the group Y, —$NR^9R^{10}$, —$OR^9$, —$S(O)_mR^9$, or —$SF_5$;

a compound represented by Formula (1) in which $R^2$ represents a cyano group, a halogen atom, a nitro group, a C1-C6 alkyl group optionally having one or more groups selected from the group X, a phenyl group optionally having one or more groups selected from the group Y, —$OR^9$, or —$S(O)_mR^9$;

a compound represented by Formula (1) in which $R^2$ represents a cyano group, a halogen atom, a nitro group, a C1-C6 alkyl group optionally having one or more groups selected from the group X, a phenyl group optionally having one or more groups selected from the group Y, or —$OR^9$;

a compound represented by Formula (1) in which $R^2$ represents a cyano group, a halogen atom, a nitro group, a C1-C6 alkyl group optionally having one or more halogen atoms, a phenyl group optionally having one or more groups selected from the group Y, or —$OR^9$;

a compound represented by Formula (1) in which R² represents a cyano group, a halogen atom, a nitro group, a methyl group, a difluoromethyl group, a trifluoromethyl group, a pentafluoroethyl group, a phenyl group optionally having one or more groups selected from the group Y, a methoxy group, a difluoromethoxy group, a trifluoromethoxy group, a methylthio group, a methylsulfinyl group, a methylsulfonyl group, a trifluoromethylthio group, a trifluoromethylsulfinyl group, or a trifluoromethylsulfonyl group;

a compound represented by Formula (1) in which R² represents a cyano group, a halogen atom, a nitro group, a methyl group, a difluoromethyl group, a trifluoromethyl group, a pentafluoroethyl group, a phenyl group optionally having one or more groups selected from the group Y, a methoxy group, a difluoromethoxy group, or a trifluoromethoxy group;

a compound represented by Formula (1) in which R³ represents a hydrogen atom, a cyano group, a C1-C6 alkyl group optionally having one or more groups selected from the group X, a C2-C6 alkylcarbonyl group optionally having one or more halogen atoms, or a benzoyl group optionally having one or more groups selected from the group Y;

a compound represented by Formula (1) in which R³ represents a hydrogen atom or a C1-C6 alkyl group optionally having one or more groups selected from the group X;

a compound represented by Formula (1) in which R³ represents a hydrogen atom, a methyl group; an ethyl group, a propyl group, an isopropyl group, a trifluoromethyl group, a pentafluoroethyl group, a heptafluoropropyl group, or a heptafluoroisopropyl group;

a compound represented by Formula (1) in which R³ represents a hydrogen atom, a methyl group, a trifluoromethyl group, or a pentafluoroethyl group;

a compound represented by Formula (1) in which R³ represents a hydrogen atom, a methyl group, or a trifluoromethyl group;

a compound represented by Formula (1) in which R³ represents a hydrogen atom or a trifluoromethyl group;

a compound represented by Formula (1) in which R² represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —NR⁹R¹⁰, —OR⁹, —S(O)$_m$R⁹, or —SF₅, and R³ represents a hydrogen atom, a cyano group, a C1-C6 alkyl group optionally having one or more groups selected from the group X, a C2-C6 alkylcarbonyl group optionally having one or more halogen atoms, or a benzoyl group optionally having one or more groups selected from the group Y;

a compound represented by Formula (1) in which R² represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —NR⁹R¹⁰, —OR⁹, —S(O)$_m$R⁹, or —SF₅, and R³ represents a hydrogen atom or a C1-C6 alkyl group optionally having one or more groups selected from the group X;

a compound represented by Formula (1) in which R² represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —NR⁹R¹⁰, —OR⁹, —S(O)$_m$R⁹, or —SF₅, and R³ represents a hydrogen atom, a methyl group, an ethyl group, a propyl group, an isopropyl group, a trifluoromethyl group, a pentafluoroethyl group, a heptafluoropropyl group, or a heptafluoroisopropyl group;

a compound represented by Formula (1) in which R² represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —NR⁹R¹⁰, —OR⁹, —S(O)$_m$R⁹, or —SF₅, and R³ represents a hydrogen atom, or a C1-C6 alkyl group optionally having one or more groups selected from the group X;

a compound represented by Formula (1) in which R² represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —NR⁹R¹⁰, —OR⁹, —S(O)$_m$R⁹, or —SF₅, and R³ represents a hydrogen atom, a methyl group, a trifluoromethyl group, or a pentafluoroethyl group; a compound represented by Formula (1) in which R² represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —NR⁹R¹⁰, —OR⁹, —S(O)$_m$R⁹, or —SF₅, and R³ represents a hydrogen atom, a methyl group, or a trifluoromethyl group;

a compound represented by Formula (1) in which R² represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —NR⁹R¹⁰, —OR⁹, —S(O)$_m$R⁹, or —SF₅, and R³ represents a hydrogen atom or a trifluoromethyl group;

a compound represented by Formula (1) in which R² represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —OR⁹, or —S(O)$_m$R⁹, and R³ represents a hydrogen atom, a cyano group, a C1-C6 alkyl group optionally having one or more groups selected from the group X, a C2-C6 alkylcarbonyl group optionally having one or more halogen atoms, or a benzoyl group optionally having one or more groups selected from the group Y;

a compound represented by Formula (1) in which R² represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —OR⁹, or —S(O)$_m$R⁹, and R³ represents a hydrogen atom, or a C1-C6 alkyl group optionally having one or more groups selected from the group X;

a compound represented by Formula (1) in which R² represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —OR$^9$, or —S(O)$_m$R$^9$, and R$^3$ represents a hydrogen atom, a methyl group, an ethyl group, a propyl group, an isopropyl group trifluoromethyl group, a pentafluoroethyl group, a heptafluoropropyl group, or a heptafluoroisopropyl group;

a compound represented by Formula (1) in which R$^2$ represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —OR$^9$, or —S(O)$_m$R$^9$, and R$^3$ represents a hydrogen atom, a methyl group, a trifluoromethyl group, or a pentafluoroethyl group;

a compound represented by Formula (1) in which R$^2$ represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —OR$^9$, or —S(O)$_m$R$^9$, and R$^3$ represents a hydrogen atom, a methyl group or a trifluoromethyl group;

a compound represented by Formula (1) in which R$^2$ represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —OR$^9$, or —S(O)$_m$R$^9$, and R$^3$ represents a hydrogen atom or a trifluoromethyl group;

a compound represented by Formula (1) in which R$^2$ represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, or —OR$^9$, and R$^3$ represents a hydrogen atom, a cyano group, a C1-C6 alkyl group optionally having one or more groups selected from the group X, a C2-C6 alkylcarbonyl group optionally having one or more halogen atoms, or a benzoyl group optionally having one or more groups selected from the group Y;

a compound represented by Formula (1) in which R$^2$ represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, or —OR$^9$, and R$^3$ represents a hydrogen atom or a C1-C6 alkyl group optionally having one or more groups selected from the group X;

a compound represented by Formula (1) in which R$^2$ represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, or —OR$^9$, and R$^3$ represents a hydrogen atom, a methyl group, an ethyl group, a propyl group, an isopropyl group, a trifluoromethyl group, a pentafluoroethyl group, a heptafluoropropyl group, or a heptafluoroisopropyl group;

a compound represented by Formula (1) in which R$^2$ represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, or —OR$^9$, and R$^3$ represents a hydrogen atom, a methyl group, a trifluoromethyl group, or a pentafluoroethyl group;

a compound represented by Formula (1) in which R$^2$ represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, or —OR$^9$, and R$^3$ represents a hydrogen atom, a methyl group, or a trifluoromethyl group;

a compound represented by Formula (1) in which R$^2$ represents a cyano group, a halogen atom, a nitro group, a C1-C6 alkyl group optionally having one or more halogen atoms, a phenyl group optionally having one or more groups selected from the group Y, a C2-C6 alkoxycarbonyl group, or —OR$^9$; and R$^3$ represents a hydrogen atom, a cyano group, a C1-C6 alkyl group optionally having one or more groups selected from the group X, a C2-C6 alkylcarbonyl group optionally having one or more halogen atoms, or a benzoyl group optionally having one or more groups selected from the group Y;

a compound represented by Formula (1) in which R$^2$ represents a cyano group, a halogen atom, a nitro group, a C1-C6 alkyl group optionally having one or more halogen atoms, a phenyl group optionally having one or more groups selected from the group Y, a C2-C6 alkoxycarbonyl group, or —OR$^9$; and R$^3$ represents a hydrogen atom, or a C1-C6 alkyl group optionally having one or more groups selected from the group X;

a compound represented by Formula (1) in which R$^2$ represents a cyano group, a halogen atom, a nitro group, a C1-C6 alkyl group optionally having one or more halogen atoms, a phenyl group optionally having one or more groups selected from the group Y, a C2-C6 alkoxycarbonyl group, or —OR$^9$; and R$^3$ represents a hydrogen atom, a methyl group, an ethyl group, a propyl group, an isopropyl group, a trifluoromethyl group, pentafluoroethyl group, a heptafluoropropyl group, or a heptafluoroisopropyl group;

a compound represented by Formula (1) in which R$^2$ represents a cyano group, a halogen atom, a nitro group, a C1-C6 alkyl group optionally having one or more halogen atoms, a phenyl group optionally having one or more groups selected from the group Y, a C2-C6 alkoxycarbonyl group, or —OR$^9$; and R$^3$ represents a hydrogen atom, a methyl group, a trifluoromethyl group, or a pentafluoroethyl group;

a compound represented by Formula (1) in which R$^2$ represents a cyano group, a halogen atom, a nitro group, a C1-C6 alkyl group optionally having one or more halogen atoms, a phenyl group optionally having one or more groups selected from the group Y, a C2-C6 alkoxycarbonyl group, or —OR$^9$; and R$^3$ represents a hydrogen atom, a methyl group, or a trifluoromethyl group;

a compound represented by Formula (1) in which R$^2$ represents a cyano group, a halogen atom, a nitro group, a C1-C6 alkyl group optionally having one or more halogen atoms, a phenyl group optionally having one or more groups selected from the group Y, a C2-C6 alkoxycarbonyl group, or —OR$^9$; and $R^3$ represents a hydrogen atom or a trifluoromethyl group;

a compound represented by Formula (1) in which $R^2$ represents a cyano group, a halogen atom, a nitro group, a methyl group, a difluoromethyl group, a trifluoromethyl group, a pentafluoroethyl group, a phenyl group optionally having one or more groups selected from the group Y, a methoxycarbonyl group, a methoxy group, a difluoromethoxy group, a trifluoromethoxy group, a methylthio group, a methylsulfinyl group, methylsulfonyl group, a trifluoromethylthio group, a trifluoromethylsulfinyl group, or a trifluoromethylsulfonyl group; and $R^3$ represents a hydrogen atom, a cyano group, a C1-C6 alkyl group optionally having one or more groups selected from the group X, a C2-C6 alkylcarbonyl group optionally having one or more halogen atoms, or a benzoyl group optionally having one or more groups selected from the group Y;

a compound represented by Formula (1) in which $R^2$ represents a cyano group, a halogen atom, a nitro group, a methyl group, a difluoromethyl group, a trifluoromethyl group, a pentafluoroethyl group, a phenyl group optionally having one or more groups selected from the group Y, a methoxycarbonyl group, a methoxy group, a difluoromethoxy group, a trifluoromethoxy group, a methylthio group, a methylsulfinyl group, a methylsulfonyl, group, trifluoromethylthio group, a trifluoromethylsulfinyl group, or a trifluoromethylsulfonyl group; and $R^3$ represents a hydrogen atom or a C1-C6 alkyl group optionally having one or more groups selected from the group X;

a compound represented by Formula (1) in which $R^2$ represents a cyano group, a halogen atom, a nitro group, a methyl group, a difluoromethyl group, a trifluoromethyl group, a pentafluoroethyl group, a phenyl group optionally having one or more groups selected from the group Y, a methoxycarbonyl group, a methoxy group, a difluoromethoxy group, a trifluoromethoxy group, a methylthio group, a methylsulfinyl group, a methylsulfonyl group, a trifluoromethylthio group, a trifluoromethylsulfinyl group, or a trifluoromethylsulfonyl group; and $R^3$ represents a hydrogen atom, a methyl group, an ethyl group, a propyl group, an isopropyl group, a trifluoromethyl group, a pentafluoroethyl group, a heptafluoropropyl group, a heptafluoroisopropyl group;

a compound represented by Formula (1) in which $R^2$ represents a cyano group, a halogen atom, a nitro group, a methyl group, a difluoromethyl group, a trifluoromethyl group, a pentafluoroethyl group, a phenyl group optionally having one or more groups selected from the group Y, a methoxycarbonyl group, a methoxy group, a difluoromethoxy group, a trifluoromethoxy group, a methylthio group, a methylsulfinyl group, a methylsulfonyl group, a trifluoromethylthio group, a trifluoromethylsulfinyl group, or a trifluoromethylsulfonyl group; and $R^3$ represents a hydrogen atom, a methyl group, a trifluoromethyl group, or a pentafluoroethyl group;

a compound represented by Formula (1) in which $R^2$ represents a cyano group, a halogen atom, a nitro group, a methyl group, a difluoromethyl group, a trifluoromethyl group, a pentafluoroethyl group, a phenyl group optionally having one or more groups selected from the group Y, a methoxycarbonyl group, a methoxy group, a difluoromethoxy group, a trifluoromethoxy group, a methylthio group, a methylsulfinyl group, a methylsulfonyl group, a trifluoromethylthio group, a trifluoromethylsulfinyl group, or a trifluoromethylsulfonyl group; and $R^3$ represents a hydrogen atom, a methyl group, or a trifluoromethyl group;

a compound represented by Formula (1) in which $R^2$ represents a cyano group, a halogen atom, a nitro group, a methyl group, a difluoromethyl group, a trifluoromethyl group, a pentafluoroethyl group, a phenyl group optionally having one or more groups selected from the group Y, a methoxycarbonyl group, a methoxy group, a difluoromethoxy group, or a trifluoromethoxy group; and $R^3$ represents a hydrogen atom, a cyano group, a C1-C6 alkyl group optionally having one or more groups selected from the group X, a C2-C6 alkylcarbonyl group optionally having one or more halogen atoms, or a benzoyl group optionally having one or more groups selected from the group Y;

a compound represented by Formula (1) in which $R^2$ represents a cyano group, a halogen atom, a nitro group, a methyl group, a difluoromethyl group, a trifluoromethyl group, a pentafluoroethyl group, a phenyl group optionally having one or more groups selected from the group Y, a methoxycarbonyl group, a methoxy group, a difluoromethoxy group, or a trifluoromethoxy group; and $R^3$ represents a hydrogen atom or a C1-C6 alkyl group optionally having one or more groups selected from the group X;

a compound represented by Formula (1) in which $R^2$ represents a cyano group, a halogen atom, a nitro group, a methyl group, a difluoromethyl group, a trifluoromethyl group, a pentafluoroethyl group, a phenyl group optionally having one or more groups selected from the group Y, a methoxycarbonyl group, a methoxy group, a difluoromethoxy group, or a trifluoromethoxy group; and $R^3$ represents a hydrogen atom, a methyl group, an ethyl group, a propyl group, an isopropyl group, a trifluoromethyl group, a pentafluoroethyl group, a heptafluoropropyl group, or a heptafluoroisopropyl group;

a compound represented by Formula (1) in which $R^2$ represents a cyano group, a halogen atom, a nitro group, a methyl group, a difluoromethyl group, a trifluoromethyl group, a pentafluoroethyl group, a phenyl group optionally having one or more groups selected from the group Y, a methoxycarbonyl group, a methoxy group, a difluoromethoxy group, or a trifluoromethoxy group; and $R^3$ represents a hydrogen atom, a methyl group, trifluoromethyl group, or a pentafluoroethyl group;

a compound represented by Formula (1) in which $R^2$ represents a cyano group, a halogen atom, a nitro group, a methyl group, a difluoromethyl group, a trifluoromethyl group, a pentafluoroethyl group, a phenyl group optionally having one or more groups selected from the group Y, a methoxycarbonyl group, a methoxy group, a difluoromethoxy group, or a trifluoromethoxy group; and $R^3$ represents a hydrogen atom, a methyl group, or a trifluoromethyl group;

a compound represented by Formula (1) in which $R^2$ represents a cyano group, a halogen atom, a nitro group, a methyl group, a difluoromethyl group, a trifluoromethyl group, a pentafluoroethyl group, a phenyl group optionally having one or more groups selected from the group Y, a methoxycarbonyl group, a methoxy group, a difluoromethoxy group, or a trifluoromethoxy group; and $R^3$ represents a hydrogen atom or a trifluoromethyl group;

a compound represented by Formula (1) in which $R^1$ represents —C(O)W substituted at position 3, and W represents —ON=CR$^4$R$^5$ or —OR$^6$;

a compound represented by Formula (1) in which $R^1$ represents —C(O)W substituted at position 3, and W represents —OR$^6$ or —NR$^4$R$^8$;

a compound represented by Formula (1) in which $R^1$ represents —C(O)W substituted at position 3, W represents —ON=CR$^4$R$^5$ or —OR$^6$, and $R^2$ represents a cyano group, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocabonyl group, —NR$^9$R$^{10}$, —S(O)$_2$NR$^4$R$^9$, —OR$^9$, —S(O)$_m$R$^9$, or —SF$_5$;

a compound represented by Formula (1) in which $R^1$ represents —C(O)W substituted at position 3, W represents —OR$^6$ or —NR$^4$R$^8$, and $R^2$ represents a cyano group, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocabonyl group, —NR$^9$R$^{10}$, —S(O)$_2$NR$^4$R$^9$, —OR$^9$, —S(O)$_m$R$^9$, or —SF$_5$;

a compound represented by Formula (1) in which $R^1$ represents —C(O)W substituted at position 3, W represents —ON=CR$^4$R$^5$ or —OR$^6$, $R^2$ represents a cyano group, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocabonyl group, —NR$^9$R$^{10}$, —S(O)$_2$NR$^4$R$^9$, —OR$^9$, —S(O)$_m$R$^9$, or —SF$_5$, and $R^6$ represents a hydrogen atom, a C1-C6 alkyl group optionally having one or more groups selected from the group Z, a C3-C6 alkenyl group optionally having one or more groups selected from the group X, a C3-C6 alkynyl group optionally having one or more groups selected from the group X, or a phenyl group optionally having one or more groups selected from the group Y;

a compound represented by Formula (1) in which $R^1$ represents —C(O)W substituted at position 3, W represents —OR$^6$ or —NR$^4$R$^8$, $R^2$ represents a cyano group, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocabonyl group, —NR$^9$R$^{10}$, —S(O)$_2$NR$^4$R$^9$, —OR$^9$, —S(O)$_m$R$^9$, or —SF$_5$, and $R^6$ represents a hydrogen atom, a C1-C6 alkyl group optionally having one or more groups selected from the group Z, a C3-C6 alkenyl group optionally having one or more groups selected from the group X, a C3-C6 alkynyl group optionally having one or more groups selected from the group X, or a phenyl group optionally having one or more groups selected from the group Y;

a compound represented by Formula (1) in which $R^1$ represents —C(O)W substituted at position 3, W represents —ON=CR$^4$R$^5$ or —OR$^6$, $R^2$ represents a cyano group, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocabonyl group, —NR$^9$R$^{10}$, —S(O)$_2$NR$^4$R$^9$, —OR$^9$, —S(O)$_m$R$^9$, or —SF$_5$, and R6 represents a hydrogen atom, a C1-C6 alkyl group optionally having one or more groups selected from the group Z, or a phenyl group optionally having one or more groups selected from the group Y;

a compound represented by Formula (1) in which $R^1$ represents —C(O)W substituted at position 3, W represents —OR$^6$ or —NR$^4$R$^8$, $R^2$ represents a cyano group, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocabonyl group, $-NR^9R^{10}$, $-S(O)_2NR^4R^9$, $-OR^9$, $-S(O)_mR^9$, or $-SF_5$, $R^4$ represents a C1-C6 alkyl group optionally having one or more halogen atoms, a phenyl group optionally having one or more groups selected from the group Y, or a hydrogen atom, $R^6$ represents a hydrogen atom, a C1-C6 alkyl group optionally having one or more groups selected from the group Z, or a phenyl group optionally having one or more groups selected from the group Y, and $R^8$ represents a hydrogen atom;

a compound represented by Formula (1) in which $R^1$ represents $-C(O)W$ substituted at position 3, W represents $-ON=CR^4R^5$ or $-OR^6$, $R^2$ represents a cyano group, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocabonyl group, $-NR^9R^{10}$, $-S(O)_2NR^4R^9$, $-OR^9$, $-S(O)_mR^9$, or $-SF_5$, and $R^6$ represents a hydrogen atom or a C1-C6 alkyl group optionally having one or more groups selected from the group Z;

a compound represented by Formula (1) in which $R^1$ represents $-C(O)W$ substituted at position 3, W represents $-OR^6$ or $-NR^4R^8$, $R^2$ represents a cyano group, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocabonyl group, $-NR^9R^{10}$, $-S(O)_2NR^4R^9$, $-OR^9$, $-S(O)_mR^9$, or $-SF_5$, $R^4$ represents a C1-C6 alkyl group optionally having one or more halogen atoms or a hydrogen atom, $R^6$ represents a hydrogen atom or a C1-C6 alkyl group optionally having one or more groups selected from the group Z, and $R^8$ represents a hydrogen atom;

a compound represented by Formula (1) in which $R^1$ represents $-C(O)W$ substituted at position 3, W represents $-ON=CR^4R^5$ or $-OR^6$, $R^2$ represents a cyano group, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocabonyl group, $-NR^9R^{10}$, $-S(O)_2NR^4R^9$, $-OR^9$, $-S(O)_mR^9$, or $-SF_5$, and $R^6$ represents a hydrogen atom or a C1-C6 alkyl group;

a compound represented by Formula (1) in which $R^1$ represents $-C(O)W$ substituted at position 3, W represents $-OR^6$ or $-NR^4R^8$, $R^2$ represents a cyano group, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocabonyl group, $-NR^9R^{10}$, $-S(O)_2NR^4R^9$, $-OR^9$, $-S(O)_mR^9$, or $-SF_5$, $R^4$ represents a C1-C6 alkyl group or a hydrogen atom, $R^6$ represents a hydrogen atom or a C1-C6 alkyl group, and $R^8$ represents a hydrogen atom;

a compound represented by Formula (1) in which $R^1$ represents $-C(O)W$ substituted at position 3, W represents $-OR^6$, $R^2$ represents a cyano group, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocabonyl group, $-NR^9R^{10}$, $-S(O)_2NR^4R^9$, $-OR^9$, $-S(O)_mR^9$, or $-SF_5$, and R⁶ represents a hydrogen atom;
a compound represented by Formula (1) in which R¹ represents —C(O)W substituted at position 3,
W represents —OR⁶,
R² represents a cyano group, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocabonyl group, —NR⁹R¹⁰, —S(O)₂NR⁴R⁹, —OR⁹, —S(O)ₘR⁹, or —SF₅,
R⁶ represents a hydrogen atom, and
n represents 1;
a compound represented by Formula (1) in which R¹ represents —C(O)W substituted at position 3,
W represents —OR⁶,
R² represents a cyano group, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocabonyl group, —NR⁹R¹⁰, —S(O)₂NR⁴R⁹, —OR⁹, —S(O)ₘR⁹, or —SF₅,
R⁶ represents a C1-C6 alkyl group, and
n represents 1 or 2;
a compound represented by Formula (1) in which R¹ represents —C(O)W substituted at position 3,
W represents —OR⁶,
R² represents a cyano group, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocabonyl group, —NR⁹R¹⁰, —S(O)₂NR⁴R⁹, —OR⁹, —S(O)ₘR⁹, or —SF₅,
R⁶ represents a methyl group or an ethyl group, and
n represents 1 or 2;

a compound represented by Formula (1) in which R¹ represents —C(O)W substituted at position 3,
W represents —OR⁶,
R² represents a cyano group, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocabonyl group, —NR⁹R¹⁰, —S(O)₂NR⁴R⁹, —OR⁹, —S(O)ₘR⁹, or —SF₅,
R⁶ represents a hydrogen atom, and
n represents 1 or 2;
a compound represented by Formula (1) in which R¹ represents —C(O)W substituted at position 3,
W represents —OR⁶,
R² represents a cyano group, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocabonyl group, —NR⁹R¹⁰, —S(O)₂NR⁴R⁹, —OR⁹, —S(O)ₘR⁹, or —SF₅,
R⁶ represents a C1-C6 alkyl group, and
n represents 1;
a compound represented by Formula (1) in which R¹ represents —C(O)W substituted at position 3,
W represents —OR⁶,
R² represents a cyano group, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocabonyl group, —NR⁹R¹⁰, —S(O)₂NR⁴R⁹, —OR⁹, —S(O)ₘR⁹, or —SF₅, R⁶ represents a methyl group or an ethyl group, and n represents 1;

a compound represented by Formula (1) in which R¹ represents —C(O)W substituted at position 3, W represents —OR⁶, R² represents a cyano group, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocabonyl group, —NR⁹R¹⁰, —S(O)₂NR⁴R⁹, OR⁹, —S(O)ₘR⁹, or —SF₅, R⁶ represents a hydrogen atom, and n represents 1;

a compound represented by Formula (1) in which R¹ represents —C(O)W substituted at position 3, W represents —OR⁶, R² represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —OR⁹, or —S(O)ₘR⁹, R⁶ represents a C1-C6 alkyl group, and n represents 1 or 2;

a compound represented by Formula (1) in which R¹ represents —C(O)W substituted at position 3, W represents —OR⁶, R² represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —OR⁹, or —S(O)ₘR⁹, R⁶ represents a methyl group or an ethyl group, and n represents 1 or 2;

a compound represented by Formula (1) in which R¹ represents —C(O)W substituted at position 3, W represents —OR⁶, R² represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —OR⁹, or —S(O)ₘR⁹, R⁶ represents a hydrogen atom, and n represents 1 or 2;

a compound represented by Formula (1) in which R¹ represents —C(O)W substituted at position 3, W represents —OR⁶, R² represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —OR⁹, or —S(O)ₘR⁹, R⁶ represents a C1-C6 alkyl group, and n represents 1;

a compound represented by Formula (1) in which R¹ represents —C(O)W substituted at position 3, W represents —OR⁶, R² represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —OR⁹, or —S(O)ₘR⁹, R⁶ represents a methyl group or an ethyl group, and n represents 1;

a compound represented by Formula (1) in which R¹ represents —C(O)W substituted at position 3, W represents —OR⁶, R² represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —OR⁹, or —S(O)ₘR⁹, R⁶ represents a hydrogen atom, and n represents 1;

a compound represented by Formula (1) in which R¹ represents —C(O)W substituted at position 3, W represents —OR⁶, R⁶ represents a hydrogen atom, a methyl group, or an ethyl group, and n represents 0;

a compound represented by Formula (1) in which R¹ represents —C(O)W substituted at position 3, W represents —OR⁶, R³ represents a hydrogen atom or a C1-C6 alkyl group optionally having one or more groups selected from the group X, R⁶ represents a hydrogen atom, a methyl group, or an ethyl group, and n represents 0;

a compound represented by Formula (1) in which R¹ represents —C(O)W substituted at position 3, W represents —OR⁶, R³ represents a hydrogen atom or a trifluoromethyl group, R⁶ represents a hydrogen atom, a methyl group, or an ethyl group, and n represents 0;

a compound represented by Formula (1) in which R¹ represents —C(O)W substituted at position 3, W represents —OR⁶, R³ represents a hydrogen atom or a trifluoromethyl group, R⁶ represents a hydrogen atom or a C1-C6 alkyl group, and n represents 0;

a compound represented by Formula (1) in which R¹ represents —C(O)W substituted at position 3, W represents —ON═CR⁴R⁵ or —OR⁶, R³ represents a hydrogen atom or a trifluoromethyl group, R⁶ represents a hydrogen atom or a C1-C6 alkyl group, and n represents 0;

a compound represented by Formula (1) in which R¹ represents —C(O)W substituted at position 3, R³ represents a hydrogen atom or a trifluoromethyl group, R⁶ represents a hydrogen atom or a C1-C6 alkyl group, and n represents 0;

a compound represented by Formula (1) in which $R^1$ represents —C(O)W substituted at position 3, W represents —OR⁶, R² represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —OR⁹, or —S(O)$_m$R⁹, R⁶ represents a hydrogen atom or a C1-C6 alkyl group, and n represents 1;

a compound represented by Formula (1) in which $R^1$ represents —C(O)W substituted at position 3, W represents —OR⁶, R² represents a cyano group, a halogen atom, a nitro group, a methyl group, a tert-butyl group, a trifluoromethyl group, a difluoromethyl group, a pentafluoroethyl group, a phenyl group optionally having one or more groups selected from the group Y, a methoxycarbonyl group, a methoxy group, an ethoxy group, a trifluoromethoxy group, a difluoromethoxy group, a methylthio group, a methylsulfinyl group, a methylsulfonyl group, a trifluoromethylthio group, a trifluoromethylsulfinyl group, or a trifluoromethylsulfonyl group, R⁶ represents a methyl group or an ethyl group, and n represents 1;

a compound represented by Formula (1) in which $R^1$ represents —C(O)W substituted at position 3, W represents —OR⁶, R² represents a cyano group, a halogen atom, a nitro group, a methyl group, a tert-butyl group, a trifluoromethyl group, a difluoromethyl group, a pentafluoroethyl group, a phenyl group optionally having one Or more groups selected from the group Y, a methoxy group, an ethoxy group, a trifluoromethoxy group, a difluoromethoxy group, a methylthio group, a methylsulfinyl group, a methylsulfonyl group, a trifluoromethylthio group, a trifluoromethylsulfinyl group, or a trifluoromethylsulfonyl group, R⁶ represents a hydrogen atom, and n represents 1;

a compound represented by Formula (1) in which $R^1$ represents —C(O)W substituted at position 3, W represents —OR⁶, R² represents a cyano group, a halogen atom, a nitro group, a methyl group, a tert-butyl group, a trifluoromethyl group, a phenyl group optionally having one or more groups selected from the group Y, a methoxycarbonyl group, a methoxy group, or a trifluoromethoxy group, R⁶ represents a methyl group or an ethyl group, and n represents 1;

a compound represented by Formula (1) in which $R^1$ represents —C(O)W substituted at position 3, W represents —OR⁶, R² represents a cyano group, a halogen atom, a nitro group, a methyl group, a tert-butyl group, a trifluoromethyl group, a phenyl group optionally having one or more groups selected from the group Y, a methoxy group, or a trifluoromethoxy group, R⁶ represents a hydrogen atom, and n represents 1;

a compound represented by Formula (1) in which $R^1$ represents —C(O)W substituted at position 3, W represents —OR⁶, R² represents a trifluoromethyl group or a methoxycarbonyl group, R⁶ represents a methyl group or an ethyl group, and n represents 1;

a compound represented by Formula (1) in which $R^1$ represents —C(O)W substituted at position 3, W represents —OR⁶, R² represents a trifluoromethyl group, R⁶ represents a methyl group or an ethyl group, and n represents 1;

a compound represented by Formula (1) in which $R^1$ represents —C(O)W substituted at position 3, W represents —OR⁶, R² represents a trifluoromethyl group, R⁶ represents a hydrogen atom, and n represents 1;

a compound represented by Formula (1) in which $R^1$ represents —C(O)W substituted at position 3, R² represents a cyano group, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocabonyl group, —NR⁹R¹⁰, —S(O)₂NR⁴R⁹, —OR⁹, —S(O)$_m$R⁹, or —SF₅, and R³ represents a hydrogen atom or a C1-C6 alkyl group optionally having one or more groups selected from the group X;

a compound represented by Formula (1) in which $R^1$ represents —C(O)W substituted at position 3, W represents —ON=CR⁴R⁵ or —OR⁶, R² represents a cyano group, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocabonyl group, —NR⁹R¹⁰, —S(O)₂NR⁴R⁹, —OR⁹, —S(O)$_m$R⁹, or —SF₅, and R³ represents a hydrogen atom or a C1-C6 alkyl group optionally having one or more groups selected from the group X;

a compound represented by Formula (1) in which R¹ represents —C(O)W substituted at position 3, W represents —OR⁶ or —NR⁴R⁸, R² represents a cyano group, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocabonyl group, —NR⁹R¹⁰, —S(O)₂NR⁴R⁹, —OR⁹, —S(O)ₘR⁹, or —SF₅, and R³ represents a hydrogen atom or a C1-C6 alkyl group optionally having one or more groups selected from the group X;

a compound represented by Formula (1) in which R¹ represents —C(O)W substituted at position 3, W represents —ON=CR⁴R⁵ or —OR⁶, R² represents a cyano group, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocabonyl group, —NR⁹R¹⁰, —S(O)₂NR⁴R⁹, —OR⁹, —S(O)ₘR⁹, or —SF₅, R³ represents a hydrogen atom or a C1-C6 alkyl group optionally having one or more groups selected from the group X, and n represents 0 or 1;

a compound represented by Formula (1) in which R¹ represents —C(O)W substituted at position 3, W represents —OR⁶ or —NR⁴R⁸, R² represents a cyano group, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocabonyl group, —NR⁹R¹⁰, —S(O)₂NR⁴R⁹, —OR⁹, —S(O)ₘR⁹, or —SF₅, R³ represents a hydrogen atom or a C1-C6 alkyl group optionally having one or more groups selected from the group X, and n represents 0 or 1;

a compound represented by Formula (1) in which R¹ represents —C(O)W substituted at position 3, W represents —ON=CR⁴R⁵ or —OR⁶, R² represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —OR⁹, or —S(O)ₘR⁹, R³ represents a hydrogen atom or a C1-C6 alkyl group optionally having one or more groups selected from the group X, and n represents 0 or 1;

a compound represented by Formula (1) in which R¹ represents —C(O)W substituted at position 3, W represents —OR⁶ or —NR⁴R⁸, R² represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —OR⁹, or —S(O)ₘR⁹, R³ represents a hydrogen atom or a C1-C6 alkyl group optionally having one or more groups selected from the group X, and n represents 0 or 1;

a compound represented by Formula (1) in which R¹ represents —C(O)W substituted at position 3, W represents —OR⁶, R² represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —OR⁹, or —S(O)ₘR⁹, R³ represents a hydrogen atom or a C1-C6 alkyl group optionally having one or more groups selected from the group X, R⁶ represents a hydrogen atom, a C1-C6 alkyl group optionally having one or more groups selected from the group Z, a C3-C6 alkenyl group optionally having one or more groups selected from the group X, a C3-C6 alkynyl group optionally having one or more groups selected from the group X, or a phenyl group optionally having one or more groups selected from the group Y, and n represents 1;

a compound represented by Formula (1) in which R¹ represents —C(O)W substituted at position 3, W represents —OR⁶, R² represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —OR⁹, or —S(O)ₘR⁹, R³ represents a hydrogen atom or a C1-C6 alkyl group optionally having one or more groups selected from the group X, R⁶ represents a hydrogen atom, a C1-C6 alkyl group optionally having one or more groups selected from the group Z, or a phenyl group optionally having one or more groups selected from the group Y, and n represents 1;

A compound represented by Formula (1) in which $R^1$ represents —C(O)W substituted at position 3, W represents —$OR^6$, $R^2$ represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —$OR^9$, or —$S(O)_m R^9$, $R^3$ represents a hydrogen atom or a C1-C6 alkyl group optionally having one or more groups selected from the group X, $R^6$ represents a hydrogen atom or a C1-C6 alkyl group optionally having one or more groups selected from the group Z, and n represents 1;

a compound represented by Formula (1) in which $R^1$ represents —C(O)W substituted at position 3, W represents —$OR^6$, $R^2$ represents a cyano group, a halogen atom, a nitro group, a C1-C6 alkyl group optionally having one or more groups selected from the group X, a phenyl group optionally having one or more groups selected from the group Y, —$OR^9$, or —$S(O)_m R^9$, $R^3$ represents a hydrogen atom or a C1-C6 alkyl group optionally having one or more groups selected from the group X, $R^6$ represents a hydrogen atom, and n represents 1;

a compound represented by Formula (1) in which $R^1$ represents —C(O)W substituted at position 3, W represents —$OR^6$, $R^2$ represents a cyano group, a halogen atom, a nitro group, a C1-C6 alkyl group optionally having one or more groups selected from the group X, a phenyl group optionally having one or more groups Selected from the group Y, a C2-C6 alkoxycarbonyl group, —$OR^9$, or —$S(O)_m R^9$, $R^3$ represents a hydrogen atom or a C1-C6 alkyl group optionally having one or more groups selected from the group X, $R^6$ represents a C1-C6 alkyl group optionally having one or more groups selected from the group Z, and n represents 1;

a compound represented by Formula (1) in which $R^1$ represents —C(O)W substituted at position 3, W represents —$OR^6$, $R^2$ represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —$OR^9$, or —$S(O)_m R^9$, $R^3$ represents a hydrogen atom or a C1-C6 alkyl group optionally having one or more groups selected from the group X, $R^6$ represents a C1-C6 alkyl group, and n represents 1;

a compound represented by Formula (1) in which $R^1$ represents —C(O)W substituted at position 3, W represents —$OR^6$, $R^2$ represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —$OR^9$, or —$S(O)_m R^9$, $R^3$ represents a hydrogen atom or a C1-C6 alkyl group optionally having one or more groups selected from the group X, $R^6$ represents a methyl group or an ethyl group, and n represents 1;

a compound represented by Formula (1) in which $R^1$ represents —C(O)W substituted at position 3, W represents —$OR^6$, $R^2$ represents a cyano group, a halogen atom, a nitro group, a methyl group, a tert-butyl group, a trifluoromethyl group, a phenyl group optionally having one or more groups selected from the group Y, a methoxycarbonyl group, a methoxy group, or trifluoromethoxy group, $R^3$ represents a hydrogen atom or a C1-C6 alkyl group optionally having one or more groups selected from the group X, $R^6$ represents a methyl group or an ethyl group, and n represents 1;

a compound represented by Formula (1) in which $R^1$ represents —C(O)W substituted at position 3, W represents —$OR^6$, $R^2$ represents a cyano group, a halogen atom, a nitro group, a methyl group, a tert-butyl group, a trifluoromethyl group, a phenyl group optionally having one or more groups selected from the group Y, a methoxycarbonyl group, a methoxy group, or a trifluoromethoxy group, $R^3$ represents a hydrogen atom, a methyl group, an ethyl group, a trifluoromethyl group, or a pentafluoroethyl group, $R^6$ represents a methyl group or an ethyl group, and n represents 1;

a compound represented by Formula (1) in which $R^1$ represents —C(O)W substituted at position 3, W represents —$OR^6$, $R^2$ represents a cyano group, a halogen atom, a nitro group, a methyl group, a tert-butyl group, a trifluoromethyl group, a phenyl group optionally having one or more groups selected from the group Y, a methoxycarbonyl group, a methoxy group, or a trifluoromethoxy group, $R^3$ represents a hydrogen atom, a methyl group, or a trifluoromethyl group, $R^6$ represents a methyl group or an ethyl group, and n represents 1;

a compound represented by Formula (1) in which $R^1$ represents —C(O)W substituted at position 3, W represents —$OR^6$, $R^2$ represents a trifluoromethyl group or a methoxycarbonyl group, $R^3$ represents a hydrogen atom, a methyl group, or a trifluoromethyl group, $R^6$ represents a methyl group or an ethyl group, and n represents 1;

a compound represented by Formula (1) in which $R^1$ represents —C(O)W substituted at position 3, W represents —$OR^6$, $R^2$ represents a trifluoromethyl group or a methoxycarbonyl group, $R^3$ represents a hydrogen atom or a trifluoromethyl group, $R^6$ represents a methyl group or an ethyl group, and n represents 1;

a compound represented by Formula (1) in which $R^1$ represents —C(O)W substituted at position 3, W represents —OR$^6$,
R$^2$ represents a trifluoromethyl group,
R$^3$ represents a hydrogen atom,
R$^6$ represents a methyl group or an ethyl group, and
n represents 1;
a compound represented by Formula (1) in which R$^1$ represents —C(O)W substituted at position 3,
W represents —OR$^6$,
R$^2$ represents a trifluoromethyl group,
R$^3$ represents a hydrogen atom,
R$^6$ represents a hydrogen atom, and
n represents 1;
a compound represented by Formula (1) in which R$^1$ represents —C(O)W substituted at position 3,
W represents —OR$^6$,
R$^2$ represents a cyano group, a halogen atom, a nitro group, a C1-C6 alkyl group optionally having one or more groups selected from the group X, a phenyl group optionally having one or more groups selected from the group Y, —OR$^9$, or —S(O)$_m$R$^9$,
R$^3$ represents a hydrogen atom,
R$^6$ represents a methyl group or an ethyl group, and
n represents 1 or 2;
a compound represented by Formula (1) in which R$^1$ represents —C(O)W substituted at position 3,
W represents —OR$^6$,
R$^2$ represents a cyano group, a halogen atom, a nitro group, a C1-C6 alkyl group optionally having one or more groups selected from the group X, a phenyl group optionally having one or more groups selected from the group Y, —OR$^9$, or —S(O)$_m$R$^9$,
R$^3$ represents a hydrogen atom,
R$^6$ represents a hydrogen atom, and
n represents 1 or 2;
a compound represented by Formula (1) in which R$^1$ represents —C(O)W substituted at position 3,
W represents —NR$^4$R$^8$,
R$^2$ represents a cyano group, a halogen atom, a nitro group, a C1-C6 alkyl group optionally having one or more groups selected from the group X, a phenyl group optionally having one or more groups selected from the group Y, —OR$^9$, or —S(O)$_m$R$^9$,
R$^3$ represents a hydrogen atom or a trifluoromethyl group, and
n represents 0 or 1;
a compound represented by Formula (1) in which R$^1$ represents —C(O)W substituted at position 3,
W represents —NR$^4$R$^8$,
R$^2$ represents a cyano group, a halogen atom, a nitro group, a C1-C6 alkyl group optionally having one or more groups selected from the group X, a phenyl group optionally having one or more groups selected from the group Y, —OR$^9$, or —S(O)$_m$R$^9$,
R$^3$ represents a hydrogen atom or a trifluoromethyl group,
R$^4$ represents a hydrogen atom, and
n represents 0 or 1;
a compound represented by Formula (1) in which R$^1$ represents —C(O)W substituted at position 3,
W represents —NR$^4$R$^8$,
R$^2$ represents a cyano group, a halogen atom, a nitro group, a C1-C6 alkyl group optionally having one or more groups selected from the group X, a phenyl group optionally having one or more groups selected from the group Y, —OR$^9$, or —S(O)$_m$R$^9$,
R$^3$ represents a hydrogen atom or a trifluoromethyl group,
R$^8$ represents a hydrogen atom, and
n represents 0 or 1;
a compound represented by Formula (1) in which R$^1$ represents —C(O)W substituted at position 3,
W represents —NR$^4$R$^8$,
R$^2$ represents a cyano group, a halogen atom, a nitro group, a C1-C6 alkyl group optionally having one or more groups selected from the group X, a phenyl group optionally having one or more groups selected from the group Y, —OR$^9$, or —S(O)$_m$R$^9$,
R$^3$ represents a hydrogen atom or a trifluoromethyl group,
R$^4$ and R$^8$ represent a hydrogen atom, and
n represents 0 or 1;
a compound represented by Formula (1) in which R$^1$ represents —C(O)W substituted at position 3,
W represents —OR$^6$ or —NR$^4$R$^8$,
R$^2$ represents a C1-C6 alkyl group optionally having one or more groups selected from the group X or a C2-C6 alkoxycarbonyl group,
R$^3$ represents a hydrogen atom or a C1-C6 alkyl group optionally having one or more groups selected from the group X, and
n represents 0 or 1;
a compound represented by Formula (1) in which R$^1$ represents —C(O)W substituted at position 3,
W represents —OR$^6$ or —NR$^4$R$^8$,
R$^2$ represents a trifluoromethyl group or a methoxycarbonyl group,
R$^3$ represents a hydrogen atom or a trifluoromethyl group,
R$^4$ and R$^8$ represent a hydrogen atom,
R$^6$ represents a hydrogen atom, a methyl group, or an ethyl group, and
n represents 0 or 1;
a compound represented by Formula (1) in which R$^1$ represents —C(O)W substituted at position 3,
W represents —OR$^6$ or —NR$^4$R$^8$,
R$^2$ represents a trifluoromethyl group,
R$^3$ represents a hydrogen atom or a trifluoromethyl group,
R$^4$ and R$^8$ represent a hydrogen atom,
R$^6$ represents a hydrogen atom, and
n represents 0 or 1;
a compound represented by Formula (1) in which R$^1$ represents —C(O)W substituted at position 3,
W represents —OR$^6$ or —NR$^4$R$^8$,
R$^2$ represents a trifluoromethyl group,
R$^3$ represents a hydrogen atom or a trifluoromethyl group,
R$^4$ and R$^8$ represent a hydrogen atom,
R$^6$ represents a methyl group or an ethyl group, and
n represents 0 or 1;
a compound represented by Formula (1) in which R$^1$ represents —C(O)W substituted at position 4, and
n represents 0, 1, or 2;
a compound represented by Formula (1) in which R$^1$ represents —C(O)W substituted at position 4, and
R$^2$ represents a cyano group, a halogen atom, a nitro group, a C1-C6 alkyl group optionally having one or more groups selected from the group X, a phenyl group optionally having one or more groups selected from the group Y, —OR$^9$, or —S(O)$_m$R$^9$;
a compound represented by Formula, (1) in which R$^1$ represents —C(O)W substituted at position 4, and
R$^3$ represents a hydrogen atom or a C1-C6 alkyl group optionally having one or more groups selected from the group X;
a compound represented by Formula (1) in which R$^1$ represents —C(O)W substituted at position 4, and $R^2$ represents a cyano group, a halogen atom, a nitro group, a C1-C6 alkyl group optionally having one or more groups selected from the group X, a phenyl group optionally having one or more groups selected from the group Y, —$OR^9$, or —$S(O)_mR^9$, and $R^3$ represents a hydrogen atom or a C1-C6 alkyl group optionally having one or more groups selected from the group X;

a compound represented by Formula (1) in which represents —C(O)W substituted at position 4, W represents —$OR^6$ or —$NR^4R^8$, $R^2$ represents a cyano group, a halogen atom, a nitro group, a C1-C6 alkyl group optionally having one or more groups selected from the group X, a phenyl group optionally having one or more groups selected from the group Y, —$OR^9$, or —$S(O)_mR^9$, and $R^3$ represents a hydrogen atom or a C1-C6 alkyl group optionally having one or more groups selected from the group X;

a compound represented by Formula (1) in which $R^1$ represents —C(O)W substituted at position 4, $R^2$ represents a cyano group, a halogen atom, a nitro group, a C1-C6 alkyl group optionally having one or more groups selected from the group X, a phenyl group optionally having one or more groups selected from the group Y, —$OR^9$, or —$S(O)_mR^9$, $R^3$ represents a hydrogen atom or a C1-C6 alkyl group optionally having one or more groups selected from the group X, and n represents 0 or 1;

a compound represented by Formula (1) in which $R^1$ represents —C(O)W substituted at position 4, $R^2$ represents a cyano group, a halogen atom, a nitro group, a C1-C6 alkyl group optionally having one or more groups selected from the group X, a phenyl group optionally having one or more groups selected from the group Y, —$OR^9$, or —$S(O)_mR^9$, $R^3$ represents a hydrogen atom or a trifluoromethyl group, and n represents 0 or 1;

a compound represented by Formula (1) in which $R^1$ represents —C(O)W substituted at position 4, W represents —$NR^4R^8$, $R^2$ represents a cyano group, a halogen atom, a nitro group, a C1-C6 alkyl group optionally having one or more groups selected from the group X, a phenyl group optionally having one or more groups selected from the group Y, —$OR^9$, or —$S(O)_mR^9$, $R^3$ represents a hydrogen atom or a trifluoromethyl group, and n represents 0 or 1;

a compound represented by Formula (1) in which $R^1$ represents —C(O)W substituted at position 4, W represents —$NR^4R^8$, $R^2$ represents a cyano group, a halogen atom, a nitro group, a C1-C6 alkyl group optionally having one or more groups selected from the group X, a phenyl group optionally having one or more groups selected from the group Y, —$OR^9$, or —$S(O)_mR^9$, $R^3$ represents a hydrogen atom or a trifluoromethyl group, $R^4$ represents a hydrogen atom, and n represents 0 or 1;

a compound represented by Formula (1) in which $R^1$ represents —C(O)W substituted at position 4, W represents —$NR^4R^8$, $R^2$ represents a cyano group, a halogen atom, a nitro group, a C1-C6 alkyl group optionally having one or more groups selected from the group X, a phenyl group optionally having one or more groups selected from the group Y, —$OR^9$, or —$S(O)_mR^9$, $R^3$ represents a hydrogen atom or a trifluoromethyl group, $R^8$ represents a hydrogen atom, and n represents 0 or 1;

a compound represented by Formula (1) in which $R^1$ represents —C(O)W substituted at position 4, W represents —$NR^4R^8$, $R^2$ represents a cyano group, a halogen atom, a nitro group, a C1-C6 alkyl group optionally having one or more groups selected from the group X, a phenyl group optionally having one or more groups selected from the group Y, —$OR^9$, or —$S(O)_mR^9$, $R^3$ represents a hydrogen atom or a trifluoromethyl group, $R^4$ and $R^8$ represent a hydrogen atom, and n represents 0 or 1;

a compound represented by Formula (1) in which $R^1$ represents —C(O)W substituted at position 4, W represents —ON=$CR^4R^5$ or —$OR^6$, $R^2$ represents a cyano group, a halogen atom, a nitro group, a C1-C6 alkyl group optionally having one or more groups selected from the group X, a phenyl group optionally having one or more groups selected from the group Y, —$OR^9$, or —$S(O)_mR^9$, $R^3$ represents a hydrogen atom or a trifluoromethyl group, and n represents 0 or 1;

a compound represented by Formula (1) in which $R^1$ represents —C(O)W substituted at position 4, W represents —$OR^6$, $R^2$ represents a cyano group, a halogen atom, a nitro group, a C1-C6 alkyl group optionally having one or more groups selected from the group X, a phenyl group optionally having one or more groups selected from the group Y, —$OR^9$, or —$S(O)_mR^9$, $R^3$ represents a hydrogen atom or a trifluoromethyl group, $R^6$ represents a C1-C6 alkyl group, and n represents 0 or 1;

a compound represented by Formula (1) in which $R^1$ represents —C(O)W substituted at position 4, W represents —$OR^6$, $R^2$ represents a cyano group, a halogen atom, a nitro group, a C1-C6 alkyl group optionally having one or more groups selected from the group X, a phenyl group optionally having one or more groups selected from the group Y, —$OR^9$, or —$S(O)_mR^9$, $R^3$ represents a hydrogen atom or a trifluoromethyl group, $R^6$ represents a methyl group or an ethyl group, and n represents 0 or 1;

a compound represented by Formula (1) in which $R^1$ represents —C(O)W substituted at position 4, W represents —$OR^6$, $R^2$ represents a C1-C6 alkyl group optionally having one or more groups selected from the group X, $R^3$ represents a hydrogen atom or a trifluoromethyl group, $R^6$ represents a methyl group or an ethyl group, and n represents 1;

a compound represented by Formula (1) in which $R^1$ represents —C(O)W substituted at position 4, W represents —$OR^6$ or —$NR^4R^8$, $R^3$ represents a hydrogen atom or a trifluoromethyl group, $R^6$ represents a methyl group or an ethyl group, and n represents 0;

a compound represented by Formula (1) in which $R^1$ represents —C(O)W substituted at position 4,
W represents —$OR^6$,
$R^3$ represents a hydrogen atom or a trifluoromethyl group,
$R^6$ represents a methyl group or an ethyl group, and
n represents 0;
a compound represented by Formula (1) in which $R^1$ represents —C(O)W substituted at position 4,
W represents —$OR^6$ or —$NR^4R^8$,
$R^2$ represents a trifluoromethyl group,
$R^3$ represents a hydrogen atom or a trifluoromethyl group,
$R^4$ and $R^8$ represent a hydrogen atom,
$R^6$ represents a hydrogen atom, and
n represents 0 or 1;
a compound represented by Formula (1) in which $R^1$ represents —C(O)W substituted at position 4,
W represents —$OR^6$ or —$NR^4R^8$,
$R^2$ represents a trifluoromethyl group,
$R^3$ represents a hydrogen atom or a trifluoromethyl group,
$R^4$ and $R^8$ represent a hydrogen atom,
$R^6$ represents a methyl group or an ethyl group, and
n represents 0 or 1;
a compound represented by Formula (1) in which $R^1$ represents —C(O)W substituted at position 5, and
n represents 0, 1, or 2;
a compound represented by Formula (1) in which $R^1$ represents —C(O)W substituted at position 5, and
$R^2$ represents a cyano group, a halogen atom, a nitro group, a C1-C6 alkyl group optionally having one or more groups selected from the group X, a phenyl group optionally having one or more groups selected from the group Y, —$OR^9$, or —$S(O)_mR^9$;
a compound represented by Formula (1) in which $R^1$ represents —C(O)W substituted at position 5, and
$R^3$ represents a hydrogen atom or a C1-C6 alkyl group optionally having one or more groups selected from the group X;
a compound represented by Formula (1) in which $R^1$ represents —C(O)W substituted at position 5,
$R^2$ represents a cyano group, a halogen atom, a nitro group, a C1-C6 alkyl group optionally having one or more groups selected from the group X, a phenyl group optionally having one or more groups selected from the group Y, —$OR^9$, or —$S(O)_mR^9$, and
$R^3$ represents a hydrogen atom or a C1-C6 alkyl group optionally having one or more groups selected from the group X;
a compound represented by Formula (1) in which $R^1$ represents —C(O)W substituted at position 5,
W represents —$OR^6$ or —$NR^4R^8$,
$R^2$ represents a cyano group, a halogen atom, a nitro group, a C1-C6 alkyl group optionally having one or more groups selected from the group X, a phenyl group optionally having one or more groups selected from the group Y, —$OR^9$, or —$S(O)_mR^9$, and
$R^3$ represents a hydrogen atom or a C1-C6 alkyl group optionally having one or more groups selected from the group X;
a compound represented by Formula (1) in which $R^1$ represents —C(O)W substituted at position 5,
$R^2$ represents a cyano group, a halogen atom, a nitro group, a C1-C6 alkyl group optionally having one or more groups selected from the group X, a phenyl group optionally having one or more groups selected from the group Y, —$OR^9$, or —$S(O)_mR^9$, $R^3$ represents a hydrogen atom or a C1-C6 alkyl group optionally having one or more groups selected from the group X, and
n represents 0 or 1;
a compound represented by Formula (1) in which $R^1$ represents —C(O)W substituted at position 5,
$R^2$ represents a cyano group, a halogen atom, a nitro group, a C1-C6 alkyl group optionally having one or more groups selected from the group X, a phenyl group optionally having one or more groups selected from the group Y, —$OR^9$, or —$S(O)_mR^9$,
$R^3$ represents a hydrogen atom or a trifluoromethyl group, and
n represents 0 or 1;
a compound represented by Formula (1) in which $R^1$ represents —C(O)W substituted at position 5,
W represents —$NR^4R^8$,
$R^2$ represents a cyano group, a halogen atom, a nitro group, a C1-C6 alkyl group optionally having one or more groups selected from the group X, a phenyl group optionally having one or more groups selected from the group Y, —$OR^9$, or —$S(O)_mR^9$,
$R^3$ represents a hydrogen atom or a trifluoromethyl group, and
n represents 0 or 1;
a compound represented by Formula (1) in which $R^1$ represents —C(O)W substituted at position 5,
W represents —$NR^4R^8$,
$R^2$ represents a cyano group, a halogen atom, a nitro group, a C1-C6 alkyl group optionally having one or more groups selected from the group X, a phenyl group optionally having one or more groups selected from the group Y, —$OR^9$, or —$S(O)_mR^9$,
$R^3$ represents a hydrogen atom or a trifluoromethyl group,
$R^4$ represents a hydrogen atom, and
n represents 0 or 1;
a compound represented by Formula (1) in which $R^1$ represents —C(O)W substituted at position 5,
W represents —$NR^4R^8$,
$R^2$ represents a cyano group, a halogen atom, a nitro group, a C1-C6 alkyl group optionally having one or more groups selected from the group X, a phenyl group optionally having one or more groups selected from the group Y, —$OR^9$, or —$S(O)_mR^9$,
$R^3$ represents a hydrogen atom or a trifluoromethyl group,
$R^8$ represents a hydrogen atom, and
n represents 0 or 1;
a compound represented by Formula (1) in which $R^1$ represents —C(O)W substituted at position 5,
W represents —$NR^4R^8$,
$R^2$ represents a cyano group, a halogen atom, a nitro group, a C1-C6 alkyl group optionally having one or more groups selected from the group X, a phenyl group optionally having one or more groups selected from the group Y, —$OR^9$, or —$S(O)_mR^9$,
$R^3$ represents a hydrogen atom or a trifluoromethyl group,
$R^4$ and $R^8$ represent a hydrogen atom, and
n represents 0 or 1;
a compound represented by Formula (1) in which $R^1$ represents —C(O)W substituted at position 5,
W represents —ON=$CR^4R^5$ or —$OR^6$,
$R^2$ represents a cyano group, a halogen atom, a nitro group, a C1-C6 alkyl group optionally having one or more groups selected from the group X, a phenyl group optionally having one or more groups selected from the group Y, —$OR^9$, or —$S(O)_mR^9$, R³ represents a hydrogen atom or a trifluoromethyl group, and n represents 0 or 1;

a compound represented by Formula (1) in which R¹ represents —C(O)W substituted at position 5, W represents —OR⁶, R² represents a cyano group, a halogen atom, a nitro group, a C1-C6 alkyl group optionally having one or more groups selected from the group X, a phenyl group optionally having one or more groups selected from the group Y, —OR⁹, or —S(O)$_m$R⁹, R³ represents a hydrogen atom or a trifluoromethyl group, R⁶ represents a C1-C6 alkyl group, and n represents 0 or 1;

a compound represented by Formula (1) in which R¹ represents —C(O)W substituted at position 5, W represents —OR⁶, R² represents a cyano group, a halogen atom, a nitro group, a C1-C6 alkyl group optionally having one or more groups selected from the group X, a phenyl group optionally having one or more groups selected from the group Y, —OR⁹, or —S(O)$_m$R⁹, R³ represents a hydrogen atom or a trifluoromethyl group, R⁶ represents a methyl group or an ethyl group, and n represents 0 or 1;

a compound represented by Formula (1) in which R¹ represents —C(O)W substituted at position 5, W represents —OR⁶, R² represents a C1-C6 alkyl group optionally having one or more groups selected from the group X, R³ represents a hydrogen atom or a trifluoromethyl group, R⁶ represents a methyl group or an ethyl group, and n represents 1;

a compound represented by Formula (1) in which R¹ represents —C(O)W substituted at position 5, W represents —OR⁶ or —NR⁴R⁸, R³ represents a hydrogen atom or a trifluoromethyl group, R⁶ represents a methyl group or an ethyl group, and n represents 0;

a compound represented by Formula (1) in which R¹ represents —C(O)W substituted at position 5, W represents —OR⁶, R³ represents a hydrogen atom or a trifluoromethyl group, R⁶ represents a methyl group or an ethyl group, and n represents 0;

a compound represented by Formula (1) in which R¹ represents —C(O)W substituted at position 5, W represents —OR⁶ or —NR⁴R⁸, R² represents a trifluoromethyl group, R³ represents a hydrogen atom or a trifluoromethyl group, R⁴ and R⁸ represent a hydrogen atom, R⁶ represents a hydrogen atom, and n represents 0 or 1;

a compound represented by Formula (1) in which R¹ represents —C(O)W substituted at position 5, W represents —OR⁶ or —NR⁴R⁸, R² represents a trifluoromethyl group, R³ represents a hydrogen atom or a trifluoromethyl group, R⁴ and R⁸ represent a hydrogen atom, R⁶ represents a methyl group or an ethyl group, and n represents 0 or 1;

a compound represented by Formula (1) in which R¹ represents —C(O)W substituted at position 6, and n represents 0, 1, or 2;

a compound represented by Formula (1) in which R¹ represents —C(O)W substituted at position 6, and R² represents a cyano group, a halogen atom, a nitro group, a C1-C6 alkyl group optionally having one or more groups selected from the group X, a phenyl group optionally having one or more groups selected from the group Y, —OR⁹, or —S(O)$_m$R⁹;

a compound represented by Formula (1) in which R¹ represents —C(O)W substituted at position 6, and R³ represents a hydrogen atom or a C1-C6 alkyl group optionally having one or more groups selected from the group X;

a compound represented by Formula (1) in which R¹ represents —C(O)W substituted at position 6, R² represents a cyano group, a halogen atom, a nitro group, a C1-C6 alkyl group optionally having one or more groups selected from the group X, a phenyl group optionally having one or more groups selected from the group Y, —OR⁹, or —S(O)$_m$R⁹; and R³ represents a hydrogen atom or a C1-C6 alkyl group optionally having one or more groups selected from the group X;

a compound represented by Formula (1) in which R¹ represents —C(O)W substituted at position 6, W represents —OR⁶ or —NR⁴R⁸, R² represents a cyano group, a halogen atom, a nitro group, a C1-C6 alkyl group optionally having one or more groups selected from the group X, a phenyl group optionally having one or more groups selected from the group Y, —OR⁹, or —S(O)$_m$R⁹; and R³ represents a hydrogen atom or a C1-C6 alkyl group optionally having one or more groups selected from the group X;

a compound represented by Formula (1) in which R¹ represents —C(O)W substituted at position 6, R² represents a cyano group, a halogen atom, a nitro group, a C1-C6 alkyl group optionally having one or more groups selected from the group X, a phenyl group optionally having one or more groups selected from the group Y, —OR⁹, or —S(O)$_m$R⁹;

R³ represents a hydrogen atom or a C1-C6 alkyl group optionally having one or more groups selected from the group X, and n represents 0 or 1;

a compound represented by Formula (1) in which R¹ represents —C(O)W substituted at position 6, R² represents a cyano group, a halogen atom, a nitro group, a C1-C6 alkyl group optionally having one or more groups selected from the group X, a phenyl group optionally having one or more groups selected from the group Y, —OR⁹, or —S(O)$_m$R⁹;

R³ represents a hydrogen atom or a trifluoromethyl group, and n represents 0 or 1;

a compound represented by Formula (1) in which R¹ represents —C(O)W substituted at position 6, W represents —NR⁴R⁸, R² represents a cyano group, a halogen atom, a nitro group, a C1-C6 alkyl group optionally having one or more groups selected from the group X, a phenyl group optionally having one or more groups selected from the group Y, —OR⁹, or —S(O)$_m$R⁹;

R³ represents a hydrogen atom or a trifluoromethyl group, and
n represents 0 or 1;
a compound represented by Formula (1) in which R¹ represents —C(O)W substituted at position 6,
W represents —NR⁴R⁸,
R² represents a cyano group, a halogen atom, a nitro group, a C1-C6 alkyl group optionally having one or more groups selected from the group X, a phenyl group optionally having one or more groups selected from the group Y, —OR⁹, or —S(O)$_m$R⁹;
R³ represents a hydrogen atom or a trifluoromethyl group,
R⁴ represents a hydrogen atom, and
n represents 0 or 1;
a compound represented by Formula (1) in which R¹ represents —C(O)W substituted at position 6,
W represents —NR⁴R⁸,
R² represents a cyano group, a halogen atom, a nitro group, a C1-C6 alkyl group optionally having one or more groups selected from the group X, a phenyl group optionally having one or more groups selected from the group Y, —OR⁹, or —S(O)$_m$R⁹;
R³ represents a hydrogen atom or a trifluoromethyl group,
R⁸ represents a hydrogen atom, and
n represents 0 or 1;
a compound represented by Formula (1) in which R¹ represents —C(O)W substituted at position 6,
W represents —NR⁴R⁸,
R² represents a cyano group, a halogen atom, a nitro group, a C1-C6 alkyl group optionally having one or more groups selected from the group X, a phenyl group optionally having one or more groups selected from the group Y, —OR⁹, or —S(O)$_m$R⁹;
R³ represents a hydrogen atom or a trifluoromethyl group,
R⁴ and R⁸ represent a hydrogen atom, and
n represents 0 or 1;
a compound represented by Formula (1) in which R¹ represents —C(O)W substituted at position 6,
W represents —ON=CR⁴R⁵ or —OR⁶,
R² represents a cyano group, a halogen atom, a nitro group, a C1-C6 alkyl group optionally having one or more groups selected from the group X, a phenyl group optionally having one or more groups selected from the group Y, —OR⁹, or —S(O)$_m$R⁹;
R³ represents a hydrogen atom or a trifluoromethyl group, and
n represents 0 or 1;
a compound represented by Formula (1) in which R¹ represents —C(O)W substituted at position 6,
W represents —OR⁶,
R² represents a cyano group, a halogen atom, a nitro group, a C1-C6 alkyl group optionally having one or more groups selected from the group X, a phenyl group optionally having one or more groups selected from the group Y, —OR⁹, or —S(O)$_m$R⁹;
R³ represents a hydrogen atom or a trifluoromethyl group,
R⁶ represents a C1-C6 alkyl group, and
n represents 0 or 1;
a compound represented by Formula (1) in which R¹ represents —C(O)W substituted at position 6,
W represents —OR⁶,
R² represents a cyano group, a halogen atom, a nitro group, a C1-C6 alkyl group optionally having one or more groups selected from the group X, a phenyl group optionally having one or more groups selected from the group Y, —OR⁹, or —S(O)$_m$R⁹,
R³ represents a hydrogen atom or a trifluoromethyl group,
R⁶ represents a methyl group or an ethyl group, and
n represents 0 or 1;
a compound represented by Formula (1) in which R¹ represents —C(O)W substituted at position 6,
W represents —OR⁶,
R² represents a C1-C6 alkyl group optionally having one or more groups selected from the group X,
R³ represents a hydrogen atom or a trifluoromethyl group,
R⁶ represents a methyl group or an ethyl group, and
n represents 1;
a compound represented by Formula (1) in which R¹ represents —C(O)W substituted at position 6,
W represents —OR⁶ or —NR⁴R⁸,
R² represents a hydrogen atom or a trifluoromethyl group,
R⁶ represents a methyl group or an ethyl group, and
n represents 0;
a compound represented by Formula (1) in which R¹ represents —C(O)W substituted at position 6,
W represents —OR⁶,
R³ represents a hydrogen atom or a trifluoromethyl group,
R⁶ represents a methyl group or an ethyl group, and
n represents 0;
a compound represented by Formula (1) in which R¹ represents —C(O)W substituted at position 6,
W represents —OR⁶ or —NR⁴R⁸,
R² represents a trifluoromethyl group,
R³ represents a hydrogen atom or a trifluoromethyl group,
R⁴ and R⁸ represent a hydrogen atom,
R⁶ represents a hydrogen atom, and
n represents 0 or 1;
a compound represented by Formula (1) in which R¹ represents —C(O)W substituted at position 6,
W represents —OR⁶ or —NR⁴R⁸,
R² represents a trifluoromethyl group,
R³ represents a hydrogen atom or a trifluoromethyl group,
R⁴ and R⁸ represent a hydrogen atom,
R⁶ represents a methyl group or an ethyl group, and
n represents 0 or 1;
a compound represented by Formula (1) in which R¹ represents —C(O)W substituted at position 7, and
n represents 0, 1, or 2;
a compound represented by Formula (1) in which R¹ represents —C(O)W substituted at position 7, and
R² represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —OR⁹, or —S(O)$_m$R⁹;
a compound represented by Formula (1) in which R¹ represents —C(O)W substituted at position 7, and
R³ represents a hydrogen atom or a C1-C6 alkyl group optionally having one or more groups selected from the group X;
a compound represented by Formula (1) in which R¹ represents —C(O)W substituted at position 7,
R² represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —OR⁹, or —S(O)$_m$R⁹, and
R³ represents a hydrogen atom or a C1-C6 alkyl group optionally having one or more groups selected from the group X;

a compound represented by Formula (1) in which $R^1$ represents —C(O)W substituted at position 7, W represents —OR$^6$ or —NR$^4$R$^8$, $R^2$ represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —OR$^9$, or —S(O)$_m$R$^9$, and $R^3$ represents a hydrogen atom or a C1-C6 alkyl group optionally having one or more groups selected from the group X;

a compound represented by Formula (1) in which $R^1$ represents —C(O)W substituted at position 7, $R^2$ represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —OR$^9$, or —S(O)$_m$R$^9$, and $R^3$ represents a hydrogen atom or a C1-C6 alkyl group optionally having one or more groups selected from the group X, and n represents 0 or 1;

a compound represented by Formula (1) in which $R^1$ represents —C(O)W substituted at position 7, $R^2$ represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —OR$^9$, or —S(O)$_m$R$^9$, $R^3$ represents a hydrogen atom or a trifluoromethyl group, and n represents 0 or 1;

a compound represented by Formula (1) in which $R^1$ represents —C(O)W substituted at position 7, W represents —NR$^4$R$^8$, $R^2$ represents a cyano group, a halogen atom, a nitro group, a C1-C6 alkyl group optionally having one or more groups selected from the group X, a phenyl group optionally having one or more groups selected from the group Y, —OR$^9$, or —S(O)$_m$R$^9$, $R^3$ represents a hydrogen atom or a trifluoromethyl group, and n represents 0 or 1;

a compound represented by Formula (1) in which $R^1$ represents —C(O)W substituted at position 7, W represents —NR$^4$R$^8$, $R^2$ represents a cyano group, a halogen atom, a nitro group, a C1-C6 alkyl group optionally having one or more groups selected from the group X, a phenyl group optionally having one or more groups selected from the group Y, —OR$^9$, or —S(O)$_m$R$^9$, $R^3$ represents a hydrogen atom or a trifluoromethyl group, $R^4$ represents a hydrogen atom, and n represents 0 or 1;

a compound represented by Formula (1) in which $R^1$ represents —C(O)W substituted at position 7, W represents —NR$^4$R$^8$, $R^2$ represents a cyano group, a halogen atom, a nitro group, a C1-C6 alkyl group optionally having one or more groups selected from the group X, a phenyl group optionally having one or more groups selected from the group Y, —OR$^9$, or —S(O)$_m$R$^9$, $R^3$ represents a hydrogen atom or a trifluoromethyl group, $R^8$ represents a hydrogen atom, and n represents 0 or 1;

a compound represented by Formula (1) in which $R^1$ represents —C(O)W substituted at position 7, W represents —NR$^4$R$^8$, $R^2$ represents a cyano group, a halogen atom, a nitro group, a C1-C6 alkyl group optionally having one or more groups selected from the group X, a phenyl group optionally having one or more groups selected from the group Y, —OR$^9$, or —S(O)$_m$R$^9$, $R^3$ represents a hydrogen atom or a trifluoromethyl group, $R^4$ and $R^8$ represent a hydrogen atom, and n represents 0 or 1;

a compound represented by Formula (1) in which $R^1$ represents —C(O)W substituted at position 7, W represents —ON=CR$^4$R$^5$ or —OR$^6$, $R^2$ represents a cyano group, a halogen atom, a nitro group, a C1-C6 alkyl group optionally having one or more groups selected from the group X, a phenyl group optionally having one or more groups selected from the group Y, —OR$^9$, or —S(O)$_m$R$^9$, $R^3$ represents a hydrogen atom or a trifluoromethyl group, and n represents 0 or 1;

a compound represented by Formula (1) in which $R^1$ represents —C(O)W substituted at position 7, W represents —OR$^6$, $R^2$ represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —OR$^9$, or —S(O)$_m$R$^9$, $R^3$ represents a hydrogen atom or a trifluoromethyl group, $R^6$ represents a C1-C6 alkyl group, and n represents 0 or 1;

a compound represented by Formula (1) in which $R^1$ represents —C(O)W substituted at position 7, W represents —OR$^6$, $R^2$ represents a cyano group, a halogen atom, a nitro group, a C1-C6 alkyl group optionally having one or more groups selected from the group X, a phenyl group optionally having one or more groups selected from the group Y, a C2-C6 alkoxycarbonyl group, —OR$^9$, or —S(O)$_m$R$^9$, $R^3$ represents a hydrogen atom or a trifluoromethyl group, $R^6$ represents a methyl group or an ethyl group, and n represents 0 or 1;

a compound represented by Formula (1) in which $R^1$ represents —C(O)W substituted at position 7, W represents —OR$^6$, $R^2$ represents a C1-C6 alkyl group optionally having one or more groups selected from the group X or a C2-C6 alkoxycarbonyl group, $R^3$ represents a hydrogen atom or a trifluoromethyl group, $R^6$ represents a methyl group or an ethyl group, and n represents 1;

a compound represented by Formula (1) in which $R^1$ represents —C(O)W substituted at position 7, W represents —OR$^6$ or —NR$^4$R$^8$, $R^3$ represents a hydrogen atom or a trifluoromethyl group, $R^6$ represents a methyl group or an ethyl group, and n represents 0;

a compound represented by Formula (1) in which $R^1$ represents —C(O)W substituted at position 7, W represents —OR$^6$,
R$^3$ represents a hydrogen atom or a trifluoromethyl group,
R$^6$ represents a methyl group or an ethyl group, and
n represents 0;
a compound represented by Formula (1) in which R$^1$ represents —C(O)W substituted at position 7,
W represents —OR$^6$ or —NR$^4$R$^8$,
R$^2$ represents a trifluoromethyl group,
R$^3$ represents a hydrogen atom or a trifluoromethyl group,
R$^4$ and R$^8$ represent a hydrogen atom,
R$^6$ represents a hydrogen atom, and
n represents 0 or 1;
a compound represented by Formula (1) in which R$^1$ represents —C(O)W substituted at position 7,
W represents —OR$^6$ or —NR$^4$R$^8$,
R$^2$ represents a trifluoromethyl group,
R$^3$ represents a hydrogen atom or a trifluoromethyl group,
R$^4$ and R$^8$ represent a hydrogen atom,
R$^6$ represents a methyl group or an ethyl group, and
n represents 0 or 1;
a compound represented by Formula (1) in which R$^1$ represents —C(O)W,
W represents —OR$^6$ or —NR$^4$R$^8$,
R$^2$ represents a trifluoromethyl group,
R$^3$ represents a hydrogen atom or a trifluoromethyl group,
R$^4$ and R$^8$ represent a hydrogen atom,
R$^6$ represents a hydrogen atom, and
n represents 0 or 1;
a compound represented by Formula (1) in which R$^1$ represents —C(O)W,
W represents —OR$^6$ or —NR$^4$R$^8$,
R$^2$ represents a trifluoromethyl group,
R$^3$ represents a hydrogen atom or a trifluoromethyl group,
R$^4$ and R$^8$ represent a hydrogen atom,
R$^6$ represents hydrogen atom, and
n represents 1;
a compound represented by Formula (1) in which R$^1$ represents —C(O)W,
W represents —OR$^6$ or —NR$^4$R$^8$,
R$^2$ represents a trifluoromethyl group,
R$^3$ represents a hydrogen atom or a trifluoromethyl group,
R$^4$ and R$^8$ represent a hydrogen atom,
R$^6$ represents a methyl group or an ethyl group, and
n represents 0 or 1;

When the compound of the present invention is used in the method of the present invention, only the compound of the present invention may be used. However, as described later, the compound can be used as a composition for promoting plant growth that is formulated using various inactive ingredients (solid carriers, liquid carriers, surfactants, other adjuvant for formulation, and the like).

Examples of the solid carriers used for formulation include fine powdery or granular materials and the like formed of minerals such as kaolin clay, attapulgite clay, bentonite, montmorillonite, Japanese acid clay, pyrophyllite, talc, diatomaceous earth, and calcite, natural organic substances such as corn rachis powder and walnut shell powder, synthetic organic substances such as urea, salts such as calcium carbonate and ammonium sulfate, or synthetic inorganic substances such as synthetic hydrous silicon oxide. Examples of the liquid carriers include aromatic hydrocarbons such as xylene, alkylbenzene, and methylnaphthalene, alcohols such as 2-propanol, ethylene glycol, propylene glycol, and ethylene glycol monoethyl ether, ketones such as acetone, cyclohexanone, and isophorone, plant oil such as soybean oil and cotton seed oil, petroleum-based aliphatic hydrocarbons, esters, dimethylsulfoxide, acetonitrile, water, and the like.

Examples of the surfactants include anionic surfactants such as an alkyl sulfuric acid ester salt, an alkyl aryl sulfonic acid salt, a dialkyl sulfosuccinic acid salt, a polyoxyethylene alkyl aryl ether phosphoric acid ester salt, lignin sulfonic acid salt, and a naphthalene sulfonate formaldehyde polycondensate, nonionic surfactants such as polyoxyethylene alkyl aryl ether, a polyoxyethylene alkyl polyoxypropylene block copolymer, and a sorbitan aliphatic ester, and cationic surfactants such as an alkyl trimethyl ammonium salt.

Examples of other adjuvants for formulation include water-soluble polymers such as polyvinyl alcohol and polyvinyl pyrrolidone, gum Arabic, alginic acid and a salt thereof, polysaccharides such as carboxymethylcellulose (CMC) and xanthan gum, inorganic substances such as aluminum magnesium silicate and alumina sol, preservatives, colorants, and stabilizing agents such as isopropyl acid phosphate (PAP) and BHT.

In the method of the present invention, when a plant is treated with the compound of the present invention, the plant or the plantation thereof is treated with the compound of the present invention at an effective dose. When the plant or the plantation of the plant is treated, it is treated once or plural times with the compound.

Specific examples of the application method of the present invention include treating of the foliage, flower organs, or ear of a plant by means of spraying the compound to the foliage, soil (plantation) treatment that is performed before or after a plant is planted, seed treatment such as seed sterilization, seed soaking, or seed coating, seedling treatment, treating of a bulb such as a seed tuber, and the like.

In the present invention, examples of the treating of the foliage, flower organs, or ears of a plant include a treatment method applying the compound onto the surface of a plant by means of spraying the compound to foliage, stem, and the like. The examples also include a method of performing spraying treatment on flower organs or the entire plant during the flowering period including a pre-flowering stage, a mid-flowering stage, and a post-flowering stage. Moreover, for grain and the like, the examples include a spraying method performed on the ears or the entire plant during the period of ear emergence.

Examples of the soil treatment method in the method of the present invention include spraying to soil, soil incorporation, and drenching soil with liquid chemical (liquid chemical irrigation, soil injection, or liquid chemical dripping). Examples of the place to be treated include planting holes, planting rows, the vicinity of planting holes, the vicinity of planting rows, the entire area of plantation, the vicinity of plantation, inter-row spaces, places under the stem, a ridge between main stems, culture soil, a seedling box, a seedling tray, a seedbed, and the like. The treatment is performed, for example, during a pre-seeding stage, a seeding stage, a stage immediately after seeding, and during the growing period including a seedling raising stage, a pre-planting stage, at a planting stage, and the post-planting stage. Further, in the soil treatment, a plant may be treated with plural kinds of compounds of the present invention at the same time, and a solid fertilizer such as a paste fertilizer containing the compound of the present invention may be applied to the soil. Moreover, the compound of the present invention may be mixed into a liquid for irrigation by means of, for example, by being injected into irrigation facilities (an irrigation tube, an irrigation pipe, a sprinkler, and the like), mixed into a liquid for inter-row space irrigation, or mixed into a hydroponic medium. In addition, the compound of the present invention can be mixed with the liquid for irrigation in advance to perform the treatment by means of, for example, the above irrigation method or other appropriate irrigation methods such as spraying of water and flooding.

In the present invention, the plant seed treated with the compound of the present invention retains the compound of the present invention at an effective dose, in the inside or surface of the plant seed or in the coated portion formed in the circumference of the plant seed. In the method of the present invention, the treating of seeds is a method of treating seeds or bulbs of a plant as a target with the compound of the present invention. Specific examples thereof include spraying treatment in which a suspension of the compound of the present invention is sprayed onto the seed surface or the bulb surface in the form of mist, smearing treatment in which wettable powder, an emulsion, or a flowable agent of the compound of the present invention is used as is or used by being supplemented with a small amount of water so as to coat the seed or bulb, a soaking treatment in which the seeds are soaked into the solution of the present compound for a certain time, film coating, treatment, pellet coating treatment, and the like. Moreover, in the present invention, the plant seeds treated with the compound of the present invention refer to seeds of a plant that have not yet been seeded to soil or a culture medium for cultivation.

In the method of the present invention, examples of the seedling treatment include spraying treatment in which the compound of the present invention is prepared by being diluted with water to yield an appropriate concentration of active ingredients, and the diluted solution is sprayed to the entire seedling, soaking treatment in which the seedling is soaked into the diluted solution, coating treatment in which the compound of the present invention that is prepared as a dust formulation is applied to the entire seedling, and seedling-growing box treatment in which the culture soil that is being used to raise seedling is treated with the compound of the present invention at an effective dose. Moreover, examples of the soil treatment performed before or after seedlings are planted include a method in which a diluted solution, which is prepared by diluting the compound of the present invention with water to yield an appropriate concentration of active ingredients, is sprayed to the seedlings or the surrounding soil after the seedlings are planted, and a method in which the compound of the present invention that is prepared as granules or a solid formulation such as granules is sprayed to the surrounding soil after the seedlings are planted.

Further, the compound of the present invention may be used by being mixed with a hydroponic medium in hydroponic culture, or used as one of medium components in tissue culture. Regarding hydroponic treatment method in the method of the present invention, when the compound is used for hydroponic culture, the compound can be used by being dissolved or suspended in a hydroponic medium for hydroponic culture that is generally used for a horticultural experiment and the like, within a range of a concentration thereof in the medium of 0.001 ppm to 1,000 ppm. Moreover, when the compound is used for tissue culture or cell culture, the compound can be used by being dissolved or suspended in a generally used medium for plant tissue culture, such as Murashige & Scoog medium, or a hydroponic medium such as Hoagland hydroponic culture solution, within a range of a concentration thereof in the medium of 0.001 ppm to 1,000 ppm. In this case, saccharides as a carbon source, various plant hormones, and the like can be appropriately added according to the conventional method.

When the compound of the present invention is used to treat a plant or a place where the plant grows, the amount of the compound used for the treatment varies with the type of plant, the form of formulation, the time of treatment, weather conditions, and the like. However, the amount is generally within a range of 0.1 g to 10,000 g and preferably within a range of 1 g to 1,000 g, in terms of the amount of active ingredients per 10,000 $m^2$. When the compound is mixed with the entire soil, the amount of the compound used for the treatment is generally 0.1 g to 10,000 g and preferably 1 g to 1,000 g, in terms of the amount of active ingredients per 10,000 $m^2$.

The emulsion, wettable powder, flowable agent, microcapsules, and the like are used for the treatment generally by being diluted with water and sprayed. In this case, the concentration of active ingredients is generally within a range of 0.1 ppm to 10,000 ppm, and preferably within a range of 1 ppm to 1,000 ppm. Powder, granules, and the like are generally used as they are without being diluted.

During the seed treatment, a weight of the compound of the present invention per 100 Kg of seeds is generally within a range of 0.01 g to 1,000 g and preferably within a range of 0.1 g to 100 g.

Examples of plants to which the method of the present invention is applicable include the following.

Crops: corn, rice, wheat, barley, rye, oat, sorghum, cotton, soybean, peanut, buckwheat, sugar beet, colza, sunflower, sugar cane, tobacco, hop, and the like Vegetables: vegetables from Solanaceae family (eggplant, tomato, potato, pepper, bell pepper, and the like), vegetables from Cucurbitaceous family (cucumber, squash, zucchini, watermelon, melon, oriental melon, and the like), vegetables from Cruciferous family (radish, turnip, horseradish, kohlrabi, napa cabbage, cabbage, rape, mustard, broccoli, cauliflower, and the like), vegetables from Compositae family (burdock, edible *chrysanthemum*, artichoke, lettuce, and the like), vegetables from Liliceae family (green onion, onion, garlic, asparagus, and the like), vegetables from Apiaceae family (carrot, parsley, celery, parsnip, and the like), vegetables from Chenopodiaceae family (spinach, chard, and the like), vegetables from Lamiaceae family (Japanese basil, mint, basil, and the like), crops from Laguminosae family (pea, common bean, azuki bean, broad bean, chickpea, and the like), strawberry, sweet potato, Japanese yam, taro, konjac, ginger, okra, and the like Fruit trees: pomaceous fruits (apple, pear, European pear, Chinese quince, quince, and the like), stone fruits (peach, plum, nectarine, Japanese apricot, cherry, apricot, prune, and the like), citrus (Citrus unshiu, orange, lemon, lime, grapefruit, and the like), nuts (chestnut, walnut, hazelnut, almond, pistachio, cashew nut, macadamia nut, and the like), berries (blueberry, cranberry, blackberry, raspberry, and the like), grape, persimmon, olive, loquat, banana, coffee, date, coconut, oil palm, and the like Trees other than fruit trees: tea, a mulberry tree, flowering trees (chive, *camellia, hydrangea*, sasanqua, Japanese star anise, cherry, tulip tree, crape myrtle, fragrant olive, and the like), roadside trees (ash, birch, dogwood, *eucalyptus*, gingko, lilac, maple, oak, poplar, *cercis, liquidambar*, plane, Japanese *zelkova*, Japanese arborvitae, fir, southern Japanese hemlock, juniper, pine, spruce, yew, elm, buckeye, and the like), sweet *viburnum*, yew plum pine, Japanese cedar, Japanese cypress, croton, Japanese spindle tree, Japanese *photinia*, and the like Lawn: grasses (*zoysia* grass, *Zoysia Matrella*, and the like), bermuda grasses (*Cynodon Dactylon*, and the like), bentgrasses (wood medowgrass, creeping bentgrass, colonial bent, and the like), bluegrasses (Kentucky bluegrass, *Poa compressa*, and the like), fescues (*Festuca arundinacea, Festuca rubra* L., *Festuca rubra* var. and the like), ryegrasses (*Lolium* multiporum Lam, *Lolium perenne*, and the like), orchardgrass, timothy grass, and the like Others: flowers and ornamental plants (rose, carnation, *chrysanthemum*, Russell prairie gentian, *gypsophila, gerbera*, marigold, *salvia, petunia, verbena*, tulip, aster, gentian, lily, pansy, cyclamen, orchid, lily of valley, lavender, stock, ornamental cabbage, *primula*, poinsettia, *gladiolus*, cattleya, daisy, cymbidium, *begonia*, and the like), biofuel plants (jatropha, safflower, camelinas, switchgrass, *miscanthus*, reed canarygrass, *Arundo donax*, Ambry hemp, cassava, withy, and the like), foliage plants, and the like Examples of plants applicable to the present invention preferably include tea, apple, pear, grape, cherry, peach, nectarine, persimmon, Japanese apricot, plum, soybean, lettuce, cabbage, tomato, eggplant, cucumber, watermelon, melon, common bean, peas, azuki bean, grasses, colza, strawberry, almond, corn, sorghum, broad beans, napa cabbage, potato, peanut, rice, wheat, taro, konjac, Japanese yam, radish, turnip, parsley, oriental melon, okra, ginger, lemon, orange, grapefruit, lime, blueberry, chestnut, hop, basil, more preferably include plants from the Poaceae family or plants from the Solanaceae family, even more preferably include plants from the Poaceae family, and still more preferably include rice, wheat, corn, and the like.

The above "plant" may be a plant into which a gene which imparts herbicide resistance to a plant, a gene which selectively produces toxicity for harmful insects, a gene which imparts disease resistance to a plant, a gene which relieve abiotic stress, and the like have been introduced by gene recombination or cross-breeding, or may be a stacked GM plant composed of plural kinds of combinations of these.

The compound of the present invention may be used simultaneously with an insecticide, a fungicide and a safener for a certain herbicide to treat seeds, or may be applied to the plant simultaneously with the above agents.

In the present invention, the plant to be treated with the compound of the present invention may be a plant that has been or will be exposed to abiotic stress. The degree of the abiotic stress that is indicated by the value of "stress intensity" described in the following formula may be 105 to 200, preferably 110 to 180, and more preferably 120 to 160.

"stress intensity"=100×"one of the plant phenotypes in a plant that has not yet been exposed to abiotic stress conditions"/"one of the plant phenotypes in the above plant that has been exposed to abiotic stress conditions"     Formula (1):

The term "abiotic stress" as used herein means the stress that causes a decline in physiological functions of cells of a plant, when the plant is exposed to an abiotic stress condition, and then deterioration in the physiological state of the plant, leading to its growth inhibition, such as temperature stress, i.e. high-temperature stress or low-temperature stress, water stress, i.e. drought stress or excess water stress, and salt stress. The high-temperature stress refers to the stress that a plant suffers from when the plant is exposed to a temperature higher than the temperature appropriate for the growth or germination of the plant. Specifically, for example, this type of stress can be caused when an average cultivation temperature of the environment in which a plant is cultivated is under condition of 25° C. or higher, more strictly 30° C. or higher, and even more strictly 35° C. or higher. The low-temperature stress refers to the stress that a plant suffers from when the plant is exposed to a temperature lower than the temperature appropriate for the growth or germination of the plant. Specifically, for example, this type of stress can be caused when an average cultivation temperature of the environment in which a plant is cultivated is under condition of 15° C. or lower, more strictly 10° C. or lower, and even more strictly 5° C. or lower. Moreover, the drought stress refers to the stress that a plant suffers from when the water content in soil is reduced by the decrease in precipitation or watering amount, water absorption of the plant is hindered, and the plant is exposed to a water environment that may hinder the growth of the plant. Specifically, for example, this type of stress can be caused when a moisture content of soil in which the plant is cultivated is under the condition of 15% by weight or less, more strictly 10% by weight or less, and even more strictly 7.5% by weight or less which may causes water stress, or a pF value of soil in which the plant is cultured is under the condition of 2.3 or higher, strictly 2.7 or higher, and even more strictly 3.0 or higher, though these values may vary with the type of soil. The excess water stress refers to the stress that a plant suffers from when the plant is exposed to a moistful environment in which a water content in the soil becomes excessive, and the growth of the plant may be hindered. Specifically, for example, this type of stress can be caused when a moisture content of the soil in which the plant is cultivated is under the condition of 30% by weight or more, more strictly 40% by weight or more, and even more strictly 50% by weight or more, or a pF value of the soil in which the plant is cultivated is under the condition of 1.7 or less, strictly 1.0 or less, and even more strictly 0.3 or less, though these values may vary with the type of soil. Further, the pF value of soil can be measured according to the principle described in "Dictionary of Soil•Plant Nutrition•Environment" (TAIYOSHA, CO., LTD., 1994, Matsusaka et al.), pp 61-62, "pF value measurement method". In addition, the salt stress refers to the stress that a plant suffers from when salts accumulate in the soil or hydroponic medium in which plant is cultivated, the osmotic pressure increases, water absorption of the plant is hindered, and accordingly, the plant is exposed to the environment which may hinder the growth of the plant. Specifically, for example, this type of stress can be caused when an osmotic potential resulting from a salt in the soil or hydroponic medium is under the condition of 0.2 MPa (2,400 ppm or more in terms of a NaCl concentration) or higher, strictly 0.25 MPa or higher, and even more strictly 0.30 MPa or higher. The osmotic pressure in soil can be determined based on the following Raoult's equation, by diluting the soil with water and analyzing a salt concentration of the supernatant liquid.

Raoult's equation $\pi(\text{atm}) = cRT$ $R = 0.082 (\text{L·atm/mol·K})$ $T =$ absolute temperature (K)

$c =$ molar concentration of ion (mol/L)

1 atm=0.1 MPa

Production processes of the compound of the present invention will be described below.

The compound of the present invention can be produced according to, for example, the following (Production process 1) to (Production process 5).

(Production Process 1)

Among the compounds of the present invention, a compound in which W represents —$OR^6$ and $R^6$ represents a hydrogen atom can be produced according to, for example, the following scheme.

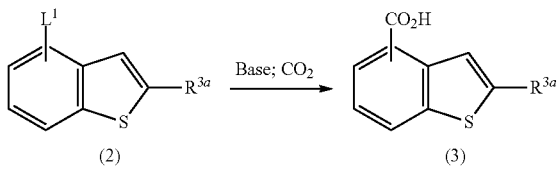

[In the formula, $L^1$ represents a bromine atom or an iodine atom substituted at position 3, 4, 5, 6, or 7, and $R^{3a}$ represents a hydrogen atom or a C1-C6 alkyl group optionally having one or more groups selected from the group X.]

This reaction is generally performed in a solvent. Examples of usable solvents include aromatic hydrocarbons such as benzene, toluene, and xylene; ethers such as diethylether, diisopropylether, 1,4-dioxane, tetrahydrofuran, and dimethoxyethane; and a mixture of these.

Examples of the base used in the present reaction include n-butyllithium, lithium isopropylamide, and the like. In this reaction, the base is used in an amount of 1 molar equivalent to 2 molar equivalents in general, and preferably in an amount of 1 molar equivalent to 1.1 molar equivalents, based on 1 mol of the compound represented by Formula (2).

In this reaction, carbon dioxide is used in an amount of 1 mol or more in general, and preferably in an amount of 10 mol to 1,000 mol, based on 1 mol of the compound represented by Formula (2).

The reaction temperature of this reaction is generally −100° C. to 0° C. and the reaction time of this reaction is generally 5 minutes to 5 hours.

The completion of this reaction can be confirmed by sampling a portion of the reaction mixture and using analysis means such as thin-layer chromatography and high-performance liquid chromatography. After this reaction is completed, for example, an operation in which an acid and water are added to the reaction mixture, extraction is performed using an organic solvent, and the obtained organic layer is dried and concentrated is performed, whereby the compound represented by Formula (3) can be isolated.

(Production Process 2)

Among the compounds of the present invention, the compound in which W represents —$OR^6$ and $R^6$ represents a hydrogen atom can be produced according to, for example, the following scheme.

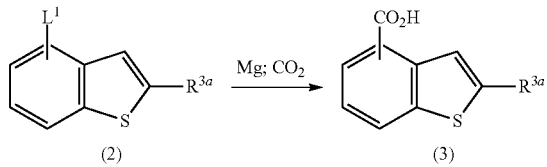

[In the formula, $L^1$ and $R^{3a}$ have the same definition as described above.]

This reaction is generally performed in a solvent. Examples of usable solvents include aromatic hydrocarbons such as benzene, toluene, and xylene; ethers such as diethylether, diisopropylether, 1,4-dioxane, tetrahydrofuran, and dimethoxyethane; and a mixture of these.

In this reaction, magnesium is used in an amount of 1 mol or more in general, and preferably in an amount of 1 molar equivalent to 2 molar equivalents, based on 1 mol of the compound represented by Formula (2).

In this reaction, carbon dioxide is used in an amount of 1 mol or more in general, and preferably in an amount of 10 mol to 1,000 mol, based on 1 mol of the compound represented by Formula (2).

The reaction temperature of this reaction is generally −100° C. to 100° C. and the reaction time of this reaction is generally 5 minutes to 30 hours.

The completion of this reaction can be confirmed by sampling a portion of the reaction mixture and using analysis means such as thin-layer chromatography and high-performance liquid chromatography. After this reaction is completed, for example, an operation in which an acid and water are added to the reaction mixture, extraction is performed using an organic solvent, and the obtained organic layer is dried and concentrated is performed, whereby the compound represented by Formula (3) can be isolated.

(Production Process 3)

Among the compounds of the present invention, the compound in which $R^1$ represents —C(O)W substituted at one of the positions 3, 4, 5, 6, and 7 and $R^2$ represents $R^{2a}$ can be produced according to, for example, the following scheme.

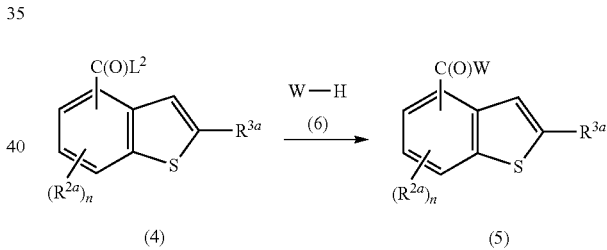

[In the formula, $R^{2a}$ represents a cyano group substituted at position 3, 4, 5, 6, or 7, a halogen atom, a nitro group, a C1-C6 alkyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a C2-C6 alkylcarbonyl group optionally having one or more halogen atoms, a benzoyl group optionally having one or more groups selected from the group Y, a C2-C6 alkoxycarbonyl group, or —$SF_5$ (provided that $R^{2a}$ is substituted at a position different from that of —C(O)$L^2$ and —C(O)W), $L^2$ represents a halogen atom, and n, W, and $R^{3a}$ have the same or different.]

This reaction is generally performed in a solvent. Examples of usable solvents include aromatic hydrocarbons such as benzene, toluene, and xylene; ethers such as diethylether, diisopropylether, 1,4-dioxane, tetrahydrofuran, and dimethoxyethane; halogenated hydrocarbons such as dichloromethane, chloroform, and 1,2-dichloroethane; amides such as N,N-dimethylformamide and N,N-dimethylacetamide; sulfones such as sulfolane; and a mixture of these.

In this reaction, the compound represented by Formula (6) is used in an amount of 1 mol or more in general, and preferably in an amount of 1 mol to 50 mol, based on 1 mol of the compound (4).

Moreover, this reaction is performed in the presence of a base. In this reaction, the base is used in an amount of 1 mol or more in general, and preferably in an amount of 1 mol to 50 mol, based on 1 mol of the compound (4).

Examples of the base used in this reaction include inorganic bases such as sodium carbonate and potassium carbonate; metal alkoxides such as sodium methoxide; alkaline metal hydrides such as sodium hydride; organic bases such as triethylamine, tributylamine, and N,N-diisopropylethylamine; and the like.

The reaction temperature of this reaction is generally 0° C. to 200° C. and preferably 30° C. to 100° C. The reaction time of this reaction is generally 30 minutes to 30 hours.

The completion of this reaction can be confirmed by sampling a portion of the reaction mixture and using analysis means such as thin-layer chromatography and high-performance liquid chromatography. After this reaction is completed, for example, a post-treatment operation in which water is added to the reaction mixture, extraction is performed using an organic solvent, and the obtained organic layer is dried and concentrated is performed, whereby the compound represented by Formula (5) can be isolated. The isolated compound that is represented by Formula (5) can also be purified by chromatography, recrystallization, and the like.

(Production Process 4)

Among the compounds of the present invention, the compound in which $R^1$ represents —C(O)W substituted at one of the positions 3, 4, 5, 6, and 7 and $R^2$ represents $R^{2a}$ can be produced according to, for example, the following scheme.

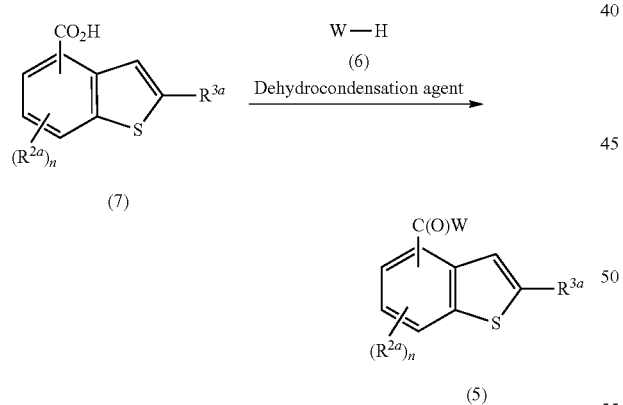

[In the formula, n, W, $R^{2a}$, and $R^{3a}$ have the same definition as described above.]

This reaction is generally performed in a solvent. Examples of usable solvents include aromatic hydrocarbons such as benzene, toluene, and xylene; ethers such as diethylether, diisopropylether, 1,4-dioxane, tetrahydrofuran, and dimethoxyethane; halogenated hydrocarbons such as dichloromethane, chloroform, and 1,2-dichloroethane; amides such as N,N-dimethylformamide and N,N-dimethylacetamide; sulfones such as sulfolane; esters such as ethyl acetate; and a mixture of these.

In this reaction, the compound represented by Formula (6) is used in an amount of 1 mol or more in general, and preferably in an amount of 1 mol to 10 mol, based on 1 mol of the compound (7).

This reaction is performed in the presence of a base if necessary. Examples of the base used in this reaction include metal carbonates such as sodium carbonate and potassium carbonate; metal alkoxides such as sodium methoxide; alkaline metal hydrides such as sodium hydride; organic bases such as triethylamine, tributylamine, and N,N-diisopropylethylamine; and the like. These are used in an amount of 1 mol to 50 mol in general, and preferably in an amount of 1 mol to 10 mol, based on 1 mol of the compound represented by Formula (7).

Examples of dehydrocondensation agents used in this reaction include carbodiimide-based agents such as N,N-dicyclohexylcarbodiimide, and 1-ethyl-3-(3-dimethylaminopropyl)carbodiimide hydrochloride; phosphonium salt-based agents such as a benzotriazol-1-yloxytrisdimethylaminophosphonium salt; and the like.

In this reaction, the dehydrocondensation agent is used in an amount of 1 mol to 50 mol in general, and preferably in an amount of 1 mol to 10 mol, based on 1 mol of the compound represented by Formula (7).

The reaction temperature of this reaction is generally 0° C. to 200° C. and preferably 30° C. to 100° C. The reaction time of this reaction is generally 30 minutes to 30 hours.

The completion of this reaction can be confirmed by sampling a portion of the reaction mixture and using analysis means such as thin-layer chromatography and high-performance liquid chromatography. After this reaction is completed, for example, a post-treatment operation in which water is added to the reaction mixture, extraction is performed using an organic solvent, and the obtained organic layer is dried and concentrated is performed, whereby the compound represented by Formula (5) can be isolated. The isolated compound that is represented by Formula (5) can also be purified by chromatography, recrystallization, and the like.

(Production Process 5)

The compound represented by Formula (9) can be produced according to, for example, the following scheme.

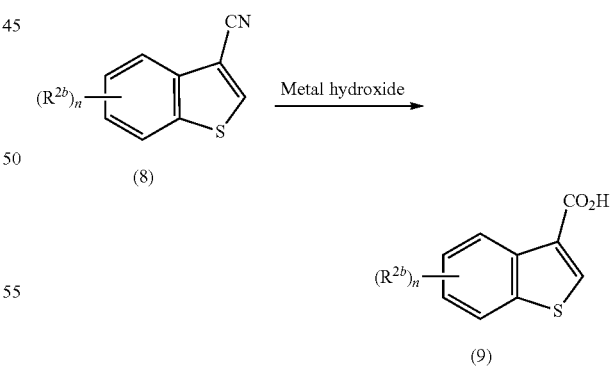

[In the formula, $R^{1a}$ represents a carboxy group substituted at position 3, $R^{2b}$ represents a halogen atom, a nitro group, a C1-C6 alkyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, —NR$^9$R$^{10}$, —S(O)$_2$NR$^4$R$^9$, —OR$^9$, or —SF$_5$, substituted at position 4, 5, 6, or 7 (provided that R$^{2b}$ is substituted at a position different from that of R$^{1a}$), and n has the same definition as described above.]

This reaction is generally performed in a solvent. Examples of the solvent used in this reaction include water; ethers such as tetrahydrofuran and 1,4-dioxane; alcohols such as methanol and ethanol; and a mixture of these.

Examples of the metal hydroxide used in this reaction include hydroxides of alkaline metals, such as lithium hydroxide, sodium hydroxide and potassium carbonate. In this reaction, the metal hydroxide is used in an amount of 5 mol or more in general, and preferably in an amount of 5 mol to 100 mol, based on 1 mol of the compound represented by Formula (8).

The reaction temperature of this reaction is generally 0° C. to 250° C. and preferably 50° C. to 150° C. The progress of this reaction can be confirmed by analyzing a portion of the reaction mixture by thin-layer chromatography, high-performance liquid chromatography, and the like. After this reaction is completed, for example, an operation in which water is added to the reaction mixture, the residue is then washed with tert-butylmethylether, concentrated hydrochloric acid is added to the aqueous layer, extraction is performed using an organic solvent, and the obtained organic layer is dried and concentrated is performed, whereby the compound represented by Formula (9) can be isolated.

(Reference Production Process 1)

The compound represented by Formula (11) can be produced according to, for example, the following scheme.

In this reaction, N,N-dimethylthiocarbamoyl chloride is used in an amount of 1 mol or more in general, and preferably in an amount of 1 mol to 5 mol, based on 1 mol of the compound represented by Formula (10).

This reaction is generally performed in the presence of a base. Examples of the base used in this reaction include organic bases such as triethylamine, tripropylamine, pyridine, dimethylaminopyridine, and 1,8-diazabicyclo[5.4.0]-7-undecene, and 1,4-diazabicyclo[2.2.2]octane; and inorganic bases such as sodium hydroxide, potassium hydroxide, calcium hydroxide, sodium carbonate, potassium carbonate, sodium hydrogen carbonate, calcium carbonate, and sodium hydride. In this reaction, the base is used in an amount of 1 mol or more in general, and preferably in an amount of 1 mol to 5 mol, based on 1 mol of the compound represented by Formula (10).

The reaction temperature of this reaction is generally 0° C. to 180° C. and preferably 10° C. to 50° C. The reaction time of this reaction is generally 10 minutes to 30 hours.

The completion of this reaction can be confirmed by sampling a portion of the reaction mixture and using analysis means such as thin-layer chromatography, high-performance liquid chromatography, and the like. After this reaction is completed, for example, an operation in which the reaction mixture is mixed with water, extraction is performed using an organic solvent, and the obtained organic layer is dried and concentrated is performed, whereby the compound represented by Formula (11) can be isolated. The isolated compound that is represented by Formula (11) can also be purified by chromatography, recrystallization, and the like.

(Reference Production Process 2)

The compound represented by Formula (12) can be produced according to, for example, the following scheme.

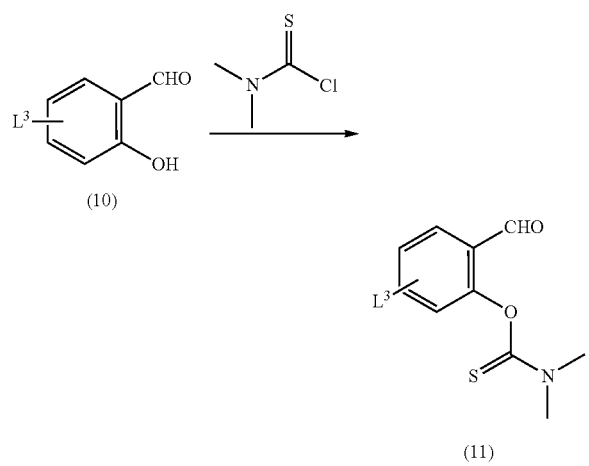

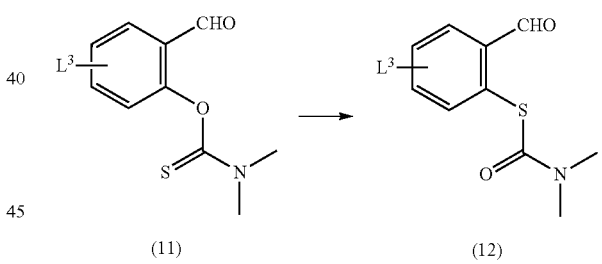

[In the formula, L$^3$ has the same definition as described above.]

This reaction is generally performed in a solvent. Examples of the usable solvent include aromatic hydrocarbons such as benzene and toluene; ethers such as diphenylether; halogenated hydrocarbons such as dichloromethane, chloroform, and 1,2-dichloroethane; nitriles such as acetonitrile; amides such as N,N-dimethylformamide, N,N-dimethylacetamide, and 1-methyl-2-pyrrolidone; sulfoxides such as dimethyl sulfoxide; sulfones such as sulfolane; and a mixture of these.

The reaction temperature of this reaction is generally 0° C. to 300° C., and preferably 80° C. to 250° C. The reaction time of this reaction is generally 10 minutes to 30 hours.

The completion of this reaction can be confirmed by sampling a portion of the reaction mixture and using analysis means such as thin-layer chromatography and high-performance liquid chromatography. After this reaction is completed, for example, an operation such as chromatogra-

[In the formula, L$^3$ represents a bromine atom or an iodine atom substituted at position 3, 4, 5, or 6.]

This reaction is generally performed in a solvent. Examples of the usable solvent include aromatic hydrocarbons such as benzene, and toluene; ethers such as diethylether, diisopropylether, 1,4-dioxane, tetrahydrofuran, and dimethoxyethane; halogenated hydrocarbons such as dichloromethane, chloroform, and 1,2-dichloroethane; nitriles such as acetonitrile; amides such as N,N-dimethylformamide and N,N-dimethylacetamide; sulfoxides such as dimethyl sulfoxide; sulfones such as sulfolane; and a mixture of these.

phy or recrystallization is performed, whereby the compound represented by Formula (12) can be isolated.

(Reference Production Process 3)

The compound represented by Formula (13) can be produced by reacting the compound represented by Formula (12) with a metal hydroxide.

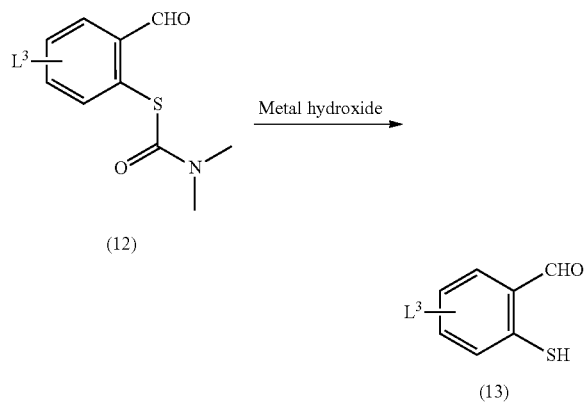

(12)

(13)

[In the formula, $L^3$ has the same definition as described above.]

This reaction is generally performed in a solvent. Examples of the solvent used in this reaction include water; ethers such as tetrahydrofuran and 1,4-dioxane; alcohols such as methanol, ethanol, and isopropanol; and a mixture of these.

Examples of the metal hydroxide used in this reaction include hydroxides of alkaline metals, such as lithium hydroxide, sodium hydroxide, and potassium hydroxide. In this reaction, the metal hydroxide is used in an amount of 2 mol or more in general, and preferably 2 mol to 100 mol, based on 1 mol of the compound represented by Formula (12).

The reaction temperature of this reaction is generally within a range of room temperature to a boiling point of the solvent, and preferably is a boiling point of the solvent. This reaction can also be performed in a sealed tube or a pressure-resistant sealed container. The reaction time of this reaction is generally about 5 minutes to 36 hours.

The progress of this reaction can be confirmed by analyzing a portion of the reaction mixture by thin-layer chromatography, high-performance liquid chromatography, and the like. After this reaction is completed, for example, an operation in which an acid and water are added to the reaction mixture, extraction is performed using an organic solvent, and the obtained organic layer is dried and concentrated is performed, whereby the compound represented by Formula (13) can be isolated.

(Reference Production Process 4)

The compound represented by Formula (14) can be produced by reacting the compound represented by Formula (13) with a reductant.

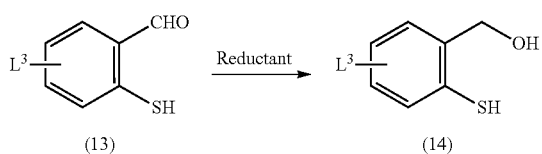

(13)          (14)

[In the formula, $L^3$ has the same definition as described above.]

This reaction is generally performed in a solvent. Examples of the solvent used in this reaction include ethers such as tetrahydrofuran and 1,4-dioxane; alcohols such as methanol, ethanol, and isopropanol; aromatic hydrocarbons such as benzene and toluene; ethers such as diphenylether; halogenated hydrocarbons such as dichloromethane, chloroform, and 1,2-dichloroethane; and a mixture of these.

Examples of the reductant used in this reaction include metal hydrides such as sodium borohydride, lithium borohydride, and lithium aluminum hydride. In this reaction, the metal hydride is used in an amount of 1 mol or more in general, and preferably in an amount of 2 mol to 20 mol, based on 1 mol of the compound represented by Formula (13).

The reaction temperature of this reaction is generally 0° C. to 300° C., and preferably 20° C. to 100° C. The reaction time of this reaction is generally 10 minutes to 30 hours.

The progress of this reaction can be confirmed by analyzing a portion of the reaction mixture by thin-layer chromatography, high-performance liquid chromatography, and the like. After this reaction is completed, for example, an operation in which an acid and water are added to the reaction mixture, extraction is performed using an organic solvent, and the obtained organic layer is dried and concentrated is performed, whereby the compound represented by Formula (14) can be isolated. The isolated compound that is represented by Formula (14) can also be purified by chromatography, recrystallization, and the like.

(Reference Production Process 5)

The compound represented by Formula (15) can be produced by reacting the compound represented by Formula (14) with triphenylphosphine hydrobromide.

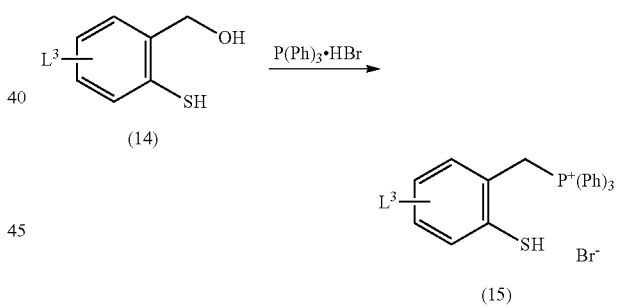

(14)

(15)

[In the formula, $L^3$ has the same definition as described above.]

This reaction is generally performed in a solvent. Examples of the solvent used in this reaction include ethers such as tetrahydrofuran, 1,4-dioxane, and diphenylether; aromatic hydrocarbons such as benzene and toluene; halogenated hydrocarbons such as dichloromethane, chloroform, and 1,2-dichloroethane; nitriles such as acetonitrile; amides such as N,N-dimethylformamide, N,N-dimethylacetamide, and 1-methyl-2-pyrrolidone; sulfoxides such as dimethyl sulfoxide; sulfones such as sulfolane; and a mixture of these.

In this reaction, triphenylphosphine hydrobromide is used in amount of 1 mol or more in general, and preferably in an amount of 1 mol to 5 mol, based on 1 mol of the compound represented by Formula (14).

The reaction temperature of this reaction is generally 0° C. to 250° C., and preferably 50° C. to 150° C. The reaction time of this reaction is generally 1 hour to 30 hours.

The progress of this reaction can be confirmed by analyzing a portion of the reaction mixture by thin-layer chromatography, high-performance liquid chromatography, and the like. After this reaction is completed, for example, an operation in which ethyl acetate is added to the reaction mixture, and the precipitated solids are collected by filtration and washed with an organic solvent is performed, whereby the compound represented by Formula (15) can be isolated.

(Reference Production Process 6)

The compound represented by Formula (16) can be produced according to, for example, the following scheme.

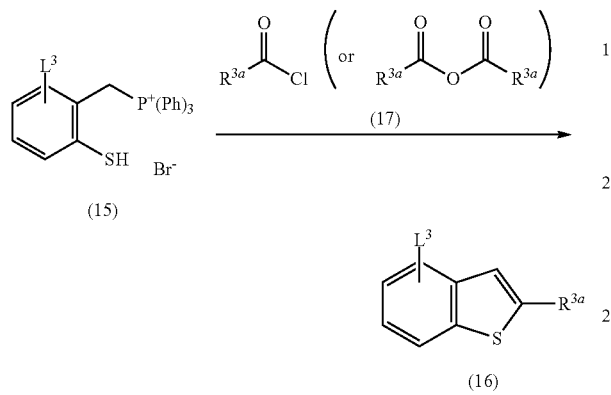

[In the formula, $L^3$ and $R^{3a}$ have the same definition as described above.]

This reaction is generally performed in a solvent. Examples of the usable solvent include ethers such as tetrahydrofuran and 1,4-dioxane; aromatic hydrocarbons such as benzene and toluene; ethers such as diphenylether; halogenated hydrocarbons such as dichloromethane, chloroform, and 1,2-dichloroethane; nitriles such as acetonitrile; amides such as N,N-dimethylformamide, N,N-dimethylacetamide, and 1-methyl-2-pyrrolidone; sulfoxides such as dimethyl sulfoxide; sulfones such as sulfolane; and a mixture of these.

Examples of the compound represented by Formula (17) used in this reaction include carboxylic acid anhydrides such as acetic anhydride, trichloroacetic anhydride, and pentafluoropropionic anhydride, and carboxylic acid halides such as acetyl chloride and heptafluorobutyryl chloride. In this reaction, $R^{3a}C(O)Cl$ or $(R^{3a}CO)_2O$ is used in an amount of 1 mol or more in general, and preferably in an amount of 1 mol to 20 mol, based on 1 mol of the compound represented by Formula (15).

This reaction is generally performed in the presence of a base. Examples of the base used in this reaction include organic bases such as triethylamine, tripropylamine, pyridine, dimethylaminopyridine, and 1,8-diazabicyclo[5.4.0]-7-undecene; and inorganic bases such as sodium hydroxide, potassium hydroxide, calcium hydroxide, sodium carbonate, potassium carbonate, sodium hydrogen carbonate, calcium carbonate, sodium hydride. In this reaction, the base is used in an amount of 1 mol or more in general, and preferably in an amount of 1 mol to 20 mol, based on 1 mol of the compound represented by Formula (15).

The reaction temperature of this reaction is generally 0° C. to 250° C. and preferably 20° C. to 150° C. The reaction time of this reaction is generally 10 minutes to 30 hours.

The progress of this reaction can be confirmed by analyzing a portion of the reaction mixture by thin-layer chromatography, high-performance liquid chromatography, and the like. After this reaction is completed, an operation such as chromatography is performed, whereby the compound represented by Formula (16) can be isolated.

(Reference Production Process 7)

The compound represented by Formula (4) can be produced according to, for example, the following scheme.

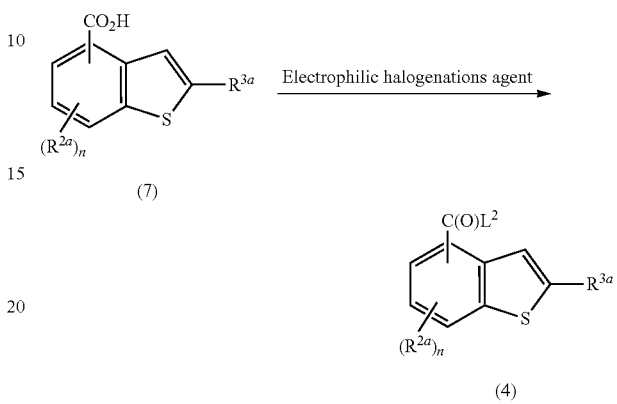

[In the formula, n, $L^2$, $R^{2a}$ and $R^{3a}$ have the same definition as described above.]

This reaction is generally performed in a solvent. Examples of the usable solvent include aromatic hydrocarbons such as benzene and toluene; ethers such as diethylether, diisopropylether, 1,4-dioxane, tetrahydrofuran, and dimethoxyethane; halogenated hydrocarbons such as dichloromethane, chloroform, and 1,2-dichloroethane; sulfoxides such as dimethyl sulfoxide; sulfones such as sulfolane; and a mixture of these.

Examples of the electrophilic halogenation agent used in this reaction include thionyl chloride, oxalyl chloride, phosphoryl chloride, sulfuryl chloride, phosphorus trichloride, phosphorus pentachloride, phosphorus tribromide, phosgene, triphosgene, and the like.

In this reaction, the electrophilic halogenation agent is used in an amount of 1 mol to 100 mol in general, and preferably in an amount of 1 mol to 20 mol, based on 1 mol of a compound represented by Formula (7).

In this reaction, N,N-dimethylformamide and the like are also optionally used in an amount of 0.001 mol to 10 mol, and preferably in an amount of 0.01 mol to 1 mol, based on 1 mol of the compound represented by Formula (7).

The reaction temperature of this reaction is generally in a range of room temperature to a boiling point of the solvent used, preferably 40° C. to a boiling point of the solvent. This reaction can be performed in a sealed tube or a pressure-resistant sealed container. The reaction time of this reaction is generally about 5 minutes to several days.

The progress of this reaction can be confirmed by analyzing a portion of the reaction mixture by thin-layer chromatography, high-performance liquid chromatography, and the like. After this reaction is completed, for example, an operation in which the reaction mixture is concentrated is performed, whereby the compound represented by Formula (4) can be isolated.

(Reference Production Process 8)

The compound represented by Formula (7) can be produced by reacting the compound represented by Formula (5) with a metal hydroxide.

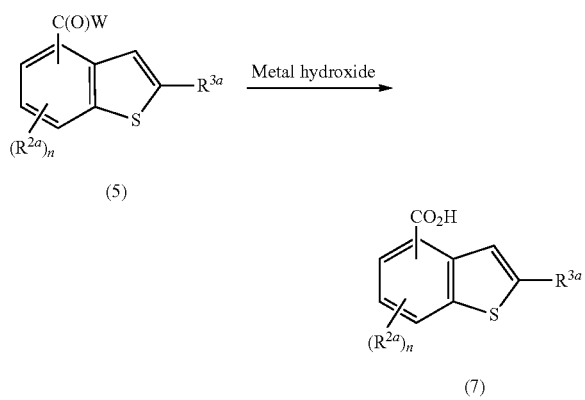

(5)

(7)

[In the formula, W, n, $R^{2a}$, and $R^{3a}$ have the same definition as described above.]

This reaction is generally performed in a solvent. Examples of the solvent used in this reaction include water; ethers such as tetrahydrofuran and 1,4-dioxane; alcohols such as methanol and ethanol; and a mixture of these.

Examples of the metal hydroxide used in this reaction include hydroxides of alkaline metals, such as lithium hydroxide, sodium hydroxide, and potassium hydroxide. In this reaction, the metal hydroxide is used in an amount of 2 mol to 20 mol in general, and preferably in an amount of 2 mol to 4 mol, based on 1 mol of the compound represented by Formula (5).

The reaction temperature of this reaction is generally in a range of room temperature to a boiling point of the solvent used, and preferably is a boiling point of the solvent. This reaction can be performed in a sealed tube or a pressure-resistant sealed container. The reaction time of this reaction is generally about 5 minutes to 36 hours.

The progress of this reaction can be confirmed by analyzing a portion of the reaction mixture by thin-layer chromatography, high-performance liquid chromatography, and the like. After this reaction is completed, for example, an operation in which an acid and water are added to the reaction mixture, extraction is then performed using an organic solvent, and the obtained organic layer is dried and concentrated is performed, whereby the compound represented by Formula (7) can be isolated.

(Reference Production Process 9)

The compound represented by Formula (19) can be produced according to, for example, the following scheme.

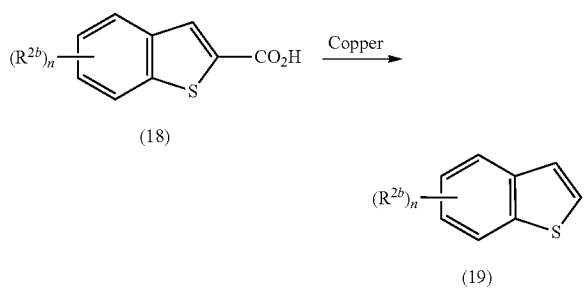

(18)

(19)

[In the formula, $R^{2b}$ represents a C1-C6 alkyl group optionally having one or more groups selected from the group X, or a phenyl group optionally having one or more groups selected from the group Y, substituted at position 4, 5, 6, or 7, and n has the same definition as described above.]

This reaction is generally performed in quinoline.

In this reaction, copper is used in an amount of 1 mol or more in general, and preferably in an amount of 1 mol to 10 mol, based on 1 mol of the compound represented by Formula (18).

The reaction temperature of this reaction is generally 100° C. to 300° C., and preferably 150° C. to 250° C. The reaction time of this reaction is generally 10 minutes to 30 hours.

The completion of this reaction can be confirmed by sampling a portion of the reaction mixture and using analysis means such as thin-layer chromatography and high-performance liquid chromatography. After this reaction is completed, for example, an operation in which an acid and water are added to the reaction mixture, extraction is performed using an organic solvent, and the obtained organic layer is dried and concentrated is performed, whereby the compound represented by Formula (19) can be isolated. The isolated compound that is represented by Formula (19) can also be purified by chromatography, recrystallization, and the like.

(Reference Production Process 10)

The compound represented by Formula (20) can be produced according to, for example, the following scheme.

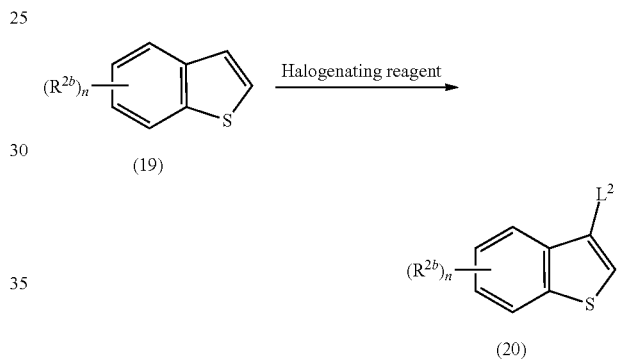

(19)

(20)

[In the formula, $L^2$, $R^{2b}$, and n have the same definition as described above.]

This reaction is generally performed in a solvent. Examples of the usable solvent include ethers such as diethylether, diisopropylether, 1,4-dioxane, tetrahydrofuran, and dimethoxyethane; halogenated hydrocarbons such as dichloromethane, chloroform, and 1,2-dichloroethane; organic carboxylic acids such as acetic acid and propionic acid; and a mixture of these.

Examples of the halogenating reagent used in this reaction include N-chlorosuccinimide, N-bromosuccinimide, dibromothioisocyanuric acid, 1,3-diiodo'-5,5'-dimethylhydantoin, and the like.

In this reaction, the halogenating reagent is used in an amount of 1 mol or more in general, and preferably in an amount of 1 mol to 5 mol, based on 1 mol of the compound represented by Formula (19).

The reaction temperature of this reaction is generally 0° C. to 200° C., and preferably 20° C. to 150° C. The reaction time of this reaction is generally 10 minutes to 100 hours.

The completion of this reaction can be confirmed by sampling a portion of the reaction mixture and using analysis means such as thin-layer chromatography and high-performance liquid chromatography. After this reaction is completed, for example, an operation in which an acid and water are added to the reaction mixture, extraction is performed using an organic solvent, and the obtained organic layer is dried and concentrated is performed, whereby the compound represented by Formula (20) can be isolated. The isolated compound that is represented by Formula (20) can also be purified by chromatography, recrystallization, and the like.

(Reference Production Process 11)

The compound represented by Formula (21) can be produced according to, for example, the following scheme.

[Structure (20): benzothiophene with $L^2$ at 3-position and $(R^{2b})_n$] → Cyan compound → [Structure (21): benzothiophene with CN at 3-position and $(R^{2b})_n$]

[In the formula, n, $L^2$, and $R^{2b}$ have the same definition as described above.]

This reaction is generally performed in a solvent. Examples of the solvent used in this reaction include amides such as dimethylformamide, N,N-dimethylacetamide, and N,N-diethylacetamide; and a mixture of these.

Examples of the cyan compound used in this reaction include copper (I) cyanide, zinc (II) cyanide, sodium cyanide, potassium cyanide, and the like.

In this reaction, the cyan compound is used in an amount of 1 mol or more in general, and preferably in an amount of 1 mol to 10 mol, based on 1 mol of the compound represented by Formula (20).

The reaction temperature of this reaction is generally 20° C. to 200° C., and preferably 80° C. to 150° C. The reaction time of this reaction is generally 10 minutes to 100 hours.

The completion of this reaction can be confirmed by sampling a portion of the reaction mixture and using analysis means such as thin-layer chromatography and high-performance liquid chromatography. After this reaction is completed, for example, an operation such as chromatography is performed, whereby the compound represented by Formula (21) can be isolated.

(Reference Production Process 12)

The compound represented by Formula (22) can be produced by reacting the compound represented by Formula (7) with a methylating agent.

[Structure (7): benzothiophene with $CO_2H$, $R^{3a}$, and $(R^{2a})_n$] → Methylating agent → [Structure (22): benzothiophene with $CO_2Me$, $R^{3a}$, and $(R^{2a})_n$]

[In the formula, n, $R^{2a}$, and $R^{3b}$ have the same definition as described above.]

This reaction is generally performed in a solvent. Examples of usable solvents include alcohols such as methanol; aromatic hydrocarbons such as benzene, toluene, and xylene; ethers such as diethylether, diisopropylether, 1,4-dioxane, tetrahydrofuran, and dimethoxyethane; halogenated hydrocarbons such as dichloromethane, chloroform, and 1,2-dichloroethane; amides such as N,N-dimethylformamide and N,N-dimethylacetamide; sulfones such as sulfolane; esters such as ethyl acetate and butyl acetate; and a mixture of these.

Examples of the methylating agent used in this reaction include iodomethane, dimethyl sulfate, trimethylsilyl diazomethane, and the like. In this reaction, the methylating agent is used in an amount of 1 mol to 20 mol, and preferably in an amount of 1 mol to 10 mol, based on 1 mol of the compound represented by Formula (7).

The reaction temperature of this reaction is generally within a range of 0° C. to 200° C., and preferably 10° C. to 100° C. This reaction can also be performed in a sealed tube or a pressure-resistant sealed container. The reaction time of this reaction is generally about 5 minutes to 36 hours.

This reaction is performed in the presence of a base if necessary. Examples of the base used in this reaction include metal carbonates such as sodium carbonate and potassium carbonate; metal alkoxides such as sodium methoxide; alkaline metal hydrides such as sodium hydride; organic bases such as triethylamine, tributylamine, and N,N-diisopropylethylamine; and the like. These are used in an amount of 1 mol to 50 mol in general, and preferably in an amount of 1 mol to 10 mol, based on 1 mol of the compound represented by Formula (7).

The progress of this reaction can be confirmed by analyzing a portion of the reaction mixture by thin-layer chromatography, high-performance liquid chromatography, and the like. After this reaction is completed, for example, a purification operation such as silica gel column chromatography is performed, whereby the compound represented by Formula (22) can be isolated.

EXAMPLES

Hereinafter, the formulation examples, production examples, application examples and test examples of the present invention will be described in more detail, but the present invention is not limited to the following examples. Moreover, in the following examples, "part(s)" indicates "part(s) by weight" unless otherwise specified.

Production Example 1

Step 1

A mixture of 4.47 g of 6-bromo-2-hydroxybenzaldehyde, 4.99 g of 1,4-diazabicyclo[2.2.2]octane, 5.50 g of N,N-dimethylthiocarbamoyl chloride, and 20 ml of N,N-dimethylformamide was stirred for 24 hours at room temperature in a nitrogen atmosphere. 50 ml of water was added to the reaction mixture, and the precipitated solids were collected by filtration and washed with water and hexane in this order. The obtained solids were dried under reduced pressure, thereby obtaining 6.34 g of O-(3-bromo-2-formylphenyl)-N,N-dimethylthiocarbamate.

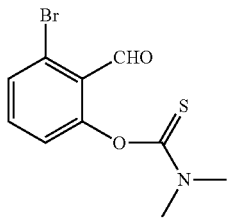

Step 2

A mixture of 6.04 g of O-(3-bromo-2-formylpheny)-N,N-dimethylthiocarbamate and 60.5 ml of diphenylether was stirred for 30 minutes at 200° C. in a nitrogen atmosphere. The mixture was cooled to room temperature and then subjected to silica gel column chromatography, thereby obtaining 4.09 g of S-(3-bromo-2-formylphenyl)-N,N-dimethylthiocarbamate.

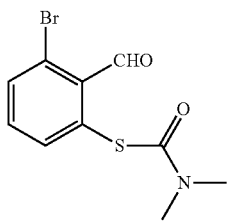

Step 3

A mixture of 4.09 g of S-(3-bromo-2-formylphenyl)-N,N-dimethyldimethylthiocarbamate, 110 ml of isopropanol, and 28 ml of a 1 M aqueous sodium hydroxide solution was stirred for 2 hours at 60° C. After being cooled to room temperature, the reaction liquid was concentrated under reduced pressure. 40 ml of a 1 M aqueous hydrochloric acid solution was added to the residues, and extraction was performed using ethyl acetate. The organic layer was washed with saturated saline, dried over magnesium sulfate, and then concentrated under reduced pressure, thereby obtaining 3.08 g of a crude product of 3-bromo-2-formylthiophenol.

Step 4

1.36 g of sodium borohydride was added to a mixture of 3.08 g of a crude product of 3-bromo-2-formylthiophenol and 110 ml of methanol at 0° C. The temperature of the reaction mixture was increased to room temperature, followed by stirring for 18 hours. The mixture was concentrated under reduced pressure, ethyl acetate and 1 M aqueous hydrochloric acid solution were added to the residues, and extraction was performed using ethyl acetate. The organic layer was washed with saturated saline, dried over magnesium sulfate, and then concentrated under reduced pressure. The obtained residues were subjected to silica gel column chromatography, thereby obtaining 2.76 g of 6-bromo-2-mercaptobenzyl alcohol.

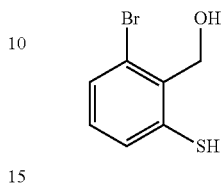

Step 5

A mixture of 2.76 g of 6-bromo-2-mercaptobenzyl alcohol, 4.72 g of triphenylphosphine hydrobromide, and 28 ml of acetonitrile was stirred for 18.5 hours under reflux. After being cooled to room temperature, the reaction mixture was concentrated under reduced pressure. Ethyl acetate was added to the residues, and the precipitated solids were collected by filtration. 120 ml of toluene, 5.36 ml of triethylamine, and 1.94 ml of trifluoroacetic anhydride were added to the solids collected by filtration, and the mixture was stirred for 2 hours under reflux. The mixture was cooled to room temperature and then concentrated under reduced pressure. Water was added to the residues, and extraction was performed using ethyl acetate. The organic layer was washed with saturated saline, dried over magnesium sulfate, and then concentrated under reduced pressure. A mixture of 15 ml of ethyl acetate and 15 ml of hexane was added to the resides, and insoluble matter was separated by filtration. The filtrate was concentrated under reduced pressure, and the obtained residues were subjected to silica gel column chromatography, thereby obtaining 2.70 g of 4-bromo-2-trifluoromethylbenzo[b]thiophene.

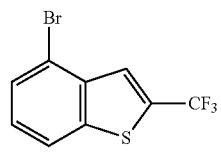 [SMILES: FC(F)(F)c1cc2c(Br)cccc2s1]

Step 6

A mixture of 1.38 g of 4-bromo-2-trifluoromethylbenzo[b]thiophene and 15 ml of tetrahydrofuran was added dropwise to a mixture of 131 mg of magnesium, 3 ml of tetrahydrofuran, and 31.2 mg of iodine in nitrogen atmosphere. The reaction mixture was stirred for 1 hour at 55° C. and then cooled to 0° C., and 2 g of dry ice was added thereto, followed by stirring for 1 hour. 10 ml of 1 M hydrochloric acid was added to the mixture, and extraction was performed using ethyl acetate. Extraction was performed on the collected organic layer by using a 1 N aqueous sodium hydroxide solution. Concentrated hydrochloric acid was added to the obtained aqueous layer, the precipitated solids were collected by filtration, washed with water and hexane, and then dried under reduced pressure, thereby obtaining 211 mg of 2-trifluoromethylbenzo[b]thiophene-4-carboxylic acid (hereinafter, described as a "compound 1 of the present invention").

Compound 1 of the Present Invention

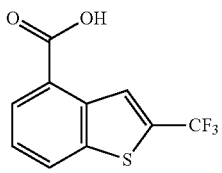 [SMILES: O=C(O)c1cccc2sc(C(F)(F)F)cc12]

$^1$H-NMR (CDCl$_3$) δ: 8.68 (s, 1H), 8.34-8.33 (m, 1H), 8.16-8.14 (m, 1H), 7.60-7.58 (m, 1H)

Production Example 2

0.58 ml of trimethylsilyl diazomethane (2 M diethylether solution) was added dropwise to a mixture of 71 mg of 2-trifluoromethylbenzo[b]thiophene-4-carboxylic acid and 1 ml of methanol at room temperature, and the residue was stirred for 45 minutes in nitrogen atmosphere. The residue was concentrated under reduced pressure, and the residues were subjected to silica gel column chromatography, thereby obtaining 74 mg of methyl 2-trifluoromethylbenzo[b]thiophene-4-carboxylate (hereinafter, described as a "compound 2 of the present invention").
Compound 2 of the Present Invention

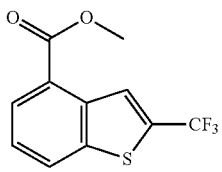 [SMILES: COC(=O)c1cccc2sc(C(F)(F)F)cc12]

$^1$H-NMR (CDCl$_3$) δ: 8.62 (s, 1H), 8.22-8.20 (m, 1H), 8.09-8.07 (m, 1H), 7.55-7.53 (m, 1H), 4.02 (s, 3H)

Production Example 3

Step 1

27 μl of oxalyl chloride and 1.1 μl of N,N-dimethylformamide were added to a mixture of 71 mg of 2-trifluoromethylbenzo[b]thiophene-4-carboxylic acid and 2 ml of dichloromethane, and the residue was stirred for 2 hours at 50° C. in nitrogen atmosphere. The reaction mixture was cooled to room temperature and then concentrated under reduced pressure, thereby obtaining 74 mg of 2-trifluoromethylbenzo[b]thiophene-4-carbonyl chloride.

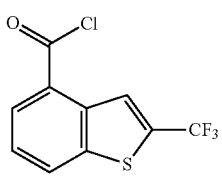 [SMILES: O=C(Cl)c1cccc2sc(C(F)(F)F)cc12]

Step 2

A mixture of 74 mg of 2-trifluoromethylbenzo[b]thiophene-4-carbonyl chloride, 0.5 ml of 1,4-dioxane, and 0.2 ml of a 28% aqueous ammonia solution was stirred for 1 hour at room temperature. Water was added to the reaction mixture, and extraction was performed using ethyl acetate. The organic layer was washed with saturated saline, dried over magnesium sulfate, and then concentrated under reduced pressure. Chloroform was added to the residues, and insoluble matter was separated by filtration. The filtrate was concentrated under reduced pressure, and a mixture of 0.1 ml of chloroform and 2 ml of hexane was added to the obtained residues, and insoluble matter was collected by filtration. The substance collected by filtration was dried under reduced pressure, thereby obtaining 36 mg of 2-trifluoromethylbenzo[b]thiophene-4-carboxamide (hereinafter, described as a "compound 3 of the present invention").
Compound 3 of the Present Invention

$^1$H-NMR (CDCl$_3$) δ: 8.44 (s, 1H), 8.04-8.02 (m, 1H), 7.72-7.70 (m, 1H), 7.52-7.50 (m, 1H), 5.85 (br s, 2H)

Production Example 4

534 mg of oxalyl chloride was added to a mixture of 500 mg of benzo[b]thiophene-5-carboxylic acid and 15 ml of methanol under ice cooling. This mixture was stirred for 6 hours under reflux. After being cooled to room temperature, the reaction mixture was concentrated under reduced pressure. Chloroform was added to the residues, and the organic layer was washed with an aqueous saturated sodium hydrogen carbonate solution and saturated saline, dried over magnesium sulfate, and concentrated under reduced pressure, thereby obtaining 411 mg of methyl benzo[b]thiophene-5-carboxylate (hereinafter, described as a "compound 5 of the present invention").
Compound 5 of the Present Invention

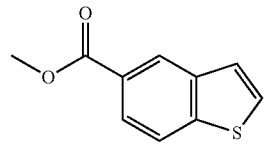

$^1$H-NMR (CDCl$_3$) δ: 8.54 (d, 1H, J=1.6 Hz), 8.01 (dd, 1H, J=8.4, 1.6 Hz), 7.93 (d, 1H, J=8.4 Hz), 7.52 (d, 1H, J=5.4 Hz), 7.43 (d, 1H, J=5.4 Hz), 3.95 (s, 3H)

Production Example 5

150 mg of oxalyl chloride was added to a mixture of 100 mg of benzo[b]thiophene-7-carboxylic acid and 5 ml of tetrahydrofuran under ice cooling. This mixture was stirred for 3 hours under reflux. After being cooled to room temperature, the mixture was concentrated under reduced pressure. 10 ml of tetrahydrofuran was added to the residues, and then 1 ml of aqueous saturated ammonia was added thereto, followed by stirring for 1 hour at room temperature. The reaction mixture was concentrated under reduced pressure, water was added to the residues, and extraction was performed using tert-butyl methyl ether. The organic layer was washed with a 1 M aqueous sodium hydroxide solution and saturated saline, dried over magnesium sulfate, and then concentrated under reduced pressure, thereby obtaining 50 mg of benzo[b]thiophene-7-carboxamide (hereinafter, described as a "compound 7 of the present invention").

Compound 7 of the Present Invention

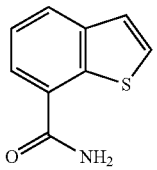

$^1$H-NMR (CDCl$_3$) δ: 8.02-8.00 (m, 1H), 7.66-7.62 (m, 2H), 7.47-7.40 (m, 2H), 6.01 (br s, 2H)

Production Example 6

142 mg of oxalyl chloride was added to a mixture of 100 mg of benzo[b]thiophene-7-carboxylic acid and 5 ml of methanol under ice cooling. This mixture was stirred for 6 hours under reflux. After being cooled to room temperature, the mixture was concentrated under reduced pressure. Tert-butyl methyl ether was added to the residues, and the organic layer was washed with a 1 M aqueous sodium hydroxide solution and saturated saline, dried over magnesium sulfate, and then concentrated under reduced pressure, thereby obtaining 60 mg of methyl benzo[b]thiophene-7-carboxylate (hereinafter, described as a "compound 8 of the present invention").

Compound 8 of the Present Invention

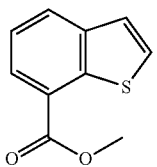

$^1$H-NMR (CDCl$_3$) δ: 8.14-8.12 (m, 1H), 8.04-8.03 (m, 1H), 7.59-7.58 (m, 1H), 7.47-7.41 (m, 2H), 4.03 (s, 3H)

Production Example 7

Step 1

A mixture of 4.47 g of 3-bromo-2-hydroxybenzaldehyde, 4.99 g of 1,4-diazabicyclo[2.2.2]octane, 5.50 g of N,N-dimethylthiocarbamoyl chloride, and 20 ml of N,N-dimethylformamide was stirred for 24 hours at room temperature in nitrogen atmosphere. 50 ml of water was added to the reaction mixture, and the precipitated solids were collected by filtration and washed with water and hexane in this order. The obtained solids were dried under reduced pressure, thereby obtaining 6.10 g of O-(6-bromo-2-formylphenyl)-N,N-dimethylthiocarbamate.

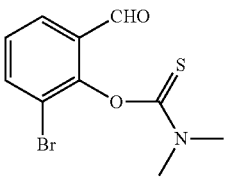

Step 2

A mixture of 6.04 g of O-(6-bromo-2-formylphenyl)-N,N-dimethylthiocarbamate and 60.5 ml of diphenylether was stirred for 30 minutes at 200° C. in nitrogen atmosphere. The mixture was cooled to room temperature and then subjected to silica gel column chromatography, thereby obtaining 5.23 g of S-(6-bromo-2-formylphenyl)-N,N-dimethylthiocarbamate.

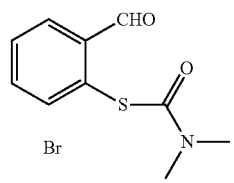

Step 3

A mixture of 5.23 g of S-(6-bromo-2-formylphenyl)-N,N-dimethylthiocarbamate, 142.5 ml of isopropanol, and 36.3 ml of a 1 M aqueous sodium hydroxide solution was stirred for 2 hours at 60° C. After being cooled to room temperature, the mixture was concentrated under reduced pressure. 50 ml of 1 M hydrochloric acid was added to the residues, and extraction was performed using ethyl acetate. The organic layer was washed with saturated saline, dried over magnesium sulfate, and then concentrated under reduced pressure, thereby obtaining 3.94 g of a crude product of 6-bromo-2-formylthiophenol.

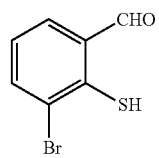

Step 4

1.74 g of sodium borohydride was added to a mixture of 3.94 g of a crude product of 6-bromo-2-formylthiophenol and 145 ml of methanol at 0° C. The temperature of the reaction mixture was increased to room temperature, followed by stirring for 18 hours. The mixture was concentrated under reduced pressure, ethyl acetate and 1 M hydrochloric acid were added to the residues, and extraction was performed using ethyl acetate. The organic layer was washed with saturated saline, dried over magnesium sulfate, and then concentrated under reduced pressure. The obtained residues were subjected to silica gel column chromatography, thereby obtaining 3.47 g of 3-bromo-2-mercaptobenzyl alcohol.

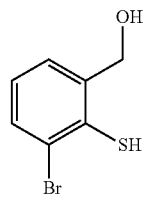

Step 5

A mixture of 3.47 g of 3-bromo-2-mercaptobenzyl alcohol, 5.98 g of triphenylphosphine hydrobromide, and 35 ml of acetonitrile was stirred for 18.5 hours under reflux. After being cooled to room temperature, the reaction mixture was concentrated under reduced pressure. Ethyl acetate was added to the residues, and the precipitated solids were collected by filtration. 150 ml of toluene, 6.78 ml of triethylamine, and 2.46 ml of trifluoroacetic anhydride were added to the solids collected by filtration, and the mixture was stirred for 2 hours under reflux. The mixture was cooled to room temperature and then concentrated under reduced pressure. Water was added to the residues, and extraction was performed using ethyl acetate. The organic layer was washed with saturated saline, dried over magnesium sulfate, and then concentrated under reduced pressure. A mixture of 20 ml of ethyl acetate and 20 ml of hexane was added to the resides, and insoluble matter was separated by filtration. The filtrate was concentrated under reduced pressure, and the obtained residues were subjected to silica gel column chromatography, thereby obtaining 3.42 g of 7-bromo-2-trifluoromethylbenzo[b]thiophene.

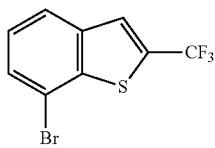

Step 6

8.06 ml of n-Butyllithium (1.2 M n-hexane solution) was added dropwise to a mixture of 3.06 g of 7-bromo-2-trifluoromethylbenzo[b]thiophene and 70 ml of tetrahydrofuran at −78° C., followed by stirring for 30 minutes. The temperature of the reaction mixture was increased to −40° C., followed by stirring for 30 minutes, and then 3 g of dry ice was added thereto. The temperature of the reaction mixture was increased to room temperature, 20 ml of a 1 M aqueous hydrochloric acid solution was then added thereto, and then extraction was performed using ethyl acetate. The collected organic layer was washed with saturated saline, dried over magnesium sulfate, and then concentrated under reduced pressure. Chloroform was added to the residues, and insoluble matter was collected by filtration and dried under reduced pressure, thereby obtaining 490 mg of 2-trifluoromethylbenzo[b]thiophene-7-carboxylic acid (hereinafter, described as a "compound 9 of the present invention").

Moreover, the filtrate was concentrated under reduced pressure, toluene was added to the obtained residues, and insoluble matter was collected by filtration. The substance collected by filtration was dried under reduced pressure, thereby obtaining 232 mg of 2-trifluoromethylbenzo[b]thiophene-3-carboxylic acid (hereinafter, described as a "compound 15 of the present invention").

Compound 9 of the Present Invention

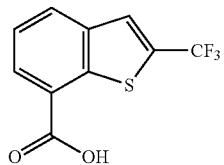 [SMILES: O=C(O)c1cccc2cc(C(F)(F)F)sc12]

$^1$H-NMR (Acetone-D$_6$) δ: 8.33-8.32 (m, 2H), 8.10-8.09 (m, 1H), 7.73-7.71 (m, 1H)

Compound 15 of the Present Invention

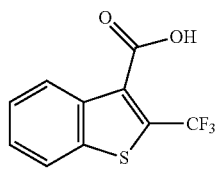

$^1$H-NMR (CDCl$_3$) δ: 8.53-8.52 (m, 1H), 7.93-7.91 (m, 1H), 7.61-7.53 (m, 2H)

Production Example 8

Step 1

0.174 ml of oxalyl chloride and 7.1 μl of N,N-dimethylformamide were added to a mixture of 454 mg of 2-trifluoromethylbenzo[b]thiophene-7-carboxylic acid and 10 ml of dichloromethane at room temperature, and the residue was stirred for 2 hours at 50° C. in nitrogen atmosphere. After being cooled to room temperature, the reaction mixture was concentrated under reduced pressure, thereby obtaining 480 mg of 2-trifluoromethylbenzo[b]thiophene-7-carbonyl chloride.

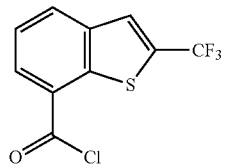 [SMILES: O=C(Cl)c1cccc2cc(C(F)(F)F)sc12]

Step 2

4 ml of methanol was added to 244 mg of 2-trifluoromethylbenzo[b]thiophene-7-carbonyl chloride at room temperature, followed by stirring for 1 hour. The mixture was concentrated under reduced pressure, and the obtained residues were subjected to silica gel column chromatography, thereby obtaining 130 mg of methyl 2-trifluoromethylbenzo[b]thiophene-7-carboxylate (hereinafter, described as a "compound 10 of the present invention").

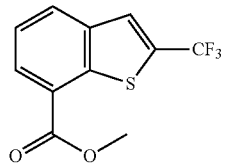 [SMILES: COC(=O)c1cccc2cc(C(F)(F)F)sc12]

Compound 10 of the Present Invention $^1$H-NMR (CDCl$_3$) δ: 8.24-8.22 (m, 1H), 8.09-8.07 (m, 1H), 7.76 (s, 1H), 7.56-7.54 (m, 1H), 4.05 (s, 3H)

Production Example 9

A mixture of 244 mg of 2-trifluoromethylbenzo[b]thiophene-7-carbonyl chloride, 3 ml of 1,4-dioxane, and 1 ml of a 28% aqueous ammonia solution was stirred for 1 hour at room temperature. Water was added to the reaction mixture, and extraction was performed using ethyl acetate. The organic layer was washed with saturated saline, dried over magnesium sulfate, and then concentrated under reduced pressure. Chloroform was added to the residues, and insoluble matter was separated by filtration. The filtrate was concentrated under reduced pressure, a mixture of 0.5 ml of chloroform and 10 ml of hexane was added to the obtained residues, and insoluble matter was collected by filtration. The substance collected by filtration was dried under reduced pressure, thereby obtaining 232 mg of 2-trifluoromethylbenzo[b]thiophene-7-carboxamide (hereinafter, described as a "compound 11 of the present invention").

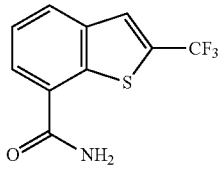 [SMILES: NC(=O)c1cccc2cc(C(F)(F)F)sc12]

Compound 11 of the Present Invention $^1$H-NMR (CDCl$_3$) δ: 8.07-8.05 (m, 1H), 7.75-7.73 (m, 2H), 7.54-7.53 (m, 1H), 6.01 (br s, 2H)

Production Example 10

370 mg of oxalyl chloride was added to a mixture of 400 mg of benzo[b]thiophene-3-carboxylic acid and 20 ml of methanol under ice cooling. This mixture was stirred for 2 hours at 80° C. After being cooled to room temperature, the reaction mixture was concentrated under reduced pressure. Tert-butyl methyl ether was added to the residues, and the residue was washed with an aqueous saturated sodium hydrogen carbonate solution and saturated saline. The organic layer was dried over magnesium sulfate and then concentrated under reduced pressure, thereby obtaining 380 mg of methyl benzo[b]thiophene-3-carboxylate (hereinafter, described as a "compound 12 of the present invention").

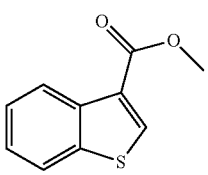

Compound 12 of the Present Invention $^1$H-NMR (CDCl$_3$) δ: 8.60 (m, 1H), 8.39 (s, 1H), 7.88 (m, 1H), 7.49 (m, 1H), 7.43 (m, 1H), 3.97 (s, 3H)

Production Example 11

Step 1

A mixture of 3.00 g of 5-trifluoromethylbenzo[b]thiophene-2-carboxylic acid, 15 ml of quinoline, and 1.29 g of copper was stirred for 2 hours at 190° C. The reaction mixture was cooled to room temperature. 1 M hydrochloric acid was added to the reaction mixture, and extraction was performed three times by using ethyl acetate. The collected organic layer was washed with saturated saline, dried over magnesium sulfate, and then concentrated under reduced pressure. The residues were subjected to silica gel column chromatography, thereby obtaining 2.03 g of 5-trifluoromethylbenzo[b]thiophene.

Step 2

1.84 g of N-bromosuccinimide was added to a mixture of 1.70 g of 5-trifluoromethylbenzo[b]thiophene, 12 ml of chloroform, and 12 ml of acetic acid over 30 minutes under ice cooling. This mixture was stirred for 6 hours at 80° C. Chloroform was added to the mixture, and the residue was washed with an aqueous saturated sodium hydrogen carbonate solution and saturated saline. The organic layer was dried over magnesium sulfate and concentrated under reduced pressure. The residues were subjected to silica gel column chromatography, thereby obtaining 1.68 g of a roughly-purified product of 3-bromo-5-trifluoromethylbenzo[b]thiophene.

A mixture of 1.68 g of the roughly-purified product of 3-bromo-5-trifluoromethylbenzo[b]thiophene, 642 mg of copper (I) cyanide, and 10 ml of N,N-diethylacetamide was stirred for 2 hours at 170° C. The reaction mixture was cooled to room temperature. 4 ml of ethylenediamine and 8 ml of water were added to the reaction mixture, and then extraction was performed three times by using tert-butyl methyl ether. The collected organic layer was washed with saturated saline, dried over magnesium sulfate, and then concentrated under reduced pressure. The residues were subjected to silica gel column chromatography, thereby obtaining 430 mg of 3-cyano-5-trifluoromethylbenzo[b]thiophene.

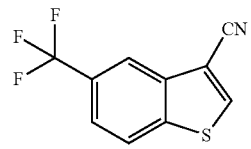 [SMILES: N#Cc1csc2ccc(C(F)(F)F)cc12]

Step 3

A mixture of 370 mg of 3-cyano-5-trifluoromethylbenzo[b]thiophene, 10 ml of a 25% aqueous sodium hydroxide solution, and 30 ml of methanol was stirred for 8 hours at 80° C. The reaction mixture was concentrated under reduced pressure, water was added thereto, and then the residue was washed with tert-butyl methyl ether. Concentrated hydrochloric acid was added to the aqueous layer, and then extraction was performed three times by using tert-butyl methyl ether. The collected organic layer was washed with saturated saline, dried over magnesium sulfate, and then concentrated under reduced pressure, thereby obtaining 231 mg of 5-trifluoromethylbenzo[b]thiophene-3-carboxylic acid (hereinafter, described as a "compound 13 of the present invention").

Compound 13 of the Present Invention

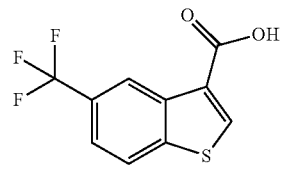 [SMILES: O=C(O)c1csc2ccc(C(F)(F)F)cc12]

¹H-NMR (CDCl₃) δ: 8.93 (s, 1H), 8.65 (s, 1H), 8.01 (d, 1H, J=8.5 Hz), 7.68 (d, 1H, J=8.5 Hz),

Production Example 12

81 mg of oxalyl chloride was added to a mixture of 120 mg of 5-trifluoromethylbenzo[b]thiophene-3-carboxylic acid and 10 ml of methanol under ice cooling. This mixture was stirred for 2 hours at 80° C. After being cooled to room temperature, the reaction mixture was concentrated under reduced pressure. Tert-butyl methyl ether was added to the residues, and the residue was washed with an aqueous saturated sodium hydrogen carbonate solution and saturated saline. The organic layer was dried over magnesium sulfate and then concentrated under reduced pressure, thereby obtaining 120 mg of methyl 5-trifluoromethylbenzo[b]thiophene-3-carboxylate (hereinafter, described as a "compound 14 of the present invention").

Compound 14 of the Present Invention

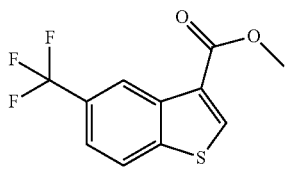 [SMILES: COC(=O)c1csc2ccc(C(F)(F)F)cc12]

¹H-NMR (CDCl₃) δ: 8.91 (s, 1H), 8.50 (s, 1H), 7.98 (d, 1H, J=8.7 Hz), 7.67 (d, 1H, J=8.7 Hz), 3.99 (s, 3H)

Production Example 13

Step 1

73 µl of oxalyl chloride and 2.7 µl of N,N-dimethylformamide were added to a mixture of 180 mg of 2-trifluoromethylbenzo[b]thiophene-3-carboxylic acid and 3 ml of dichloromethane at room temperature, and the residue was stirred for 2 hours at 50° C. in nitrogen atmosphere. The reaction mixture was cooled to room temperature and then concentrated under reduced pressure, thereby obtaining 184 mg of 2-trifluoromethylbenzo[b]thiophene-3-carbonyl chloride.

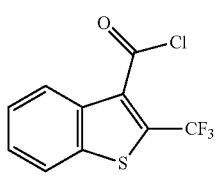 [SMILES: O=C(Cl)c1c(C(F)(F)F)sc2ccccc12]

Step 2

80 mg of 2-trifluoromethylbenzo[b]thiophene-7-carbonyl chloride was added to 4 ml of methanol at room temperature, followed by stirring for 1 hour. The mixture was concentrated under reduced pressure, and the obtained residues were subjected to silica gel column chromatography, thereby obtaining 43 mg of methyl 2-trifluoromethylbenzo[b]thiophene-3-carboxylate (hereinafter, described as a "compound 16 of the present invention").

Compound 16 of the Present Invention

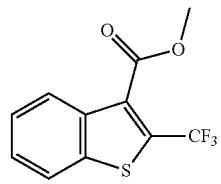 [SMILES: COC(=O)c1c(C(F)(F)F)sc2ccccc12]

¹H-NMR (CDCl₃) δ: 8.37-8.35 (m, 1H), 7.90-7.87 (m, 1H), 7.56-7.52 (m, 2H), 4.02 (s, 3H)

Production Example 14

A mixture of 108 mg of 2-trifluoromethylbenzo[b]thiophene-3-carbonyl chloride, 2 ml of 1,4-dioxane, and 0.5 ml of a 28% aqueous ammonia solution was stirred for 1 hour at room temperature. Water was added to the reaction mixture, and extraction was performed using ethyl acetate. The organic layer was washed with saturated saline, dried over magnesium sulfate, and then concentrated under reduced pressure. Chloroform was added to the residues, and insoluble matter was separated by filtration. The filtrate was concentrated under reduced pressure, a mixture of 0.1 ml of chloroform and 5 ml of hexane was added to the obtained residues, and insoluble matter was collected by filtration. The substance collected by filtration was dried under reduced pressure, thereby obtaining 74 mg of 2-trifluoromethylbenzo[b]thiophene-3-carboxamide (hereinafter, described as a "compound 17 of the present invention").

Compound 17 of the Present Invention

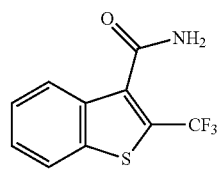

¹H-NMR (CDCl₃) δ: 8.08-8.05 (m, 1H), 7.90-7.88 (m, 1H), 7.55-7.50 (m, 2H), 5.94 (br s, 2H)

Production Example 15

Step 1

8.06 ml of n-Butyllithium (1.2 M n-hexane solution) was added dropwise to a mixture of 3.06 g of 7-bromo-2-trifluoromethylbenzo[b]thiophene and 70 ml of tetrahydrofuran at −78° C., followed by stirring for 30 minutes. The temperature of the reaction mixture was increased to −40° C., followed by stirring for 30 minutes, and then 3 g of dry ice was added thereto. The temperature of the reaction mixture was increased to room temperature, 20 ml of 1 M hydrochloric acid was then added thereto, and then extraction was performed using ethyl acetate. The collected organic layer was washed with saturated saline, dried over magnesium sulfate, and then concentrated under reduced pressure. Chloroform was added to the residues, and insoluble matter was separated by filtration. The filtrate was concentrated under reduced pressure, toluene was added to the residues, and insoluble matter was separated by filtration. The filtrate was concentrated under reduced pressure, thereby obtaining 1.91 g of a roughly-purified product of 2-trifluoromethylbenzo[b]thiophene-3,7-dicarboxylic acid.

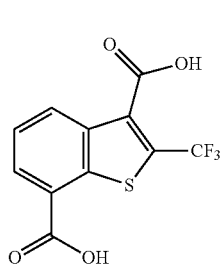 [SMILES: O=C(O)c1c(C(F)(F)F)sc2c(C(=O)O)cccc12]

Step 2

174 μl of oxalyl chloride and 7.14 μl of N,N-dimethylformamide were added to a mixture of 454 mg of a roughly-purified product of 2-trifluoromethylbenzo[b]thiophene-3,7-dicarboxylic acid and 10 ml of dichloromethane at room temperature, and the residue was stirred for 30 minutes at 60° C. in nitrogen atmosphere. After being cooled to room temperature, the reaction mixture was concentrated under reduced pressure. 4 ml of methanol was added to the residues, and the residue was stirred for 1 hour at room temperature. The mixture was concentrated under reduced pressure, and the obtained residues were subjected to silica gel column chromatography, thereby obtaining 28 mg of dimethyl 2-trifluoromethylbenzo[b]thiophene-3,7-dicarboxylate (hereinafter, described as a "compound 18 of the present invention").

Compound 18 of the Present Invention

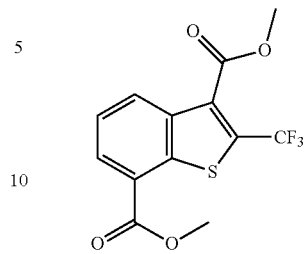

$^1$H-NMR (CDCl$_3$) δ: 8.61-8.59 (m, 1H), 8.26-8.24 (m, 1H), 7.62-7.60 (m, 1H), 4.05 (s, 3H), 4.02 (s, 3H)

Specific examples of the compounds of the present invention include the compounds (compounds 1 to 40 of the present invention) represented by Formula (1) in which n, R$^1$, R$^2$, and R$^3$ form a combination of groups shown in Tables 1 and 2.

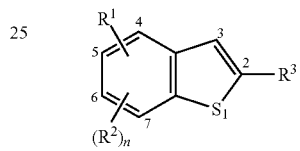

(1)

In the following table, Me represents a methyl group, Et represents an ethyl group, Ph represents a phenyl group, and Bn represents a benzyl group.

TABLE 1

| Compound of the present invention | n | R$^1$ and R$^2$ | | | | | R$^3$ | Melting point |
|---|---|---|---|---|---|---|---|---|
| | | Position 3 | Position 4 | Position 5 | Position 6 | Position 7 | | |
| 1 | 1 | H | CO$_2$H | H | H | H | CF$_3$ | — |
| 2 | 1 | H | CO$_2$Me | H | H | H | CF$_3$ | — |
| 3 | 1 | H | CONH$_2$ | H | H | H | CF$_3$ | — |
| 4 | 1 | H | H | CO$_2$H | H | H | H | 214.6° C. (decomp.) |
| 5 | 1 | H | H | CO$_2$Me | H | H | H | — |
| 6 | 1 | H | H | H | H | CO$_2$H | H | 178.5° C. |
| 7 | 1 | H | H | H | H | CONH$_2$ | H | — |
| 8 | 1 | H | H | H | H | CO$_2$Me | H | — |
| 9 | 1 | H | H | H | H | CO$_2$H | CF$_3$ | — |
| 10 | 1 | H | H | H | H | CO$_2$Me | CF$_3$ | — |
| 11 | 1 | H | H | H | H | CONH$_2$ | CF$_3$ | — |
| 12 | 1 | CO$_2$Me | H | H | H | H | H | — |
| 13 | 1 | CO$_2$H | H | CF$_3$ | H | H | H | — |
| 14 | 1 | CO$_2$Me | H | CF$_3$ | H | H | H | — |
| 15 | 1 | CO$_2$H | H | H | H | H | CF$_3$ | — |
| 16 | 1 | CO$_2$Me | H | H | H | H | CF$_3$ | — |
| 17 | 1 | CONH$_2$ | H | H | H | H | CF$_3$ | — |
| 18 | 1 | CO$_2$Me | H | H | H | CO$_2$Me | CF$_3$ | — |

TABLE 2

| Compound of the present invention | n | Position 3 | Position 4 | Position 5 | Position 6 | Position 7 | R³ | Melting point |
|---|---|---|---|---|---|---|---|---|
| 19 | 1 | CONH₂ | CF₃ | H | H | H | H | * |
| 20 | 1 | CO₂H | H | H | H | H | Me | * |
| 21 | 1 | CO₂Me | H | H | H | H | cyclopropyl carbonyl-amino- | * |
| 22 | 1 | CO₂Et | H | H | H | H | CF₃ | * |
| 23 | 1 | CONH₂ | H | H | H | H | CF₃ | * |
| 24 | 1 | CONHMe | H | H | H | H | CF₃ | * |
| 25 | 1 | CONHPh | H | H | H | H | CF₃ | * |
| 26 | 1 | CONHBn | H | H | H | H | CF₃ | * |
| 27 | 1 | CO₂H | H | H | CF₃ | H | H | * |
| 28 | 1 | CO₂Me | H | H | CF₃ | H | H | * |
| 29 | 1 | CO₂Et | H | H | CF₃ | H | H | * |
| 30 | 1 | CONH₂ | H | H | CF₃ | H | H | * |
| 31 | 1 | CONHMe | H | H | CF₃ | H | H | * |
| 32 | 1 | CONHPh | H | H | CF₃ | H | H | * |
| 33 | 1 | CONHBn | H | H | CF₃ | H | H | * |
| 34 | 1 | CO₂H | H | H | H | CF₃ | H | * |
| 35 | 1 | CO₂Me | H | H | H | CF₃ | H | * |
| 36 | 1 | CO₂Et | H | H | H | CF₃ | H | * |
| 37 | 1 | CONH₂ | H | H | H | CF₃ | H | * |
| 38 | 1 | CONHMe | H | H | H | CF₃ | H | * |
| 39 | 1 | CONHPh | H | H | H | CF₃ | H | * |
| 40 | 1 | CONHBn | H | H | H | CF₃ | H | * |

In Tables 1 and 2, ¹H-NMR data of the compounds marked with * in the column of melting point are shown below.

Compound 19 of the Present Invention

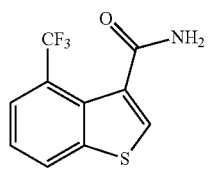 [SMILES: NC(=O)c1csc2cccc(C(F)(F)F)c12]

¹H-NMR (CDCl₃) δ: 7.70-7.68 (m, 1H), 7.52-7.49 (m, 1H), 7.13-7.10 (m, 1H), 6.49-6.46 (m, 1H), 4.29 (br s, 2H).

Compound 20 of the Present Invention

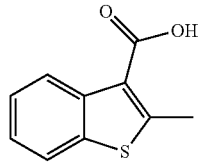

¹H-NMR (CDCl₃) δ: 8.54-8.50 (m, 1H), 7.78-7.74 (m, 1H), 7.48-7.43 (m, 1H), 7.38-7.33 (m, 1H), 2.92 (s, 3H).

Compound 21 of the Present Invention

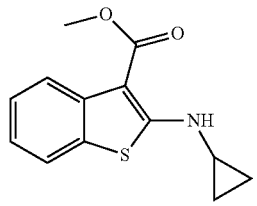 [SMILES: COC(=O)c1c(NC2CC2)sc2ccccc12]

¹H-NMR (CDCl₃) δ: 11.91 (br s, 1H), 8.27-8.24 (m, 1H), 7.75-7.73 (m, 1H), 7.43-7.39 (m, 1H), 7.31-7.28 (m, 1H), 4.04 (s, 3H), 1.80-1.73 (m, 1H), 1.25-1.20 (m, 2H), 1.04-0.99 (m, 2H).

Compound 22 of the Present Invention

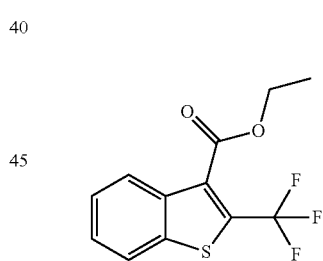

¹H-NMR (DMSO-D₆) δ: 8.26-8.24 (m, 2H), 7.67-7.63 (m, 2H), 4.44 (q, 2H, J=7.1 Hz), 1.36 (t, 3H, J=7.1 Hz).

Compound 23 of the Present Invention

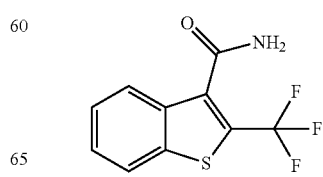

¹H-NMR (DMSO-D₆) δ: 8.24 (br s, 1H), 8.20-8.18 (m, 1H), 8.02 (br s, 1H), 7.87-7.85 (m, 1H), 7.63-7.58 (m, 2H).

Compound 24 of the Present Invention

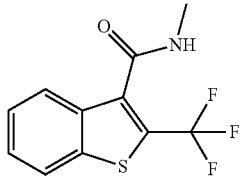 [SMILES: CNC(=O)c1c(C(F)(F)F)sc2ccccc12]

¹H-NMR (DMSO-D₆) δ: 8.71 (br s, 1H), 8.21-8.18 (m, 1H), 7.84-7.78 (m, 1H), 7.63-7.55 (m, 2H), 2.87-2.81 (m, 3H).

Compound 25 of the Present Invention

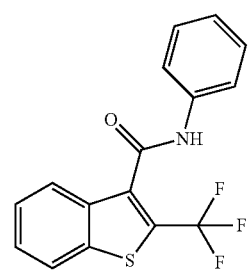 [SMILES: O=C(Nc1ccccc1)c1c(C(F)(F)F)sc2ccccc12]

¹H-NMR (DMSO-D₆) δ: 10.88 (br s, 1H), 8.27-8.25 (m, 1H), 7.90-7.87 (m, 1H), 7.72-7.69 (m, 2H), 7.68-7.60 (m, 2H), 7.41-7.38 (m, 2H), 7.18-7.15 (m, 1H).

Compound 26 of the Present Invention

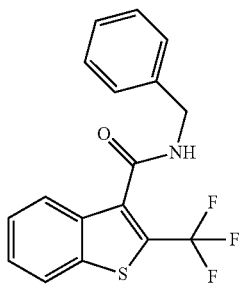 [SMILES: O=C(NCc1ccccc1)c1c(C(F)(F)F)sc2ccccc12]

¹H-NMR (DMSO-D₆) δ: 9.34 (br s, 1H), 8.23-8.18 (m, 1H), 7.82-7.76 (m, 1H), 7.62-7.57 (m, 2H), 7.38-7.34 (m, 4H), 7.32-7.27 (m, 1H), 4.56-4.52 (m, 2H)

Compound 27 of the Present Invention

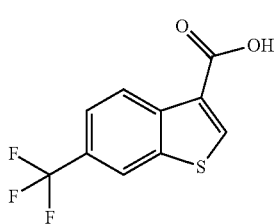 [SMILES: O=C(O)c1csc2cc(C(F)(F)F)ccc12]

¹H-NMR (DMSO-D₆) δ: 13.16 (br s, 1H), 8.87 (s, 1H), 8.69-8.66 (m, 1H), 8.63 (s, 1H), 7.83-7.79 (m, 1H).

Compound 28 of the Present Invention

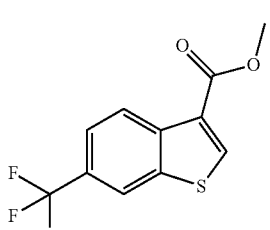

¹H-NMR (DMSO-D₆) δ: 8.95 (s, 1H), 8.65-8.63 (m, 2H), 7.85-7.83 (m, 1H), 3.91 (s, 3H).

Compound 29 of the Present Invention

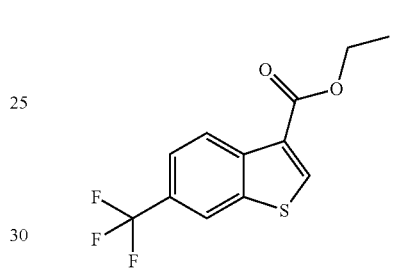

¹H-NMR (DMSO-D₆) δ: 8.92 (s, 1H), 8.64-8.62 (m, 2H), 7.85-7.78 (m, 1H), 4.37 (q, 2H, J=7.0 Hz), 1.36 (t, 3H, J=7.0 Hz).

Compound 30 of the Present Invention

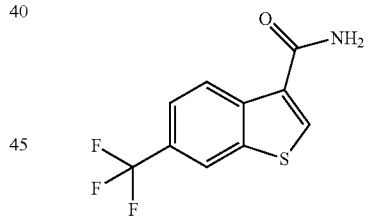

¹H-NMR (DMSO-D₆) δ: 8.72-8.70 (m, 1H), 8.64 (s, 1H), 8.57 (s, 1H), 8.04 (br s, 1H), 7.87-7.74 (m, 1H), 7.44 (br s, 1H).

Compound 31 of the Present Invention

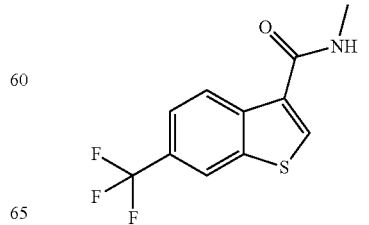

¹H-NMR (DMSO-D₆) δ: 8.68-8.62 (m, 1H), 8.57 (s, 1H), 8.54-8.51 (m, 2H), 7.76-7.74 (m, 1H), 2.82-2.80 (m, 3H).
Compound 32 of the Present Invention

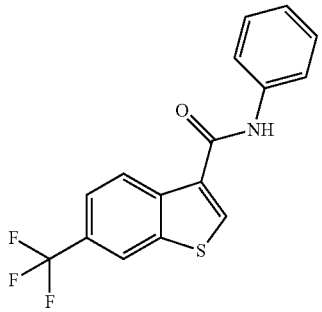 [SMILES: O=C(Nc1ccccc1)c1csc2cc(C(F)(F)F)ccc12]

¹H-NMR (DMSO-D₆) δ: 10.42 (br s, 1H), 8.82 (s, 1H), 8.63-8.59 (m, 2H), 7.81-7.77 (m, 3H), 7.40-7.36 (m, 2H), 7.14-7.10 (m, 1H).
Compound 33 of the Present Invention

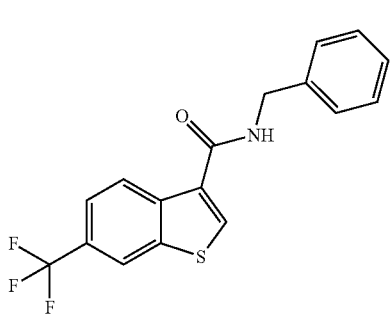 [SMILES: O=C(NCc1ccccc1)c1csc2cc(C(F)(F)F)ccc12]

Compound 34 of the Present Invention
¹H-NMR (DMSO-D₆) δ: 9.15-9.12 (m, 1H), 8.68-8.66 (m, 2H), 8.59 (s, 1H), 7.78-7.74 (m, 1H), 7.38-7.30 (m, 4H), 7.29-7.23 (m, 1H), 4.53-4.50 (m, 2H).

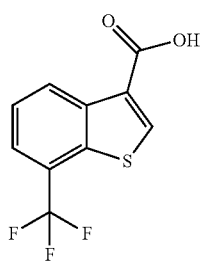

¹H-NMR (DMSO-D₆) δ: 13.24 (br s, 1H), 8.83-8.81 (m, 2H), 7.91-7.89 (m, 1H), 7.75-7.71 (m, 1H).
Compound 35 of the Present Invention ¹H-NMR (CDCl₃) δ: 8.83-8.81 (m, 1H), 8.47 (s, 1H), 7.73-7.71 (m, 1H), 7.60-7.56 (m, 1H), 3.96 (s, 3H).
Compound 36 of the Present Invention

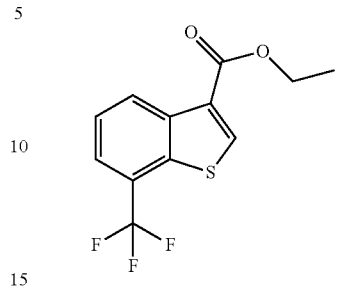

¹H-NMR (DMSO-D₆) δ: 8.83-8.81 (m, 1H), 8.47 (s, 1H), 7.72-7.70 (m, 1H), 7.59-7.55 (m, 1H), 4.43 (q, 2H, J=7.2 Hz), 1.44 (t, 3H, J=7.2 Hz).
Compound 37 of the Present Invention

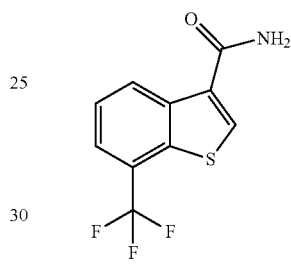

¹H-NMR (DMSO-D₆) δ: 8.83-8.81 (m, 1H), 8.56 (s, 1H), 8.07 (br s, 1H), 7.87-7.85 (m, 1H), 7.69-7.65 (m, 1H), 7.48 (br s, 1H).
Compound 38 of the Present Invention

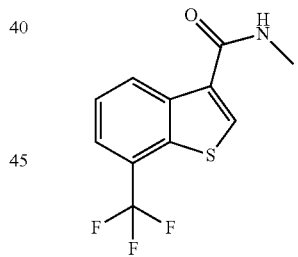

¹H-NMR (DMSO-D₆) δ: 8.76-8.74 (m, 1H), 8.56 (br s, 1H), 8.45 (s, 1H), 7.86-7.85 (m, 1H), 7.68-7.64 (m, 1H), 2.84-2.81 (m, 3H).
Compound 39 of the Present Invention

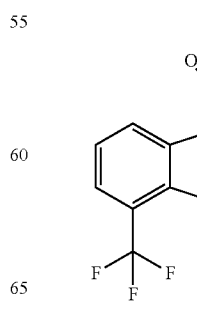

¹H-NMR (DMSO-D₆) δ: 10.47 (br s, 1H), 8.74 (s, 1H), 8.72-8.70 (m, 1H), 7.92-7.88 (m, 1H), 7.79-7.77 (m, 2H), 7.73-7.69 (m, 1H), 7.40-7.36 (m, 2H), 7.14-7.11 (m, 1H).

Compound 40 of the Present Invention

¹H-NMR (DMSO-D₆) δ: 9.20-9.16 (m, 1H), 8.78-8.76 (m, 1H), 8.59 (s, 1H), 7.88-7.86 (m, 1H), 7.70-7.66 (m, 1H), 7.39-7.32 (m, 4H), 7.28-7.24 (m, 1H), 4.53-4.51 (m, 2H).

Formulation Example 1

One of the compounds 1 to 40 of the present invention is dissolved in an amount of 10 parts in a mixture of 35 parts of xylene and 35 parts of N,N-dimethylformamide, and 14 parts of polyoxyethylene styryl phenyl ether and 6 parts of calcium dodecylbenzene sulfonate were added thereto. The residue is mixed well by stirring, thereby obtaining 10% emulsion of each compound.

Formulation Example 2

One of the compounds 1 to 40 of the present invention is added in an amount of 20 parts to a mixture of 4 parts of sodium laurylsulfate, 2 parts of calcium lignin sulfonate, 20 parts of fine powder of synthetic hydrous silicon oxide, and 54 parts of diatomaceous earth. The residue is mixed well by stirring, thereby obtaining a 20% wettable powder of each compound.

Formulation Example 3

1 part of fine powder of synthetic hydrous silicon oxide, 2 parts of calcium lignin sulfonate, 30 parts of bentonite, and 65 parts of kaolin clay are added to 2 parts of one of the compounds 1 to 40 of the present invention, and the residue is sufficiently mixed by stirring. Subsequently, water is added in an appropriate amount to the mixture, and the residue is stirred, granulated by a granulator, and dried with air, thereby obtaining 2% granules of each compound.

Formulation Example 4

One of the compounds 1 to 40 of the present invention is dissolved in an amount of 1 part in acetone in an appropriate amount, and 5 parts of fine powder of synthetic hydrous silicon oxide, 0.3 parts of PAP, and 93.7 parts of Fubasami clay are added thereto. The residue is sufficiently mixed by stirring, and acetone is removed by evaporation, thereby obtaining 1% powder of the each compound.

Formulation Example 5

10 parts of one of the compounds 1 to 40 of the present invention; 17.5 parts of white carbon containing 17.5 parts of a polyoxyethylene alkyl ether sulfate ammonium salt; and 55 parts of water are mixed with each other, and the mixture is finely pulverized by a wet pulverization method, thereby obtaining a 10% flowable agent of the each compound.

Formulation Example 6

One of the compounds 1 to 40 of the present invention is dissolved in an amount of 0.1 parts in 5 parts of xylene and 5 parts of trichloroethane, and the residue is mixed with 89.9 parts of deodorized kerosene, thereby obtaining 0.1% oil of each compound.

Next, application examples of the composition of the present invention to plant seeds will be described.

Application Example 1

100 kg of dried corn seeds are smeared with 200 ml of the respective flowable agents prepared in Formulation example 5 by using a rotary seed treatment machine (seed dresser, manufactured by Hans-Ulrich Hege GmbH), thereby obtaining the respective seeds treated.

Application Example 2

10 kg of dried wheat seeds are smeared with 40 ml of the respective flowable agents prepared in Formulation example 5 by using a rotary seed treatment machine (seed dresser, manufactured by Hans-Ulrich Hege GmbH), thereby obtaining the respective seeds treated.

Application Example 3

100 kg of dried rice seeds are smeared with 200 ml of the respective flowable agents prepared in Formulation example 5 by using a rotary seed treatment machine (seed dresser, manufactured by Hans-Ulrich Hege GmbH), thereby obtaining the respective seeds treated.

Test Example 1

Test for Evaluating Promotion of Root Growth by Hydroponics of Rice (Test Plant)
Rice (Variety: Nipponbare)
(Cultivation and Compound Treatment)

A DMSO solution, which contained one of the compounds 14, 18, 21, 23, 26, 28, 29, 30, 35, 36, 37, 39 and 40 of the present invention at a concentration of 100,000 ppm, was added to Hoagland hydroponic solution (Hoagland and Arnon, California Agricultural Experiment Station 1950 Circular 347 pp. 34) of ¼-fold concentration at a volume ratio of 1/10,000. In this manner, hydroponic solutions containing one of the compounds 14, 18, 21, 23, 26, 28, 29, 30, 35, 36, 37, 39 and 40 of the present invention at 10 ppm were prepared respectively. As an untreated control plot, a hydroponic solution obtained by adding DMSO to Hoagland hydroponic solution of ¼-fold concentration at a volume ratio of 1/10,000 was used.

Rice seeds were soaked in a 1% aqueous sodium hypochlorite solution for 10 minutes, then soaked in a 70% ethanol solution for surface sterilization, and then washed with distilled water. The sterilized seeds were soaked in a hydroponic solution containing the test compound described above at 10 ppm and incubated in a dark place for 3 days at 28° C. to perform treatment for hastening germination.

Thereafter, 30 ml of hydroponic solution containing the test compound at 10 ppm was dispensed in a plastic tube (diameter of 20 mm×height of 113 mm) of which the side was covered with cardboard to block light. A float prepared using a styrene board and vinyl mesh was floated, and the rice seeds that had undergone the treatment for hastening germination were placed on the float on the surface of the hydroponic solution. The seeds were cultivated for 3 days at 26° C., an illuminance of 4,000 lux of the top surface of the tube, a humidity of 50%, and a day length of 16 hours.

(Evaluation Method)

The nursery plants of rice obtained after cultivating were measured in terms of the length of seminal root by using WinRHIZO system (manufactured by Regent Instruments Inc). For each test plot, an average of the measured values of the seminal root of 4 or 5 individuals was determined. As a result, the seminal root was obviously longer in the test plot treated with one of the compounds 14, 18, 21, 23, 26, 28, 29, 30, 35, 36, 37, 39 and 40 of the present invention than in the untreated control plot.

TABLE 3

| Test compound | Relative value of length of seminal root (%-untreated control plot) |
|---|---|
| Compound 14 of the present invention | >5 |
| Compound 18 of the present invention | >5 |
| Compound 21 of the present invention | >5 |
| Compound 23 of the present invention | >5 |
| Compound 26 of the present invention | >5 |
| Compound 28 of the present invention | >5 |
| Compound 29 of the present invention | >5 |
| Compound 30 of the present invention | >5 |
| Compound 35 of the present invention | >5 |
| Compound 36 of the present invention | >5 |
| Compound 37 of the present invention | >5 |
| Compound 39 of the present invention | >5 |
| Compound 40 of the present invention | >5 |

Test Example 2

Test for Evaluating Promotion of Root Growth by Hydroponics of Rice (Test Plant)
Rice (Variety: Nipponbare)

(Cultivation and Compound Treatment)

A DMSO solution, which contained one of the compounds 7, 8, 9, 10, 12, 17, 20, 21, 25, 27, 28, 29, 30, 34, 35, 36, 37, 38, 39 and 40 of the present invention at a concentration of 10,000 ppm, was added to Hoagland hydroponic solution (Hoagland and Arnon, California Agricultural Experiment Station 1950 Circular 347 pp. 34) of ¼-fold concentration at a volume ratio of 1/10,000. In this manner, hydroponic solutions containing one of the compounds 7, 8, 9, 10, 12, 17, 20, 21, 25, 27, 28, 29, 30, 34, 35, 36, 37, 38, 39 and 40 of the present invention at 1 ppm were prepared respectively. As an untreated control plot, a hydroponic solution obtained by adding DMSO to Hoagland hydroponic solution of ¼-fold concentration at a volume ratio of 1/10,000 was used.

Rice seeds were soaked in a 1% aqueous sodium hypochlorite solution for 10 minutes, then soaked in a 70% ethanol solution for surface sterilization, and then washed with distilled water. The sterilized seeds were soaked in a hydroponic solution containing the test compound described above at 1 ppm and incubated in a dark place for 3 days at 28° C. to perform treatment for hastening germination.

Thereafter, 30 ml of hydroponic solution containing the test compound at 1 ppm was dispensed in a plastic tube (diameter of 20 mm×height of 113 mm) of which the side was covered with cardboard to block light. A float prepared using a styrene board and vinyl mesh was floated, and the rice seeds that had undergone the treatment for hastening germination were placed on the float on the surface of the hydroponic solution. The seeds were cultivated for 3 days at 26° C., an illuminance of 4,000 lux of the top surface of the tube, a humidity of 50%, and a day length of 16 hours.

(Evaluation Method)

The nursery plants of rice obtained after cultivation were measured in terms of the length of seminal root by using WinRHIZO system (manufactured by Regent Instruments Inc). For each test plot, an average of the measured values of the seminal root of 4 or 5 individuals was determined. As a result, the seminal root was obviously longer in the test plot treated with one of the compounds 7, 8, 9, 10, 12, 17, 20, 21, 25, 27, 28, 29, 30, 34, 35, 36, 37, 38, 39 and 40 of the present invention than in the untreated control plot.

TABLE 4

| Test compound | Relative value of length of seminal root (%-untreated control plot) |
|---|---|
| Compound 7 of the present invention | >5 |
| Compound 8 of the present invention | >5 |
| Compound 9 of the present invention | >5 |
| Compound 10 of the present invention | >5 |
| Compound 12 of the present invention | >5 |
| Compound 17 of the present invention | >5 |
| Compound 20 of the present invention | >5 |
| Compound 21 of the present invention | >5 |
| Compound 25 of the present invention | >5 |
| Compound 27 of the present invention | >5 |
| Compound 28 of the present invention | >5 |
| Compound 29 of the present invention | >5 |
| Compound 30 of the present invention | >5 |
| Compound 34 of the present invention | >5 |
| Compound 35 of the present invention | >5 |
| Compound 36 of the | >5 |

TABLE 4-continued

| Test compound | Relative value of length of seminal root (%-untreated control plot) |
|---|---|
| Compound 37 of the present invention | >5 |
| Compound 38 of the present invention | >5 |
| Compound 39 of the present invention | >5 |
| Compound 40 of the present invention | >5 |

Test Example 3

Test for Evaluating Promotion of Root Growth by Hydroponics of Rice (Test Plant)
Rice (Variety: Nipponbare)
(Cultivation and Compound Treatment)

A DMSO solution, which contained one of the compounds 1, 3, 6, 13, 15, 19, 20, 21, 26, 27, 28, 29, 30, 31, 34, 35, 36, 37, 38 and 39 of the present invention at a concentration of 1,000 ppm, was added to Hoagland hydroponic solution (Hoagland and Arnon, California Agricultural Experiment Station 1950 Circular 347 pp. 34) of ¼-fold concentration at a volume ratio of 1/10,000. In this manner, hydroponic solutions containing one of the compounds 1, 3, 6, 13, 15, 19, 20, 21, 26, 27, 28, 29, 30, 31, 34, 35, 36, 37, 38 and 39 of the present invention at 0.1 ppm were prepared respectively. As an untreated control plot, a hydroponic solution obtained by adding DMSO to Hoagland hydroponic solution of ¼-fold concentration at a volume ratio of 1/10,000 was used.

Rice seeds were soaked in a 1% aqueous sodium hypochlorite solution for 10 minutes, then soaked in a 70% ethanol solution for surface sterilization, and then washed with distilled water. The sterilized seeds were soaked in a hydroponic solution containing the test compound described above at 0.1 ppm and incubated in a dark place for 3 days at 28° C. to perform treatment for hastening germination.

Thereafter, 30 ml of hydroponic solution containing the test compound at 0.1 ppm was dispensed in a plastictube (diameter of 20 mm×height of 113 mm) of which the side was covered with cardboard to block light. A float prepared using a styrene board and vinyl mesh was floated, and the rice seeds that had undergone the treatment for hastening germination were placed on the float on the surface of the hydroponic solution. The seeds were cultivated for 3 days at 26° C., an illuminance of 4,000 lux of the top surface of the tube, a humidity of 50%, and a day length of 16 hours.

(Evaluation Method)

The nursery plants of rice obtained after culturing were measured in terms of the length of seminal root by using WinRHIZO system (manufactured by Regent Instruments Inc). For each test plot, an average of the measured values of the seminal root of 4 or 5 individuals was determined. As a result, the seminal root was obviously longer in the test plot treated with one of the compounds 1, 3, 6, 13, 15, 19, 20, 21, 26, 27, 28, 29, 30, 31, 34, 35, 36, 37, 38 and 39 of the present invention than in the untreated control plot.

TABLE 5

| Test compound | Relative value of length of seminal root (%-untreated control plot) |
|---|---|
| Compound 1 of the present invention | >5 |
| Compound 3 of the present invention | >5 |
| Compound 6 of the present invention | >5 |
| Compound 13 of the present invention | >5 |
| Compound 15 of the present invention | >5 |
| Compound 19 of the present invention | >5 |
| Compound 20 of the present invention | >5 |
| Compound 21 of the present invention | >5 |
| Compound 26 of the present invention | >5 |
| Compound 27 of the present invention | >5 |
| Compound 28 of the present invention | >5 |
| Compound 29 of the present invention | >5 |
| Compound 30 of the present invention | >5 |
| Compound 31 of the present invention | >5 |
| Compound 34 of the present invention | >5 |
| Compound 35 of the present invention | >5 |
| Compound 36 of the present invention | >5 |
| Compound 37 of the present invention | >5 |
| Compound 38 of the present invention | >5 |
| Compound 39 of the present invention | >5 |

Test Example 4

Test for Evaluating Growth Promotion Under Low-temperature Stress by Hydroponics of *Nicotiana benthamiana*

(Test Plant)
*Nicotiana benthamiana*
(Cultivation and Compound Treatment)

A DMSO solution, which contained one of the compounds 5, 14, 22, 23, 24, 25, 26, 28, 30, 31, 32, 33, 34, 35, 38, 39 and 40 of the present invention at a concentration of 10,000 ppm, was prepared. The DMSO solution of the compound of the present invention was added at a volume ratio of 1/1,000 to the Murashige•Scoog medium of a ½-fold concentration (a medium containing 2.3 g of mixed salts (manufactured by Wako Pure Chemical Industries, Ltd.), 200 mg of Myo-inositol (manufactured by Sigma-Aldrich Co. LLC.), 2 mg of nicotinic acid (manufactured by Wako Pure Chemical Industries, Ltd.), 2 mg of pyridoxine hydrochloride (manufactured by Wako Pure Chemical Industries, Ltd.), 20 mg of thiamine hydrochloride (manufactured by Wako Pure Chemical Industries, Ltd.), 20 g of sucrose (manufactured by Wako Pure Chemical Industries, Ltd.), and 1 g of MES (manufactured by DOJINDO LABORATORIES) per 1 L of water and having pH adjusted to 5.8), thereby preparing a medium containing the compound of the present invention at a concentration of 10 ppm.

Seeds of *Nicotiana benthamiana* were seeded in the 5 μL of the medium and cultured overnight at 22° C. Thereafter, 45 μL of the medium containing the compound of the present invention at a concentration of 10 ppm was added thereto, and the seeds are cultivated for 7 days at 22° C., an illuminance of 4,000 lux, and a day length of 16 hours, thereby the nursery plants raised from the *Nicotiana benthamiana* were treated with the compound.

Moreover, instead of the above medium a test plot, which was obtained by performing the same treatment by using a medium prepared by adding DMSO to the Murashige•Scoog medium of ½-fold concentration at a volume ratio of 1/1,000, was used as a control plot not treated with the compound.

(Low-Temperature Stress Treatment)

The nursery plants of the *Nicotiana benthamiana* treated with the compound were subjected to low-temperature treatment by being cultivated for 7 days at 1.5±1.0° C., an illuminance of 2,000 lux, and a day length of 16 hours.

(Evaluation)

The nursery plants of the *Nicotiana benthamiana* having undergone the low-temperature stress treatment were cultivated for 3 days at 22° C., an illuminance of 4,000 lux, and a day length of 16 hours. Thereafter, the area of green leaf was quantified by Scanalyzer HTS (manufactured by LemnaTec GmbH). Moreover, the value of the control plot not treated with the compound that had not yet been subjected to the low-temperature stress treatment was measured in the same manner. A value of a relative leaf area was calculated based on the following equation (1), and if the value of a relative leaf area was 5 or greater, the compound was evaluated to have a mitigating effect. As a result of the evaluation, it was confirmed that when the plant was treated with one of the compounds 5, 14, 22, 23, 24, 25, 26, 28, 30, 31, 32, 33, 34, 35, 38, 39 and 40 of the present invention at 10 ppm, the value of a relative leaf area was 5 or greater, compared to the area of green leaf of the control plot not treated with compound. Accordingly, it was confirmed that the treatment using the compound of the present invention brings about a growth promotion effect.

Relative leaf area=100*(a green area of a plot treated with the compound of the present invention–a green area of a control plot not treated with the compound of the present invention)/(a green area of a control plot not treated with the compound of the present invention that has not yet been subjected to low-temperature stress treatment–a green area of a control plot not treated with the compound of the present invention)     Equation (1):

Test Example 5

Test for Evaluating Growth Promotion Under Low-Temperature Stress by Hydroponics of *Nicotiana benthamiana*

(Test Plant)

*Nicotiana benthamiana*

(Cultivation and Compound Treatment)

A DMSO solution, which contained one of the compounds 6, 7, 8, 11, 12, 15, 19, 23, 24, 25, 28, 30, 31, 33, 34, 36, 37, 38 and 39 of the present invention at a concentration of 1,000 ppm, was prepared. The DMSO solution of the compound of the present invention was added at a volume ratio of 1/1,000 to the Murashige•Scoog medium of a ½-fold concentration (a medium containing 2.3 g of mixed salts (manufactured by Wako Pure Chemical Industries, Ltd.), 200 mg of Myo-inositol (manufactured by Sigma-Aldrich Co. LLC.), 2 mg of nicotinic acid (manufactured by Wako Pure Chemical Industries, Ltd.), 2 mg of pyridoxine hydrochloride (manufactured by Wako Pure Chemical Industries, Ltd.), 20 mg of thiamine hydrochloride (manufactured by Wako Pure Chemical Industries, Ltd.), 20 g of sucrose (manufactured by Wako Pure Chemical Industries, Ltd.), and 1 g of MES (manufactured by DOJINDO LABORATORIES) per 1 L of water and having pH adjusted to 5.8), thereby preparing a medium containing the compound of the present invention at a concentration of 1 ppm.

Seeds of *Nicotiana benthamiana* were seeded in the 5 μL of the medium and cultured overnight at 22° C. Thereafter, 45 μL of the medium containing the compound of the present invention at a concentration of 1 ppm was added thereto, and the seeds are cultivated for 7 days at 22° C., an illuminance of 4,000 lux, and a day length of 16 hours, thereby the nursery plants raised from the *Nicotiana benthamiana* were treated with the compound.

Moreover, instead of the above medium a test plot, which was obtained by performing the same treatment by using a medium prepared by adding DMSO to the Murashige•Scoog medium of ½-fold concentration at a volume ratio of 1/1,000, was used as a control plot not treated with the compound.

(Low-Temperature Stress Treatment)

The nursery plants of the *Nicotiana benthamiana* treated with the compound were subjected to low-temperature treatment by being cultivated for 7 days at 1.5±1.0° C., an illuminance of 2,000 lux, and a day length of 16 hours.

(Evaluation)

The nursery plants of the *Nicotiana benthamiana* having undergone the low-temperature stress treatment were cultivated for 3 days at 22° C., an illuminance of 4,000 lux, and a day length of 16 hours. Thereafter, the area of green leaf was quantified by Scanalyzer HTS (manufactured by LemnaTec GmbH). Moreover, the value of the control plot not treated with the compound that had not yet been subjected to the low-temperature stress treatment was measured in the same manner. A value of a relative leaf area was calculated based on the following equation (1), and if the value of a relative leaf area was 5 or greater, the compound was evaluated to have a mitigating effect. As a result of the evaluation, it was confirmed that when the plant was treated with one of the compounds 6, 7, 8, 11, 12, 15, 19, 23, 24, 25, 28, 30, 31, 33, 34, 36, 37, 38 and 39 of the present invention at 1 ppm, the value of a relative leaf area was 5 or greater, compared to the area of green leaf of the control plot not treated with compound. Accordingly, it was confirmed that the treatment using the compound of the present invention brings about a growth promotion effect.

Relative leaf area=100*(a green area of a plot treated with the compound of the present invention–a green area of a control plot not treated with the compound of the present invention)/(a green area of a control plot not treated with the compound of the present invention that has not yet been subjected to low-temperature stress treatment–a green area of a control plot not treated with the compound of the present invention)     Equation (1):

Test Example 6

Test for Evaluating Growth Promotion Under Low-Temperature Stress by Hydroponics of *Nicotiana benthamiana*

(Test Plant)
*Nicotiana benthamiana*
(Cultivation and Compound Treatment)
A DMSO solution, which contained one of the compounds 2, 3, 9, 10, 13, 20, 22, 26, 28, 29, 30, 31, 32, 33, 34, 35 and 36 of the present invention at a concentration of 100 ppm, was prepared. The DMSO solution of the compound of the present invention was added at a volume ratio of 1/1,000 to the Murashige•Scoog medium of a ½-fold concentration (a medium containing 2.3 g of mixed salts (manufactured by Wako Pure Chemical Industries, Ltd.), 200 mg of Myo-inositol (manufactured by Sigma-Aldrich Co. LLC.), 2 mg of nicotinic acid (manufactured by Wako Pure Chemical Industries, Ltd.), 2 mg of pyridoxine hydrochloride (manufactured by Wako Pure Chemical Industries, Ltd.), 20 mg of thiamine hydrochloride (manufactured by Wako Pure Chemical Industries, Ltd.), 20 g of sucrose (manufactured by Wako Pure Chemical Industries, Ltd.), and 1 g of MES (manufactured by DOJINDO LABORATORIES) per 1 L of water and having pH adjusted to 5.8), thereby preparing a medium containing the compound of the present invention at a concentration of 0.1 ppm.

Seeds of *Nicotiana benthamiana* were seeded in the 5 μL of the medium and cultured overnight at 22° C. Thereafter, 45 μL of the medium containing the compound of the present invention at a concentration of 0.1 ppm was added thereto, and the seeds are cultivated for 7 days at 22° C., an illuminance of 4,000 lux, and a day length of 16 hours, thereby the nursery plants raised from the *Nicotiana benthamiana* were treated with the compound.

Moreover, instead of the above medium a test plot, which was obtained by performing the same treatment by using a medium prepared by adding DMSO to the Murashige•Scoog medium of ½-fold concentration at a volume ratio of 1/1,000, was used as a control plot not treated with the compound.

(Low-Temperature Stress Treatment)
The nursery plants of the *Nicotiana benthamiana* treated with the compound were subjected to low-temperature treatment by being cultivated for 7 days at 1.5±1.0° C., an illuminance of 2,000 lux, and a day length of 16 hours.

(Evaluation)
The nursery plants of the *Nicotiana benthamiana* having undergone the low-temperature stress treatment were cultivated for 3 days at 22° C., an illuminance of 4,000 lux, and a day length of 16 hours. Thereafter, the area of green leaf was quantified by Scanalyzer HTS (manufactured by LemnaTec GmbH). Moreover, the value of the control plot not treated with the compound that had not yet been subjected to the low-temperature stress treatment was measured in the same manner. A value of a relative leaf area was calculated based on the following equation (1), and if the value of a relative leaf area was 5 or greater, the compound was evaluated to have a mitigating effect. As a result of the evaluation, it was confirmed that when the plant was treated with one of the compounds 2, 3, 9, 10, 13, 20, 22, 26, 28, 29, 30, 31, 32, 33, 34, 35 and 36 of the present invention at 0.1 ppm, the value of a relative leaf area was 5 or greater, compared to the area of green leaf of the control plot not treated with compound. Accordingly, it was confirmed that the treatment using the compound of the present invention brings about a growth promotion effect.

$$\text{Relative leaf area}=100*(\text{a green area of a plot treated with the compound of the present invention}-\text{a green area of a control plot not treated with the compound of the present invention})/(\text{a green area of a control plot not treated with the compound of the present invention that has not yet been subjected to low-temperature stress treatment}-\text{a green area of a control plot not treated with the compound of the present invention}) \quad \text{Equation (1):}$$

Test Example 7

Test for Evaluating Growth Promotion by Corn Seed Treatment (Test Plant)
Corn (Variety: Pioneer 31P41 (Manufactured by Pioneer Hi-Bred Japan))
(Seed Treatment)
A blank slurry solution containing 10% (V/V) color coat red (Becker Underwood, Inc.) and 10% (V/V) CF-Clear (Becker Underwood, Inc.) is prepared. One of the compounds 1 to 40 of the present invention is dissolved in the blank slurry such that a predetermined amount of the compound is used for treatment per 100 kg of corn seeds, thereby preparing a slurry solution. 0.35 ml of the slurry solution per 14.4 g of the seeds is put into a 50 ml centrifugal settling tube (manufactured by Becton, Dickinson and Company, Japan), and the slurry solution is stirred until it dries, thereby coating the seeds. Moreover, the seeds coated with the blank slurry are used as seeds for an untreated control plot.

(Cultivation)
Each of the seeds having undergone the seed treatment is seeded one by one in a culture soil (Aisai) in a pot (φ 55 mm×height of 58 mm), and cultivated for 18 days at 27° C., an illuminance of 5,000 lux, and a day length of 16 hours.

(Evaluation Method)
After cultivation, a fresh weight of the overground portion of each individual of the grown plant is weighed, and an average weight of each individual is determined.

As a result, the fresh weight of the overground portion is expected to be larger in the plot having undergone seed treatment by using one of the compounds 1 to 40 of the present invention than in the untreated control plot.

Test Example 8

Test for Evaluating Growth Promotion Under Low-Temperature Stress by Corn Seed Treatment (Test Plant)
Corn (Variety: Pioneer 31P41 (Manufactured by Pioneer Hi-Bred Japan)
(Seed Treatment)
A blank slurry solution containing 10% (V/V) color coat red (Becker Underwood, Inc.) and 10% (V/V) CF-Clear (Becker Underwood, Inc.) was prepared. One of the compounds 15 and 18 of the present invention was dissolved in the blank slurry such that 0.5 g, 5 g or 50 g of the compound was used for treatment per 100 kg of corn seeds, thereby preparing a slurry solution. 0.35 ml of the slurry solution per 14.4 g of the corn seeds was put into a 50 ml centrifugal settling tube (manufactured by Becton, Dickinson and Company, Japan), and the slurry solution was stirred until it dries, thereby coating the seeds. Moreover, the seeds coated with the blank slurry were used as seeds for an untreated control plot.

(Cultivation)

Each of the corn seeds having undergone the seed treatment was seeded one by one in a culture soil (Aisai) in a pot (φ 55 mm×height of 58 mm), and cultivated for 10 days at 27° C., an illuminance of 5,000 lux, and a day length of 16 hours. The grown nursery plants were used for a test.

(Low-Temperature Stress Treatment Method)

A pot in which the seeds were seeded 10 days ago was put in a phytotron set to the following temperature condition, followed by cultivation for 4 days under the following conditions.

"Conditions; a temperature of 2.5±1° C., a day length of 16 hours, and an illuminance of 5,000 lux"

(Evaluation)

After low-temperature stress treatment was performed, the seeds were cultivated for 4 days at 27° C., an illuminance of 5,000 lux, and a day length of 16 hours. Thereafter, a fresh weight of the overground portion of each individual of the plant having grown was weighed, and an average weight of each individual was determined.

As a result, the fresh weight of the overground portion was 5% or more larger in the plot having undergone seed treatment by using one of the compounds 15 and 18 of the present invention at an amount of 0.5 g, 5 g or 50 g per 100 kg of the corn seeds than in the untreated control plot.

Test Example 9

Test for Evaluating Growth Promotion Under Low-temperature Stress by Soaking Treatment of Rice (Test Plant)
Rice (Variety: Nipponbare)

(Cultivation)

Rice seeds in a required amount are soaked in an aqueous benlate solution at 1,000 ppm, and cultured overnight at 30° C. in a dark place. The aqueous benlate solution is then replaced with distilled water, and the seeds are cultured overnight again at 30° C. in a dark place to perform treatment for hastening germination.

Filter paper is placed in holes of a 406-hole plug tray, and rice seeds having undergone the germination hastening treatment are seeded on the filter paper. The Kimura B hydroponic solution (refer to Plant Science 119:39-47 (1996)) of ½-fold concentration is added thereto, and the seeds are cultivated for 5 days in a phytotron under the following conditions.

"Conditions; a temperature 28° C. for day/23° C. for night, a humidity of 70%, an illuminance of 8,500 lux, a day length of 12 hours"

(Compound Treatment)

A DMSO solution containing one of the compounds 1 to 40 of the present invention at a predetermined concentration is prepared and diluted with the Kimura B hydroponic solution of ½-fold concentration. The hydroponic solution containing the compound is dispensed by 2 ml to each well of a 24-well plate, and each of nursery plants having grown is transferred to each well and cultivated for 2 days on an illuminated culture shelf under the following conditions.

"Conditions; a temperature of 25° C., an illuminance of 5,000 lux, a day length of 12 hours"

Moreover, the nursery plants of rice cultured in the same manner by using a hydroponic solution containing 0.1% DMSO are used as an untreated control plot.

(Low-Temperature Stress Treatment)

The nursery plants of rice in a state of being in the 24-well plate are transferred to a cooling box and cultivated for 5 days under the following conditions by using cold-cathode fluorescent lamps.

"Conditions; a temperature of 4° C., an illuminance of 3,500 lux, a day length of 12 hours"

(Evaluation)

After the low-temperature stress treatment, the nursery plants of rice having undergone the low-temperature stress treatment are transferred to an illuminated culture shelf and cultivated for 4 more days under the following conditions.

"Conditions; a temperature of 25° C., an illuminance of 5,000 lux, a day length of 12 hours"

After 4 days, an image of the overground portion of the individual nursery plant of rice in each treated plot is taken, and an area of a green portion of the obtained image data is quantified by image analysis software Win Roof (manufactured by MITANI CORPORATION) to determine a green area of each individual of the overground portion of the plant. For each of the treated plots, an average of the green areas of the overground portion of individual nursery plant of rice is determined. As a result, the green area is expected to be larger in the plot treated with one of the compounds 1 to 40 of the present invention than in an untreated control plot.

Test Example 10

Test for Evaluating Growth Promotion Under Low-Temperature Stress by Rice Seed Treatment (Test Plant)
Rice (Variety: Nipponbare)

(Seed Treatment)

A blank slurry solution containing 5% (V/V) color coat red (Becker Underwood, Inc.), 5% (V/V) CF-Clear (Becker Underwood, Inc.), and 1% Maxim XL (Syngenta) is prepared. One of the compounds 1 to 40 of the present invention is dissolved in each blank slurry such that a predetermined amount of the compound is used for treatment per 100 kg of rice seeds, thereby preparing a slurry solution. 0.1 ml of the slurry solution per 3 g of the rice seeds is put into a 15 ml centrifugal settling tube (manufactured by AGC Techno Glass, Co., Ltd.), and the slurry solution is stirred until it dries, thereby coating the seeds. Moreover, the seeds coated with the blank slurry are used as seeds for an untreated control plot.

(Cultivation Method)

Filter paper is placed in holes of a 406-hole plug tray, and rice seeds having undergone the seed treatment are seeded. The Kimura B hydroponic solution (refer to Plant Science 119:39-47 (1996)) of ½-fold concentration is added thereto, and the seeds are cultivated for 10 days in a phytotron under the following conditions.

"Conditions; a temperature 28° C. for day/23° C. for night, a humidity of 70%, an illuminance of 8,500 lux, a day length of 12 hours"

(Low-Temperature Stress Treatment)

Nursery plants of rice having grown after 10 days of cultivation that are in state of being in the plug tray are transferred to a cooling box, and cultivated for 5 days under cold-cathode fluorescent lamps under the following conditions.

"Conditions: a temperature of 4° C., an illuminance of 3,500 lux, a day length of 12 hours"

(Evaluation)

Four individuals of the nursery plant of rice in the same treated plot having undergone low-temperature stress treatment are transferred to a cup (C-AP square cup 88, manufactured by Shingi Corporation) containing 60 ml of Hoagland hydroponic solution (Hoagland and Arnon, California Agricultural Experiment Station 1950 Circular 347 pp. 34) and cultivated for 12 days on an illuminated culture shelf under the following conditions.

"Conditions: a temperature of 25° C., an illuminance of 5,000 lux, a day length of 12 hours"

After 12 days, a fresh weight of the overground portion of each individual of the plant is weighed for each treated plot, and an average of the fresh weight of the overground portion of each individual of the plant is determined.

As a result, the fresh weight of the overground portion is expected to be larger in the plot having undergone treatment by using one of the compounds 1 to 40 of the present invention than in the untreated control plot.

Test Example 11

Test for Evaluating Growth Promotion Under Drought Stress by Soaking Treatment of Rice (Test Plant)
Rice (Variety: Nipponbare)
(Cultivation)

Rice seeds are soaked in an aqueous benlate solution at 1,000 ppm and cultured overnight at 30° C. in a dark place. The aqueous Benlate solution is discarded and replaced with distilled water, and the seeds are further cultured overnight at 30° C. in a dark place.

Filter paper is placed in holes of a 406-hole plug tray, and rice seeds having undergone the germination hastening treatment are seeded on the filter paper. A DMSO solution containing one of the compounds 1 to 40 of the present invention at a predetermined concentration is added to the Kimura B hydroponic solution (refer to Plant Science 119: 39-47 (1996)) of ½-fold concentration at a volume ratio of 1/10,000, and the seeds are cultivated for 14 days under the conditions of a temperature of 28° C. for day/23° C. for night, a humidity of 60%, an illuminance of 8,500 lux, and a day length of 12 hours.

(Drought Stress Treatment)

The grown nursery plants of rice are put into a 35 ml empty flat-bottomed test tube (Assist/Sarstedt) by five individuals and left to standstill for 2 days without putting a lid under the conditions of a temperature of 28° C. for day/23° C. for night, a humidity of 60%, an illuminance of 8,500 lux, and a day length of 12 hours.

(Evaluation)

The plants having undergone the drought stress treatment are put in a centrifugal settling tube (manufactured by AGC Techno Glass, Co., Ltd.) containing 100 ml of Hoagland hydroponic solution (Hoagland and Arnon, California Agricultural Experiment Station 1950 Circular 347 pp. 34) and cultivated for 14 days at a temperature of 28° C. for day/23° C. for night, a humidity of 60%, an illuminance of 8,500 lux, and a day length of 12 hours.

After 14 days, a fresh weight of the overground portion of the test plant in each test plot is weighed, and an average is determined. As a result, the fresh weight of the overground portion of the rice treated with one of the compounds 1 to 40 of the present invention is expected to be larger than that of the rice in the untreated control plot.

Test Example 12

Test for Evaluating Growth Promotion Under High-temperature Stress by Drench Treatment of Wheat (Test Plant)
Wheat (Variety: Apogee)
(Spraying Treatment)

Wheat seeds are seeded by five seeds in a culture soil (Aisai) in a plastic pot and cultivated for 10 days in a phytotron at a temperature of 18° C. for day/15° C. for night, an illuminance of 7,000 lux, and a day length of 16 hours. Before the stress test, thinning is performed to leave three individuals per pot.

One of the compounds 1 to 40 of the present invention in a predetermined amount is dissolved in DMSO to conduct 1,000-fold dilution. 15 ml of an aqueous solution containing the compound of the present invention at a predetermined concentration is used to perform soil drench treatment on the pot in which nursery plants of wheat have grown. Moreover, a 0.1% DMSO solution not containing the compound of the present invention is used as an untreated control plot.

(High-Temperature Stress Treatment)

The test plants obtained on the 13$^{th}$ day after seeding are left to standstill for 2.5 hours in a phytotron under the conditions of a temperature of 49° C., a humidity of 50%, and an illuminance of 7,000 lux.

(Evaluation)

After the high-temperature stress treatment, the plants are cultivated for 14 days in a phytotron at a temperature of 18° C. for day/15° C. for night and an illuminance of 7,000 lux. The wheat obtained on the 14$^{th}$ day after the high-temperature stress treatment is imaged using Scanalyzer 3D-VIS (manufactured by LemnaTec GmbH), and an area of the green portion of the leaves is calculated. As a result, the wheat treated with one of the compounds 1 to 40 of the present invention is expected to have an effect of increasing the green leaf area, compared to the wheat (untreated control plot) not treated with the compound of the present invention.

Test Example 13

Test for Evaluating Growth Promotion Under Drought Stress by Rice Seed Treatment (Test Plant)
Rice (Variety: Nipponbare)
(Seed Treatment)

A blank slurry solution containing 5% (V/V) color coat red (Becker Underwood, Inc.), 5% (V/V) CF-Clear (Becker Underwood, Inc.), and 1% Maxim XL (Syngenta) is prepared.

One of the compounds 1 to 40 of the present invention is dissolved in each blank slurry such that a predetermined amount of the compound is used per 100 kg rice seeds, thereby preparing a slurry solution. 0.3 ml of the slurry solution per 10 g of the rice seeds is put into a 50 ml centrifugal settling tube (manufactured by AGC Techno Glass, Co., Ltd.), and the slurry solution is stirred until it dries, thereby coating the seeds. Moreover, the seeds coated with the blank slurry solution are used as seeds for an untreated control plot.

(Cultivation)

Filter paper is placed in holes of a 406-hole plug tray, and rice seeds having undergone the seed treatment as above are seeded on the filter paper. The Kimura B hydroponic solution (refer to Plant Science 119:39-47 (1996)) of ½-fold concentration is added thereto, and the seeds are cultivated for 17 days at a temperature of 28° C. for day/23° C. for night, a humidity of 60%, an illuminance of 8,500 lux, and a day length of 12 hours.

(Drought Stress Treatment)

The grown nursery plants of rice are put into a 35 ml empty flat-bottomed test tube (Assist/Sarstedt) by five individuals and left to standstill for 2 days without putting a lid under the conditions of a temperature of 28° C. for day/23° C. for night, a humidity of 60%, an illuminance of 8,500 lux, and a day length of 12 hours.

(Evaluation)

The plants having undergone drought stress treatment are put in a centrifugal settling tube (manufactured by AGC Techno Glass, Co., Ltd.) containing 100 ml of Hoagland hydroponic solution (Hoagland and Arnon, California Agricultural Experiment Station 1950 Circular 347 pp. 34) and cultivated for 14 days at a temperature of 28° C. for day/23° C. for night, a humidity of 60%, an illuminance of 8,500 lux, and a day length of 12 hours.

After 14 days, a fresh weight of the overground portion of the five individuals of the test plant in each test plot is weighed, and an average of each test plot is determined. As a result, the plot treated with one of the compounds 1 to 40 of the present invention is expected to have an effect of increasing the fresh weight of the overground portion, compared to the untreated control plot.

Test Example 14

Test for Evaluating Growth Promotion Under Low-Temperature Stress by Soil Drench Treatment of Corn Corn seeds (variety: Pioneer 120 31P41) were seeded in a culture soil (Aisai) in a plastic pot (φ 55 mm×height of 58 mm), and cultivated for 7 days at 20-25° C., an illuminance of about 5,000 lux, and a day length of 16 hours.

A DMSO solution, which contained one of the compounds 1, 2, 4, 5, 7, 9, 10, 12 to 17, 18, 19, 23, 27, 28, 34, 35 and 38 of the present invention at a concentration of 1,000-fold concentration of each test concentration, was prepared, and then diluted with distilled water to obtain each test solution. After that, 20 ml of the obtained test solution was used to perform soil drench treatment on the foot of the test plants. The test plants were cultivated for 2 days under the conditions of a temperature of 27° C., a humidity of 40-80%, an illuminance of about 5,000 lux, and a day length of 16 hours. This was used as a test plot treated with the compound. A plot having undergone the soil drench treatment with 20 ml of a 0.1% DMSO aqueous solution instead of the above DMSO solution containing the compound was used as an untreated control plot.

The plants having undergone the soil drench treatment were cultivated for 5 days under the conditions of a temperature of 2.5° C., a humidity of 40-80%, an illuminance of about 5,000 lux, and a day length of 16 hours, thereby exposing to low-temperature stress. After the exposure to the low-temperature stress, the plants were cultivated for 4 days under the conditions of a temperature of 27° C., a humidity of 40-80%, an illuminance of about 5,000 lux, and a day length of 16 hours.

After the cultivation, the health of each plant was scored according to the following evaluation index.

5: 4 or more leaves in which ⅔ or more of the area was healthy
4: 3 leaves in which ⅔ or more of the area was healthy
3: 2 leaves in which ⅔ or more of the area was healthy
2: 1 leaf in which ⅔ or more of the area was healthy
1: No leaf in which ⅔ or more of the area was healthy
0: Plant death An average of the scores of the health of 4 individuals was determined. As a result, as shown in Table 6, the score was obviously larger in the test plot treated with one of the compounds 1, 2, 4, 5, 7, 9, 10, 12 to 17, 18, 19, 23, 27, 28, 34, 35 and 38 of the present invention than in the untreated control plot.

TABLE 6

| Test compound | Concentration tested (ppm) | Relative value of score (%-untreated control plot) |
|---|---|---|
| Compound 1 of the present invention | 1 | >5 |
| Compound 2 of the present invention | 10 | >5 |
| Compound 4 of the present invention | 10 | >5 |
| Compound 5 of the present invention | 3 | >5 |
| Compound 7 of the present invention | 10 | >5 |
| Compound 9 of the present invention | 10 | >5 |
| Compound 10 of the present invention | 1 | >5 |
| Compound 12 of the present invention | 10 | >5 |
| Compound 13 of the present invention | 10 | >5 |
| Compound 14 of the present invention | 10 | >5 |
| Compound 15 of the present invention | 0.3 | >5 |
| Compound 16 of the present invention | 10 | >5 |
| Compound 17 of the present invention | 3 | >5 |
| Compound 18 of the present invention | 3 | >5 |
| Compound 19 of the present invention | 10 | >5 |
| Compound 23 of the present invention | 10 | >5 |
| Compound 27 of the present invention | 10 | >5 |
| Compound 28 of the present invention | 10 | >5 |
| Compound 34 of the present invention | 10 | >5 |
| Compound 35 of the present invention | 10 | >5 |
| Compound 38 of the present invention | 10 | >5 |

INDUSTRIAL APPLICABILITY

The use of the method of the present invention makes it possible to effectively promote the plant growth.

The invention claimed is:

1. A method for promoting plant growth, wherein the plant is a plant that has been exposed to abiotic stress, which comprises
treating a plant with a compound represented by the following Formula (1):

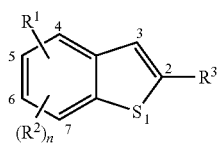
(1)

wherein
R¹ represents —C(O)W substituted at one of the positions 3, 4, 5, 6, and 7,
W represents —ON=CR⁴R⁵, —OR⁶, —SR⁷, or —NR⁴R⁸,
R² represents a cyano group, a halogen atom, a nitro group, a C1-C6 alkyl group optionally having one or more groups selected from a group X, a C2-C6 alkenyl group optionally having one or more groups selected from the group X, a C2-C6 alkynyl group optionally having one or more groups selected from the group X, a phenyl group optionally having one or more groups selected from a group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocarbonyl group, —NR⁹R¹⁰, —S(O)₂NR⁴R⁹, —OR⁹, —S(O)ₘR⁹, or —SF₅, substituted at one of the positions 3, 4, 5, 6, and 7, provided that R² is substituted at a position different from that of R¹,
R³ represents a hydrogen atom, a halogen atom, a cyano group, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a C2-C6 alkylcarbonyl group optionally having one or more halogen atoms, a benzoyl group optionally having one or more groups selected from the group Y, —NR⁹R¹⁰, —S(O)₂NR⁴R⁹, —OR⁹, or —S(O)ₘR⁹,
R⁴ and R⁵ are the same or different and each represents a C1-C6 alkyl group optionally having one or more halogen atoms, a phenyl group optionally having one or more groups selected from the group Y, or a hydrogen atom,
R⁶ represents a hydrogen atom, a C1-C6 alkyl group optionally having one or more groups selected from a group Z, a C3-C6 alkenyl group optionally having one or more groups selected from the group X, a C3-C6 alkynyl group optionally having one or more groups selected from the group X, a C4-C7 cycloalkylalkyl group optionally having one or more halogen atoms, a C3-C6 cycloalkyl group optionally having one or more halogen atoms, a phenyl group optionally having one or more groups selected from the group Y, or a C7-C9 phenylalkyl group in which a benzene ring portion may have optionally one or more groups selected from the group Y,
R⁷ represents a hydrogen atom, a C1-C6 alkyl group optionally having one or more groups selected from the group X, a C3-C6 alkenyl group optionally having one or more groups selected from the group X, a C3-C6 alkynyl group optionally having one or more groups selected from the group X, a phenyl group optionally having one or more groups selected from the group Y, or a C7-C9 phenylakyl group in which a benzene ring portion may have optionally one or more groups selected from the group Y,
R⁸ represents a hydrogen atom, a cyano group, a C1-C6 alkyl group optionally having one or more groups selected from the group Z, a phenyl group optionally having one or more groups selected from the group Y, a benzyl group in which a benzene ring portion may have optionally one or more groups selected from the group Y, —OR⁴, or —NR⁴R⁵,
R⁹ represents a C1-C6 alkyl group optionally having one or more groups selected from the group X, a C3-C6 alkenyl group optionally having one or more groups selected from the group X, a C3-C6 alkynyl group optionally having one or more groups selected from the group X, a C4-C7 cycloalkylalkyl group optionally having one or more halogen atoms, a C7-C9 phenylalkyl group in which a benzene ring portion may have optionally one or more groups selected from the group Y, a 6-membered aromatic heterocyclyl C1-C3 alkyl group in which a 6-membered aromatic heterocycle portion may have optionally one or more groups selected from the group Y, a phenyl group optionally having one or more groups selected from the group Y, a C3-C6 cycloalkyl group optionally having one or more halogen atoms, or a hydrogen atom, provided that when m in —S(O)ₘR⁹ is 1 or 2, R⁹ is not a hydrogen atom,
R¹⁰ represents a hydrogen atom, a C1-C4 alkyl group optionally having one or more halogen atoms, a C1-C4 alkylsulfonyl group optionally having one or more halogen atoms, a phenylsulfonyl group optionally having one or more groups selected from the group Y, a C7-C9 phenylalkylsulfonyl group in which a benzene ring portion may have optionally one or more groups selected from the group Y, a C2-C6 alkoxycarbonyl group, —C(O)R¹¹, or —C(O)NR⁴R⁵,
R¹¹ represents a hydrogen atom, a C1-C6 alkyl group optionally having one or more halogen atoms, a phenyl group optionally having one or more groups selected from the group Y, a 5-membered aromatic heterocyclic group optionally having one or more groups selected from the group Y, or a 6-membered aromatic heterocyclic group optionally having one or more groups selected from the group Y,
m represents 0, 1, or 2, and
n represents an integer of 0 to 4, provided that when n is an integer of 2 or greater, R²s may be the same or different and each is substituted at different positions,
the group X represents a group consisting of a halogen atom, a cyano group, and a C1-C6 alkoxy group optionally having one or more halogen atoms,
the group Y represents a group consisting of a halogen atom, a cyano group, a nitro group, a C1-C6 alkyl group optionally having one or more halogen atoms, and a C1-C6 alkoxy group optionally having one or more halogen atoms, and
the group Z represents a halogen atom, a hydroxyl group, a C1-C6 alkoxy group optionally having one or more halogen atoms, and a C2-C6 alkoxycarbonyl group,
provided that a method for promoting plant growth which comprises treating plants with a compound corresponding to the following (2) or an agriculturally acceptable salt thereof is excluded, (2) Benzo[b]thiophene-3-carboxylic acid.

2. The method according to claim 1, wherein the application to the plant includes a spraying treatment, a soil treatment, a seed treatment, or a hydroponic treatment.

3. The method according to claim 1, wherein the application to the plant is the seed treatment.

4. The method according to claim 1, wherein the plant is rice, corn, or wheat.

5. The method according to claim 1, wherein the plant is a transgenic plant.

6. The method according to claim 1, wherein the abiotic stress is high-temperature stress.

7. The method according to claim 1, wherein the abiotic stress is low-temperature stress.

8. The method according to claim 1, wherein the abiotic stress is drought stress.

9. The method according to claim 1, wherein the plant is soybean.

10. The method according to claim 1, wherein the plant is cotton.

* * * * *